(12) United States Patent
Kim et al.

(10) Patent No.: US 9,493,775 B2
(45) Date of Patent: Nov. 15, 2016

(54) INHIBITION OF THE GLYCINE CLEAVAGE SYSTEM FOR TREATMENT OF CANCER

(71) Applicant: Whitehead Institute for Biomedical Research, Cambridge, MA (US)

(72) Inventors: Dohoon Kim, Somerville, MA (US); David M. Sabatini, Cambridge, MA (US); Richard Possemato, Brighton, MA (US)

(73) Assignee: Whitehead Institute for Biomedical Research, Cambridge, MA (US)

( * ) Notice: Subject to any disclaimer, the term of this patent is extended or adjusted under 35 U.S.C. 154(b) by 0 days.

(21) Appl. No.: 14/377,470

(22) PCT Filed: Feb. 11, 2013

(86) PCT No.: PCT/US2013/025601
§ 371 (c)(1),
(2) Date: Aug. 7, 2014

(87) PCT Pub. No.: WO2013/120086
PCT Pub. Date: Aug. 15, 2013

(65) Prior Publication Data
US 2015/0011611 A1 Jan. 8, 2015

Related U.S. Application Data

(60) Provisional application No. 61/597,550, filed on Feb. 10, 2012.

(51) Int. Cl.
*A61K 48/00* (2006.01)
*C12N 15/113* (2010.01)
*A61K 45/06* (2006.01)
*A61K 31/145* (2006.01)
*A61K 31/7088* (2006.01)
*G01N 33/574* (2006.01)
*A61N 5/10* (2006.01)
*C12Q 1/68* (2006.01)
*G01N 33/50* (2006.01)
*G01N 33/573* (2006.01)

(52) U.S. Cl.
CPC ......... *C12N 15/1137* (2013.01); *A61K 31/145* (2013.01); *A61K 31/7088* (2013.01); *A61K 45/06* (2013.01); *A61N 5/1001* (2013.01); *A61N 5/1077* (2013.01); *C12Q 1/6886* (2013.01); *G01N 33/5011* (2013.01); *G01N 33/573* (2013.01); *G01N 33/57407* (2013.01); *A61N 2005/109* (2013.01); *A61N 2005/1087* (2013.01); *A61N 2005/1089* (2013.01); *C12N 2310/14* (2013.01); *C12Q 2600/106* (2013.01); *C12Q 2600/158* (2013.01); *G01N 2333/91028* (2013.01); *G01N 2500/04* (2013.01); *G01N 2800/52* (2013.01)

(58) Field of Classification Search
None
See application file for complete search history.

(56) References Cited

U.S. PATENT DOCUMENTS 6,395,780 B1   5/2002   Arlt et al.

FOREIGN PATENT DOCUMENTS

| CN | 101797242 | 8/2010 |
| WO | WO 00/66110 | 11/2000 |
| WO | WO 2004/024129 | 3/2004 |
| WO | WO 2008/133292 | 11/2008 |
| WO | WO 2011/031308 | 3/2011 |

OTHER PUBLICATIONS

Apffel, et al., "Tumor rejection in experimental animals treated with radioprotective thiols", *Cancer Research*, 35(2): 429-437 (1975).
Renwick, et al., "The crystal structure of human cytosolic serine hydroxymethyltransferase: A target for cancer chemotherapy", *Structure Current Biology, Ltd.*, 6(9): 1105-1116 (1998).
Supplementary Partial European Search Report for European Patent Application No. EP 13746071, dated Oct. 13, 2015.
Hayasaka, et al., "Effects of the metabolites of the branched-chain amino acids and cysteamine on the glycine cleavage system", *Biochem. Int.*, 6(2): 225-230 (1983).
Leivonen, et al., Identification of miR-193b Targets in Breast cells and Systems Biological Analysis of Their Functional Impact, *Molecular & Cellular Proteomics*, 10(7); 2011.
Jeitner, et al., "Inhibition of the proliferation of human neural neoplastic cell lines by cysteamine" *Cancer Lett.*, 103(1): 85-90 (1996).

(Continued)

*Primary Examiner* — Kimberly Chong
(74) *Attorney, Agent, or Firm* — Lisa M. Warren, Esq.; Morse, Barnes-Brown & Pendleton, P.C.

(57) ABSTRACT

In some aspects, methods of inhibiting survival or proliferation of a tumor cell are provided, the methods comprising inhibiting the glycine cleavage system (GCS) of the tumor cell. In some aspects, methods of treating a subject in need of treatment for a tumor, the method comprising inhibiting the GCS in the tumor. In some embodiments, the methods comprise contacting a tumor cell or tumor with a GCS inhibitor. In some embodiments, the tumor cell or tumor has elevated expression of serine hydroxymethyltransferase 2 (SH1VIT2). In some aspects, methods of identifying a tumor cell or tumor that is sensitive to inhibiting the GCS are provided, the methods comprising determining whether the tumor cell or tumor overexpresses SHMT2. In some aspects, methods of identifying a candidate anti-cancer agent are provided, the methods comprising identifying or modifying a GCS inhibitor.

14 Claims, 4 Drawing Sheets

(56) References Cited

OTHER PUBLICATIONS

Pai, et al., "Prospects of RNA interference therapy for cancer", *Gene Therapy*, 13(6): 464-477 (2006).

Wan, et al., "Autophagy-medicated chemosensitization by cysteamine in cancer cells", *International Journal of Cancer*, 129 (5): 1087-1095 (2011).

Zhang, et al., "Glycine Debarboxylase Activity Drives Non-Small Cell Lung Cancer Tumor-Initiating Cells and Tumorigenesis", *Cell*, 148: 259-272 (2012).

International Search Report for International Application No., PCT/US2013/025601, dated May 30, 2013.

Benavides, et al., "Inhibition by Aminoacetonitrile and Propargylamine of Glycine Cleavage System From Rat Brain and Mitochondria", *Biochemical Pharmacology*, 32(2): 287-291 (1983).

INHIBITION OF THE GLYCINE CLEAVAGE SYSTEM FOR TREATMENT OF CANCER

CROSS-REFERENCE TO RELATED APPLICATION

This application is a national stage filing under 35 U.S.C. 371 of International Application No. PCT/US2013/025601, filed Feb. 11, 2013, which claims the benefit of U.S. Provisional Application No. 61/597,550, filed Feb. 10, 2012. The entire teachings of the above application(s) are incorporated herein by reference. International Application PCT/US2013/025601 was published under PCT Article 21(2) in English.

BACKGROUND OF THE INVENTION

Cancer is a major cause of death and was responsible for approximately 7.6 million deaths worldwide (around 13% of all deaths) in 2008 according to the World Health Organization. Although notable successes have been achieved in the pharmacological therapy of a number of tumor types, many tumors remain difficult to treat. For example, the median life expectancy of people with glioblastoma multiforme (GBM), the most common primary brain tumor in adults, is about 12-18 months post-diagnosis, even when treated with current state of the art therapies. There is a need for new targets and therapeutic approaches for the treatment of cancer.

SUMMARY

In some aspects, the present disclosure provides a method of inhibiting proliferation or survival of a tumor cell, the method comprising inhibiting the glycine cleavage system (GCS) of the cell. In some embodiments the method comprises contacting the tumor cell with a GCS inhibitor. In some embodiments, the tumor cell overexpresses serine hydroxymethyltransferase 2 (SHMT2).

In some aspects, the disclosure provides a method of inhibiting tumor maintenance, growth, or metastasis, the method comprising contacting a tumor with a GCS inhibitor. In some embodiments the tumor overexpresses SHMT2. In some embodiments the method comprises determining that the tumor overexpresses SHMT2.

In some aspects, the disclosure provides method of treating a subject in need of treatment for a tumor the method comprising treating the subject with a GCS inhibitor. In some embodiments a method of treating a subject comprises (a) providing a subject in need of treatment for a tumor, and (b) administering a GCS inhibitor to the subject. In some embodiments the tumor overexpresses SHMT2. In some embodiments a method comprises (a) diagnosing a subject as having a tumor; and (b) treating the subject with a GCS inhibitor. In some embodiments a method comprises (a) diagnosing a subject as having a tumor; and (b) administering a GCS inhibitor to the subject. In some embodiments a method comprises determining that the subject has a tumor that overexpresses SHMT2.

In some aspects, the disclosure provides a method of classifying a tumor cell, tumor cell line, or tumor, the method comprising assessing SHMT2 expression in the tumor cell, tumor cell line, or tumor, and (b) classifying the tumor cell, tumor cell line, or tumor based on the result of step (a). In some embodiments step (b) comprises classifying the tumor cell, tumor cell line, or tumor as having increased likelihood of being sensitive to GCS inhibition if the tumor cell, tumor cell line, or tumor oveexpresses SHMT2.

In some aspects, the disclosure provides a method of identifying a subject who is a suitable candidate for treatment with a GCS inhibitor, the method comprising assessing SHMT2 expression in a tumor sample obtained from the subject.

DETAILED DESCRIPTION

I. Glossary

Figure 1:
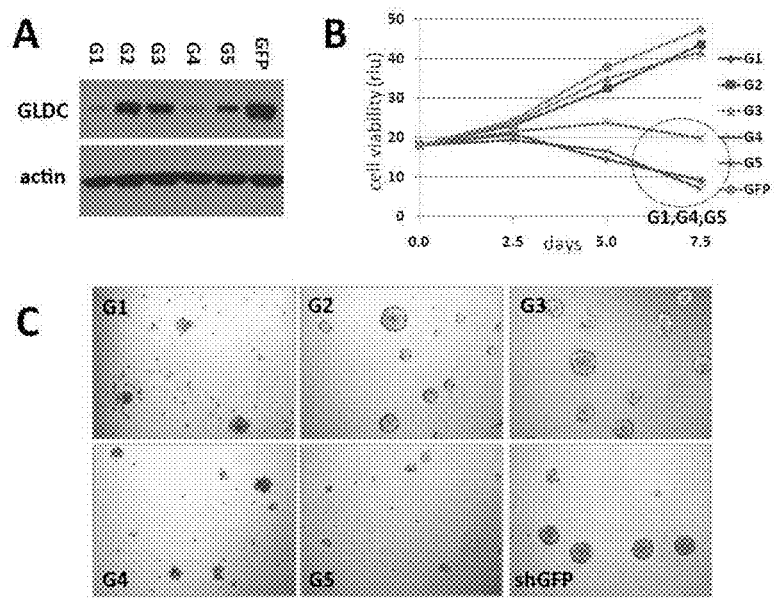
FIGS. 1A-1C. shRNAs which knock down GLDC are toxic to GBMSCs. BT145 cells were either infected with a lentivirus expressing hairpins targeting GLDC (G1 to G5) or a control hairpin targeting GFP. (A) Western blotting for GLDC demonstrates strong suppression of GLDC expression for hairpins G1, G4, and G5. (B) When cell viability was measured using a ATP assay, we found that shRNAs G1, G4, and G5 significantly impaired cell viability relative to GFP control hairpin, but not G2 or G3 shRNAs. Differences between G1, G4, and G5 to the GFP control were each statistically significant at 5 days and 7.5 days (p<0.05) (error bars not shown for clarity). (C) Morphology of BT145 neurospheres following GLDC knockdown indicates toxicity. As shown, G2, G3, and GFP infected neurospheres form large, round, and regular spheres, indicating viability. On the other hand, G1, G4, or G5 infected spheres are small, irregular, and are in the process of disintegrating, indicating cell death and impaired growth.

Descriptions and information relating to certain terms used in the present disclosure are collected here for convenience.

"Agent" is used herein to refer to any substance, compound (e.g., molecule), supramolecular complex, material, or combination or mixture thereof. A compound may be any agent that can be represented by a chemical formula, chemical structure, or sequence. Exemplary agents, include, e.g., small molecules, polypeptides, nucleic acids (e.g., RNAi agents, antisense oligonucleotide, aptamers), lipids, polysaccharides, etc. In general, agents may be obtained using any suitable method known in the art. The ordinary skilled artisan will select an appropriate method based, e.g., on the nature of the agent. An agent may be at least partly purified. In some embodiments an agent may be provided as part of a composition, which may contain, e.g., a counter-ion, aqueous or non-aqueous diluent or carrier, buffer, preservative, or other ingredient, in addition to the agent, in various embodiments. In some embodiments an agent may be provided as a salt, ester, hydrate, or solvate. In some embodiments an agent is cell-permeable, e.g., within the range of typical agents that are taken up by cells and act intracellularly, e.g., within mammalian cells, to produce a biological effect. Certain compounds may exist in particular geometric or stereoisomeric forms. Such compounds, including cis- and trans-isomers, E- and Z-isomers, R- and S-enantiomers, diastereomers, (D)-isomers, (L)-isomers, (−)- and (+)-isomers, racemic mixtures thereof, and other mixtures thereof are encompassed by this disclosure in various embodiments unless otherwise indicated. Certain compounds may exist in a variety or protonation states, may have a variety of configurations, may exist as solvates (e.g., with water (i.e. hydrates) or common solvents) and/or may have different crystalline forms (e.g., polymorphs) or different tautomeric forms. Embodiments exhibiting such alternative protonation states, configurations, solvates, and forms are encompassed by the present disclosure where applicable.

An "analog" of a first agent refers to a second agent that is structurally and/or functionally similar to the first agent. A "structural analog" of a first agent is an analog that is structurally similar to the first agent. A structural analog of an agent may have substantially similar physical, chemical, biological, and/or pharmacological propert(ies) as the agent or may differ in at least one physical, chemical, biological, or pharmacological property. In some embodiments at least one such property may be altered in a manner that renders the analog more suitable for a purpose of interest. In some embodiments a structural analog of an agent differs from the agent in that at least one atom, functional group, or substructure of the agent is replaced by a different atom, functional group, or substructure in the analog. In some embodiments, a structural analog of an agent differs from the agent in that at least one hydrogen or substituent present in the agent is replaced by a different moiety (e.g., a different substituent) in the analog. "Substrate analog" refers to an agent that structurally resembles the substrate of an enzymatic reaction. The structure of a substrate analog may be sufficiently similar to that of a normal substrate so that the substrate analog can substitute for the normal substrate in a physical interaction (e.g., binding) with an enzyme. In some embodiments the structure of a substrate analog is sufficiently different from that of a normal substrate so that the substrate analog may not undergo a chemical reaction as would a normal substrate (e.g., the reaction may not detectably occur or may occur more slowly). "Transition state analog" refers to an agent that structurally resembles the transition state of a substrate in an enzymatic reaction. The structure of a transition state analog may be sufficiently similar to that of a normal transition state so that the transition state analog can physically interact with (e.g., bind to) an enzyme. In some embodiments the structure of a transition state analog is sufficiently different to that of a normal transition state so that the transition state analog may not undergo a chemical reaction as would a normal transition state. A substrate analog or transition state analog may act as an enzyme inhibitor by, e.g., by blocking the enzyme active site. In some embodiments a substrate analog or transition state analog may comprise a moiety that reacts with an enzyme to form a covalent bond.

The term "antibody" refers to an immunoglobulin, whether natural or wholly or partially synthetically produced. An antibody may be a member of any immunoglobulin class, including any of the mammalian, e.g., human, classes: IgG, IgM, IgA, IgD, and IgE, or subclasses thereof, and may be an antibody fragment, in various embodiments. An antibody may originate from any of a variety of vertebrate (e.g., mammalian or avian) organisms, e.g., mouse, rat, rabbit, hamster, goat, chicken, human, camelid, shark, etc., or may be encoded at least in part by immunoglobulin gene sequences derived from any of the foregoing organisms. In some embodiments an antibody is a nanobody. As used herein, the term "antibody fragment" refers to any of various portions of an antibody that contain less than a complete antibody structure (e.g., less than the complete structure of a conventional antibody composed of two heavy and two light chains). In general, an antibody fragment retains at least a significant portion of the complete antibody's specific binding ability. Examples of antibody fragments include, but are not limited to, Fab, Fab', F(ab')2, scFv, Fv, dsFv diabody, minibody, Fd fragments, and single domain antibodies. Standard methods of antibody identification and production known in the art can be used to produce an antibody that binds to a polypeptide of interest. In some embodiments an antibody is a monoclonal antibody. Monoclonal antibodies can be identified and/or produced using, e.g., hybridoma technology or recombinant nucleic acid technology in various embodiments. In some embodiments an antibody is selected from a library, e.g., a phage or yeast display library. In some embodiments, an antibody is a chimeric, humanized, or fully human antibody. In some embodiments an antibody is a polyclonal antibody. In some embodiments an antibody comprises at least two distinct antigen-binding sites that bind to distinct epitopes. In some embodiments an antibody has a label attached (e.g., covalently attached) thereto (e.g., the label may comprise a radioisotope, fluorescent agent, enzyme, hapten). In some embodiments a single chain antibody (scFv) may be created by joining the antigen-binding variable regions of heavy chain (VH) and light chain (VL) with a linking domain. A linking domain may comprise a peptide of, e.g., about 10 to about 25 amino acids.

The term "aptamer" refers to an oligonucleotide that binds specifically and with high affinity to a target of interest, e.g., a polypeptide. (It will be understood that the term "aptamer" is typically employed when the target of interest is not a nucleic acid complementary to the oligonucleotide.) An aptamer may be identified through a selection process using, e.g., systematic evolution of ligands by exponential enrichment (SELEX) or various directed evolution techniques. See, e.g., Turek, C. and Gold, L., Science 249: 505-10, 1990; Brody E N and Gold L J, Biotechnol. J, 74(1):5-13, 2000; L. Cerchia and V. de Franciscis, Trends Biotechnol., 28: 517-525, 2010; Keefe, A. Nat. Rev. Drug Discov. 9: 537-550, 2010. An aptamer is typically single-stranded (although it may form regions of double-stranded secondary structure through intramolecular complementarity).

An "assay" may encompass any procedure or process of sequence of procedures or processes that may be used to identify or assess something. As used herein, "assess", "assessing", and similar terms encompass characterizing, detecting, determining, measuring, evaluating, estimating, analyzing, testing, etc. In various embodiments the thing being identified or assessed may be, e.g., a gene, gene product, reactant or product of a reaction, a pathway, an agent, a composition, a cell, a cell line, a tumor, a subject, a reagent for use in a composition or method, etc. In some embodiments an assay may be qualitative or may be at least in part quantitative, e.g., it may provide a measurement, which may be expressed numerically. A measurement may be relative or absolute in various embodiments. In some embodiments an assay provides a measurement of a magnitude, concentration, level, amount, intensity, degree of modulation (e.g., reduction or enhancement), activity, or a change in any of the foregoing, etc. A screen may comprise assessing an entity for one or more properties of interest or for its suitability for one or more purposes or applications of interest or may comprise identifying an entity that has one or more properties of interest or that is or may be suitable for one or more purposes or applications of interest. A screen may comprise, e.g., one or more assays, a computer-aided procedure or process, etc. In various embodiments the thing being or to identified or assessed may be, e.g., a gene, gene product, reactant or product of a reaction, a pathway, an agent, a composition, a cell, a cell line, a tumor, a subject, a reagent for use in a composition or method, etc., or may be a sequence, structure, or other information or representation that may be manipulated, analyzed, processed, or displayed using a computer. In some embodiments a screen comprises assessing multiple entities (e.g., multiple agents, e.g., multiple test agents) in a coordinated manner, e.g., under common direction or control. A screen may comprise performing the same or essentially the same assay multiple times, e.g., using multiple different test agents. The assays may be performed using the same assay system (e.g., using the same equipment/instrumentation). The assays may be performed using essentially the same assay composition, differing in the identity of the test agent. The assays may be performed using a predetermined set of test agents, e.g., a library of agents.

"Cellular marker" refers to a molecule (e.g., a protein, RNA, DNA, lipid, carbohydrate) or portion thereof, the level of which in or on a cell (e.g., at least partly exposed at the cell surface) characterizes, indicates, or identifies one or more cell type(s), cell lineage(s), or tissue type(s) or characterizes, indicates, or identifies a particular state (e.g., a diseased or physiological state such as cancerous or normal, a differentiation state, a stem cell state). A level may be reported in a variety of different ways, e.g., high/low; +/−; numerically, etc. The presence, absence, or level of certain cellular marker(s) may indicate a particular physiological or diseased state of a patient, organ, tissue, or cell. It will be understood that multiple cellular markers may be assessed to, e.g., identify or isolate a cell type of interest, diagnose a disease, etc. In some embodiments between 2 and 10 cellular markers may be assessed. A cellular marker present on or at the surface of cells may be referred to as a "cell surface marker". In some embodiments, a cell surface marker is a receptor. For example, a targeting moiety may bind to an extracellular domain of a receptor. In some embodiments, a receptor is a growth factor receptor, hormone receptor, integrin receptor, folate receptor, or transferrin receptor. A cellular marker may be cell type specific. A cell type specific marker is generally expressed or present at a higher level in or on (at the surface of) a particular cell type or cell types than in or on many or most other cell types (e.g., other cell types in the body or in an artificial environment). In some cases a cell type specific marker is present at detectable levels only in or on a particular cell type of interest. However, useful cell type specific markers may not be and often are not absolutely specific for the cell type of interest. A cellular marker, e.g., a cell type specific marker, may be present at levels at least 2-fold or at least 3-fold greater in or on the surface of a particular cell type than in a reference population of cells which may consist, for example, of a mixture containing cells from multiple (e.g., 5-10; 10-20, or more) of different tissues or organs in approximately equal amounts. In some embodiments a cellular marker, e.g., a cell type specific marker, may be present at levels at least 4-5 fold, between 5-10 fold, or more than 10-fold greater than its average expression in a reference population. In some embodiments a cellular marker, e.g., a cell surface marker, is selectively expressed by tumor cells, e.g., is overexpressed by tumor cells as compared with expression by normal cells, e.g., normal cells derived from the same organ and/or cell type. Such a cellular marker may be referred to as a "tumor cellular marker". A tumor marker present on or at the surface of a tumor cell may be referred to as a "tumor cell surface marker". In some embodiments a tumor cell surface marker is a molecule (or portion thereof) that is differentially expressed by at least some tumor cells as compared with non-tumor cells. A useful tumor cell surface marker may be expressed or overexpressed by one or more tumor types or a subset of tumors of one or more tumor types. In some embodiments, a tumor cell surface marker is overexpressed by at least a factor of 1.5 in at least some cells of a tumor, relative to expression by normal cells, e.g., normal cells derived from the same organ and/or cell type, as measured using a suitable assay. Tumor cell surface markers may include, e.g., proteins that are normally produced in very small quantities and are expressed in larger quantities by tumor cells, proteins that are normally produced only in certain stages of development (e.g., prior to birth), proteins whose structure (e.g., sequence or post-translational modification(s)) is modified due to mutation in tumor cells, or normal proteins that are (under normal conditions) sequestered from the immune system. In some embodiments, a tumor cell surface marker is an expression product of a mutated gene, e.g., an oncogene or mutated tumor suppressor gene, an overexpressed or aberrantly expressed cellular protein, or an oncofetal antigen. In general, the level of a cellular marker may be determined using standard techniques such as Northern blotting, in situ hybridization, RT-PCR, sequencing, immunological methods such as immunoblotting, immunohistochemistry, fluorescence detection following staining with fluorescently labeled antibodies (e.g., flow cytometry, fluorescence microscopy), similar methods using non-antibody ligands that specifically bind to the marker, oligonucleotide or cDNA microarray or membrane array, protein microarray analysis, mass spectrometry. A cell surface marker, e.g., a cell type specific cell surface marker or a tumor cell surface marker, may be used to detect or isolate cells or as a target in order to deliver an agent to cells. For example, the agent may be linked to a moiety that binds to a cell surface marker. Suitable binding moieties include, e.g., antibodies or ligands, e.g., small molecules, aptamer, polypeptides.

"Computer-aided" as used herein encompasses methods in which a computer system is used to gather, process, manipulate, display, visualize, receive, transmit, store, or otherwise handle information (e.g., data, results, structures, sequences, etc.). A method may comprise causing the processor of a computer to execute instructions to gather, process, manipulate, display, receive, transmit, or store data or other information. The instructions may be embodied in a computer program product comprising a computer-readable medium. In some embodiments a method comprises transmitting or receiving data or other information over a communication network. A communication network may, for example, comprise one or more intranets or the Internet.

An "effective amount" or "effective dose" of an agent (or composition containing such agent) refers to the amount sufficient to achieve a desired biological and/or pharmacological effect, e.g., when delivered to a cell or organism according to a selected administration form, route, and/or schedule. As will be appreciated by those of ordinary skill in this art, the absolute amount of a particular agent or composition that is effective may vary depending on such factors as the desired biological or pharmacological endpoint, the agent to be delivered, the target tissue, etc. Those of ordinary skill in the art will further understand that an "effective amount" may be contacted with cells or administered in a single dose, or through use of multiple doses, in various embodiments. A biological effect may be, e.g., reducing expression or activity of one or more gene products, reducing activity of a metabolic pathway or reaction, reducing cell proliferation or survival of cells (e.g., tumor cell proliferation or survival), reducing tumor maintenance, size, growth, or progression.

The term "expression" encompasses the processes by which polynucleic acids (e.g., DNA) are transcribed to produce RNA, and (where applicable) RNA transcripts are translated into polypeptides.

The term "gene product" (also referred to herein as "gene expression product" or "expression product") encompasses products resulting from expression of a gene, such as RNA transcribed from a gene and polypeptides arising from translation of such RNA. It will be appreciated that certain gene products may undergo processing or modification, e.g., in a cell. For example, RNA transcripts may be spliced, polyadenylated, etc., prior to mRNA translation, and/or polypeptides may undergo co-translational or post-translational processing such as removal of secretion signal sequences, removal of organelle targeting sequences, or modifications such as phosphorylation, fatty acylation, etc. The term "gene product" encompasses such processed or modified forms. Genomic, mRNA, polypeptide sequences from a variety of species, including human, are known in the art and are available in publicly accessible databases such as those available at the National Center for Biotechnology Information (www.ncbi.nih.gov) or Universal Protein Resource (www.uniprot.org). Exemplary databases include, e.g., GenBank, RefSeq, Gene, UniProtKB/SwissProt, UniProtKB/Trembl, and the like. In general, sequences, e.g., mRNA and polypeptide sequences, in the NCBI Reference Sequence database may be used as gene product sequences for a gene of interest. It will be appreciated that multiple alleles of a gene may exist among individuals of the same species. For example, differences in one or more nucleotides (e.g., up to about 1%, 2%, 3-5% of the nucleotides) of the nucleic acids encoding a particular protein may exist among individuals of a given species. Due to the degeneracy of the genetic code, such variations often do not alter the encoded amino acid sequence, although DNA polymorphisms that lead to changes in the sequence of the encoded proteins can exist. Examples of polymorphic variants can be found in, e.g., the Single Nucleotide Polymorphism Database (db-SNP), available at the NCBI website at www.ncbi.nlm.nih- .gov/projects/SNP/. (Sherry S T, et al. (2001). "dbSNP: the NCBI database of genetic variation". Nucleic Acids Res. 29 (1): 308-311; Kitts A, and Sherry S, (2009). The single nucleotide polymorphism database (dbSNP) of nucleotide sequence variation in The NCBI Handbook [Internet]. McEntyre J, Ostell J, editors. Bethesda (Md.): National Center for Biotechnology Information (US); 2002 (www.ncbi.nlm.nih.gov/bookshelf/br.fcgi?book=handbook&part=ch5). Multiple isoforms of certain proteins may exist, e.g., as a result of alternative RNA splicing or editing. In general, where aspects of this disclosure pertain to a gene or gene product, embodiments pertaining to allelic variants or isoforms are encompassed unless indicated otherwise. Certain embodiments may be directed to particular sequence(s), e.g., particular allele(s) or isoform(s).

"Identity" or "percent identity" is a measure of the extent to which the sequence of two or more nucleic acids or polypeptides is the same. The percent identity between a sequence of interest A and a second sequence B may be computed by aligning the sequences, allowing the introduction of gaps to maximize identity, determining the number of residues (nucleotides or amino acids) that are opposite an identical residue, dividing by the minimum of $TG_A$ and $TG_B$ (here $TG_A$ and $TG_B$ are the sum of the number of residues and internal gap positions in sequences A and B in the alignment), and multiplying by 100. When computing the number of identical residues needed to achieve a particular percent identity, fractions are to be rounded to the nearest whole number. Sequences can be aligned with the use of a variety of computer programs known in the art. For example, computer programs such as BLAST2, BLASTN, BLASTP, Gapped BLAST, etc., may be used to generate alignments and/or to obtain a percent identity. The algorithm of Karlin and Altschul (Karlin and Altschul, Proc. Natl. Acad. Sci. USA 87:22264-2268, 1990) modified as in Karlin and Altschul, Proc. Natl. Acad Sci. USA 90:5873-5877,1993 is incorporated into the NBLAST and XBLAST programs of Altschul et al. (Altschul, et al., J. Mol. Biol. 215:403-410, 1990). In some embodiments, to obtain gapped alignments for comparison purposes, Gapped BLAST is utilized as described in Altschul et al. (Altschul, et al. Nucleic Acids Res. 25: 3389-3402, 1997). When utilizing BLAST and Gapped BLAST programs, the default parameters of the respective programs may be used. See the Web site having URL www.ncbi.nlm.nih.gov and/or McGinnis, S. and Madden, T L, W20-W25 Nucleic Acids Research, 2004, Vol. 32, Web server issue. Other suitable programs include CLUSTALW (Thompson J D, Higgins D G, Gibson T J, Nuc Ac Res, 22:4673-4680, 1994) and GAP (GCG Version 9.1; which implements the Needleman & Wunsch, 1970 algorithm (Needleman S B, Wunsch C D, J Mol Biol, 48:443-453, 1970.) Percent identity may be evaluated over a window of evaluation. In some embodiments a window of evaluation may have a length of at least 10%, 15%, 20%, 25%, 30%, 35%, 40%, 45%, 50%, 55%, 60%, 65%, 70%, 75%, 80%, 85%, 90%, 95%, 96%, 97%, 98%, 99%, or more, e.g., 100%, of the length of the shortest of the sequences being compared. In some embodiments a window of evaluation is at least 100; 200; 300; 400; 500; 600; 700; 800; 900; 1,000; 1,200; 1,500; 2,000; 2,500; 3,000; 3,500; 4,000; 4,500; or 5,000 amino acids. In some embodiments no more than 20%, 10%, 5%, or 1% of positions in either sequence or in both sequences over a window of evaluation are occupied by a gap. In some embodiments no more than 20%, 10%, 5%, or 1% of positions in either sequence or in both sequences are occupied by a gap.

"Inhibit" may be used interchangeably with terms such as "suppress", "decrease", "reduce" and like terms, as appropriate in the context. It will be understood that the extent of inhibition may vary. For example, inhibition may refer to a reduction of the relevant level by at least about 5%, 10%, 15%, 20%, 25%, 30%, 35%, 40%, 45%, 50%, 55%, 60%, 65%, 70%, 75%, 80%, 85%, 90%, 95%, 96%, 97%, 98%, or 99%. In some embodiments inhibition refers to a decrease of 100%, e.g., to background levels or undetectable levels. In some embodiments inhibition is statistically significant.

"Isolated" means 1) separated from at least some of the components with which it is usually associated in nature; 2) prepared or purified by a process that involves the hand of man; and/or 3) not occurring in nature, e.g., present in an artificial environment.

"Nucleic acid" is used interchangeably with "polynucleotide" and encompasses polymers of nucleotides. "Oligonucleotide" refers to a relatively short nucleic acid, e.g., typically between about 4 and about 100 nucleotides (nt) long, e.g., between 8-60 nt or between 10-40 nt long. Nucleotides include, e.g., ribonucleotides or deoxyribonucleotides. In some embodiments a nucleic acid comprises or consists of DNA or RNA. In some embodiments a nucleic acid comprises or includes only standard nucleobases (often referred to as "bases"). The standard bases are cytosine, guanine, adenine (which are found in DNA and RNA), thymine (which is found in DNA) and uracil (which is found in RNA), abbreviated as C, G, A, T, and U, respectively. In some embodiments a nucleic acid may comprise one or more non-standard nucleobases, which may be naturally occurring or non-naturally occurring (i.e., artificial; not found in nature) in various embodiments. In some embodiments a nucleic acid may comprise chemically or biologically modified bases (e.g., alkylated (e.g., methylated) bases), modified sugars (e.g., 2'-O-alkyribose (e.g., 2'-O methylribose), 2'-fluororibose, arabinose, or hexose), modified phosphate groups (e.g., phosphorothioates or 5'-N-phosphoramidite linkages). In some embodiments a nucleic acid comprises subunits (residues), e.g., nucleotides, that are linked by phosphodiester bonds. In some embodiments, at least some subunits of a nucleic acid are linked by a non-phosphodiester bond or other backbone structure. In some embodiments, a nucleic acid comprises a locked nucleic acid, morpholino, or peptide nucleic acid. A nucleic acid may be linear or circular in various embodiments. A nucleic acid may be single-stranded, double-stranded, or partially double-stranded in various embodiments. An at least partially double-stranded nucleic acid may be blunt-ended or may have one or more overhangs, e.g., 5' and/or 3' overhang(s). Nucleic acid modifications (e.g., base, sugar, and/or backbone modifications), non-standard nucleotides or nucleosides, etc., such as those known in the art as being useful in the context of RNA interference (RNAi), aptamer, or antisense-based molecules for research or therapeutic purposes may be incorporated in various embodiments. Such modifications may, for example, increase stability (e.g., by reducing sensitivity to cleavage by nucleases), decrease clearance in vivo, increase cell uptake, or confer other properties that improve the potency, efficacy, specificity, or otherwise render the nucleic acid more suitable for an intended use. Various non-limiting examples of nucleic acid modifications are described in, e.g., Deleavey G F, et al., Chemical modification of siRNA. Curr. Protoc. Nucleic Acid Chem. 2009; 39:16.3.1-16.3.22; Crooke, S T (ed.) Antisense drug technology: principles, strategies, and applications, Boca Raton: CRC Press, 2008; Kurreck, J. (ed.) Therapeutic oligonucleotides, RSC biomolecular sciences.

Cambridge: Royal Society of Chemistry, 2008; U.S. Pat. Nos. 4,469,863; 5,536,821; 5,541,306; 5,637,683; 5,637,684; 5,700,922; 5,717,083; 5,719,262; 5,739,308; 5,773,601; 5,886,165; 5,929, 226; 5,977,296; 6,140,482; 6,455,308 and/or in PCT application publications WO 00/56746 and WO 01/14398. Different modifications may be used in the two strands of a double-stranded nucleic acid. A nucleic acid may be modified uniformly or on only a portion thereof and/or may contain multiple different modifications.

A "polypeptide" refers to a polymer of amino acids linked by peptide bonds. A protein is a molecule comprising one or more polypeptides. A peptide is a relatively short polypeptide, typically between about 2 and 100 amino acids (aa) in length, e.g., between 4 and 60 aa; between 8 and 40 aa; between 10 and 30 aa. The terms "protein", "polypeptide", and "peptide" may be used interchangeably. In general, a polypeptide may contain only standard amino acids or may comprise one or more non-standard amino acids (which may be naturally occurring or non-naturally occurring amino acids) and/or amino acid analogs in various embodiments. A "standard amino acid" is any of the 20 L-amino acids that are commonly utilized in the synthesis of proteins by mammals and are encoded by the genetic code. A "non-standard amino acid" is an amino acid that is not commonly utilized in the synthesis of proteins by mammals. Non-standard amino acids include naturally occurring amino acids (other than the 20 standard amino acids) and non-naturally occurring amino acids. In some embodiments, a non-standard, naturally occurring amino acid is found in mammals. For example, ornithine, citrulline, and homocysteine are naturally occurring non-standard amino acids that have important roles in mammalian metabolism. Exemplary non-standard amino acids include, e.g., singly or multiply halogenated (e.g., fluorinated) amino acids, D-amino acids, homo-amino acids, N-alkyl amino acids (other than proline), dehydroamino acids, aromatic amino acids (other than histidine, phenylalanine, tyrosine and tryptophan), and $\alpha,\alpha$ disubstituted amino acids. An amino acid, e.g., one or more of the amino acids in a polypeptide, may be modified, for example, by addition, e.g., covalent linkage, of a moiety such as an alkyl group, an alkanoyl group, a carbohydrate group, a phosphate group, a lipid, a polysaccharide, a halogen, a linker for conjugation, a protecting group, etc. Modifications may occur anywhere in a polypeptide, e.g., the peptide backbone, the amino acid side-chains and the amino or carboxyl termini. A given polypeptide may contain many types of modifications. Polypeptides may be branched or they may be cyclic, with or without branching. Polypeptides may be conjugated with, encapsulated by, or embedded within a polymer or polymeric matrix, dendrimer, nanoparticle, microparticle, liposome, or the like. Modification may occur prior to or after an amino acid is incorporated into a polypeptide in various embodiments. Polypeptides may, for example, be purified from natural sources, produced in vitro or in vivo in suitable expression systems using recombinant DNA technology (e.g., by recombinant host cells or in transgenic animals or plants), synthesized through chemical means such as conventional solid phase peptide synthesis, and/or methods involving chemical ligation of synthesized peptides (see, e.g., Kent, S., J Pept Sci., 9(9):574-93, 2003 or U.S. Pub. No. 20040115774), or any combination of the foregoing.

As used herein, the term "purified" refers to agents that have been separated from most of the components with which they are associated in nature or when originally generated. In general, such purification involves action of the hand of man. Purified agents may be partially purified, substantially purified, or pure. Such agents may be, for example, at least 50%, 60%, 70%, 75%, 80%, 85%, 90%, 95%, 96%, 97%, 98%, 99%, or more than 99% pure. In some embodiments, a nucleic acid, polypeptide, or small molecule is purified such that it constitutes at least 75%, 80%, 85%, 90%, 95%, 96%, 97%, 98%, 99%, or more, of the total nucleic acid, polypeptide, or small molecule material, respectively, present in a preparation. In some embodiments, an organic substance, e.g., a nucleic acid, polypeptide, or small molecule, is purified such that it constitutes at least 75%, 80%, 85%, 90%, 95%, 96%, 97%, 98%, 99%, or more, of the total organic material present in a preparation. Purity may be based on, e.g., dry weight, size of peaks on a chromatography tracing (GC, HPLC, etc.), molecular abundance, electrophoretic methods, intensity of bands on a gel, spectroscopic data (e.g., NMR), elemental analysis, high throughput sequencing, mass spectrometry, or any art-accepted quantification method. In some embodiments, water, buffer substances, ions, and/or small molecules (e.g., synthetic precursors such as nucleotides or amino acids), can optionally be present in a purified preparation. A purified agent may be prepared by separating it from other substances (e.g., other cellular materials), or by producing it in such a manner to achieve a desired degree of purity. In some embodiments "partially purified" with respect to a molecule produced by a cell means that a molecule produced by a cell is no longer present within the cell, e.g., the cell has been lysed and, optionally, at least some of the cellular material (e.g., cell wall, cell membrane(s), cell organelle(s)) has been removed and/or the molecule has been separated or segregated from at least some molecules of the same type (protein, RNA, DNA, etc.) that were present in the lysate.

The term "RNA interference" (RNAi) encompasses processes in which a molecular complex known as an RNA-induced silencing complex (RISC) silences or "knocks down" gene expression in a sequence-specific manner in, e.g., eukaryotic cells, e.g., vertebrate cells, or in an appropriate in vitro system. RISC may incorporate a short nucleic acid strand (e.g., about 16-about 30 nucleotides (nt) in length) that pairs with and directs or "guides" sequence-specific degradation or translational repression of RNA (e.g., mRNA) to which the strand has complementarity. The short nucleic acid strand may be referred to as a "guide strand" or "antisense strand". An RNA strand to which the guide strand has complementarity may be referred to as a "target RNA". A guide strand may initially become associated with RISC components (in a complex sometimes termed the RISC loading complex) as part of a short double-stranded RNA (dsRNA), e.g., a short interfering RNA (siRNA). The other strand of the short dsRNA may be referred to as a "passenger strand" or "sense strand". The complementarity of the structure formed by hybridization of a target RNA and the guide strand may be such that the strand can (i) guide cleavage of the target RNA in the RNA-induced silencing complex (RISC) and/or (ii) cause translational repression of the target RNA. Reduction of expression due to RNAi may be essentially complete (e.g., the amount of a gene product is reduced to background levels) or may be less than complete in various embodiments. For example, mRNA and/or protein level may be reduced by 50%, 60%, 70%, 75%, 80%, 85%, 90%, 95%, or more, in various embodiments. As known in the art, the complementarity between the guide strand and a target RNA need not be perfect (100%) but need only be sufficient to result in inhibition of gene expression. For example, in some embodiments 1, 2, 3, 4, 5, or more nucleotides of a guide strand may not be matched to a target RNA. "Not matched" or "unmatched"

refers to a nucleotide that is mismatched (not complementary to the nucleotide located opposite it in a duplex, i.e., wherein Watson-Crick base pairing does not take place) or forms at least part of a bulge. Examples of mismatches include, without limitation, an A opposite a G or A, a C opposite an A or C, a U opposite a C or U, a G opposite a G. A bulge refers to a sequence of one or more nucleotides in a strand within a generally duplex region that are not located opposite to nucleotide(s) in the other strand. "Partly complementary" refers to less than perfect complementarity. In some embodiments a guide strand has at least about 80%, 85%, or 90%, e.g., least about 91%, 92%, 93%, 94%, 95%, 96%, 97%, 98%, 99%, or 100% sequence complementarity to a target RNA over a continuous stretch of at least about 15 nt, e.g., between 15 nt and 30 nt, between 17 nt and 29 nt, between 18 nt and 25 nt, between 19 nt and 23 nt, of the target RNA. In some embodiments at least the seed region of a guide strand (the nucleotides in positions 2-7 or 2-8 of the guide strand) is perfectly complementary to a target RNA. In some embodiments, a guide strand and a target RNA sequence may form a duplex that contains no more than 1, 2, 3, or 4 mismatched or bulging nucleotides over a continuous stretch of at least 10 nt, e.g., between 10-30 nt. In some embodiments a guide strand and a target RNA sequence may form a duplex that contains no more than 1, 2, 3, 4, 5, or 6 mismatched or bulging nucleotides over a continuous stretch of at least 12 nt, e.g., between 10-30 nt. In some embodiments, a guide strand and a target RNA sequence may form a duplex that contains no more than 1, 2, 3, 4, 5, 6, 7, or 8 mismatched or bulging nts over a continuous stretch of at least 15 nt, e.g., between 10-30 nt. In some embodiments, a guide strand and a target RNA sequence may form a duplex that contains no mismatched or bulging nucleotides over a continuous stretch of at least 10 nt, e.g., between 10-30 nt. In some embodiments, between 10-30 nt is 10, 11, 12, 13, 14, 15, 16, 17, 18, 19, 20, 21, 22, 23, 24, 25, 26, 27, 28, 29, or 30 nt.

As used herein, the term "RNAi agent" encompasses nucleic acids that can be used to achieve RNAi in eukaryotic cells. Short interfering RNA (siRNA), short hairpin RNA (shRNA), and microRNA (miRNA) are examples of RNAi agents. siRNAs typically comprise two separate nucleic acid strands that are hybridized to each other to form a structure that contains a double stranded (duplex) portion at least 15 nt in length, e.g., about 15-about 30 nt long, e.g., between 17-27 nt long, e.g., between 18-25 nt long, e.g., between 19-23 nt long, e.g., 15, 16, 17, 18, 19, 20, 21, 22, 23, 24, 25, 26, 27, 28, 29, or 30 nucleotides. In some embodiments the strands of an siRNA are perfectly complementary to each other within the duplex portion. In some embodiments the duplex portion may contain one or more unmatched nucleotides, e.g., one or more mismatched (non-complementary) nucleotide pairs or bulged nucleotides. In some embodiments either or both strands of an siRNA may contain up to about 1, 2, 3, or 4 unmatched nucleotides within the duplex portion. In some embodiments a strand may have a length of between 15-35 nt, e.g., between 17-29 nt, e.g., 19-25 nt, e.g., 21-23 nt. Strands may be equal in length or may have different lengths in various embodiments. In some embodiments strands may differ by between 1-10 nt in length. A strand may have a 5' phosphate group and/or a 3' hydroxyl (—OH) group. Either or both strands of an siRNA may comprise a 3' overhang of, e.g., about 1-10 nt (e.g., 1-5 nt, e.g., 2 nt). Overhangs may be the same length or different in lengths in various embodiments. In some embodiments an overhang may comprise or consist of deoxyribonucleotides, ribonucleotides, or modified nucleotides or modified ribonucleotides such as 2'-O-methylated nucleotides, or 2'-O-methyl-uridine. An overhang may be perfectly complementary, partly complementary, or not complementary to a target RNA in a hybrid formed by the guide strand and the target RNA in various embodiments.

shRNAs are nucleic acid molecules that comprise a stem-loop structure and a length typically between about 40-150 nt, e.g., about 50-100 nt, e.g., 60-80 nt. A "stem-loop structure" (also referred to as a "hairpin" structure) refers to a nucleic acid having a secondary structure that includes a region of nucleotides which are known or predicted to form a double strand (stem portion; duplex) that is linked on one side by a region of (usually) predominantly single-stranded nucleotides (loop portion). Such structures are well known in the art and the term is used consistently with its meaning in the art. A guide strand sequence may be positioned in either arm of the stem, i.e., 5' with respect to the loop or 3' with respect to the loop in various embodiments. As is known in the art, the stem structure does not require exact base-pairing (perfect complementarity). Thus, the stem may include one or more unmatched residues or the base-pairing may be exact, i.e., it may not include any mismatches or bulges. In some embodiments the stem is between 15-30 nt, e.g., between 17-29 nt, e.g., 19-25 nt. In some embodiments the stem is between15-19 nt. In some embodiments the stem is between 19-30 nt. The primary sequence and number of nucleotides within the loop may vary. Examples of loop sequences include, e.g., UGGU; ACUCGAGA; UUCAAGAGA. In some embodiments a loop sequence found in a naturally occurring miRNA precursor molecule (e.g., a pre-miRNA) may be used. In some embodiments a loop sequence may be absent (in which case the termini of the duplex portion may be directly linked). In some embodiments a loop sequence may be at least partly self-complementary. In some embodiments the loop is between 1 and 20 nt in length, e.g., 1-15 nt, e.g., 4-9 nt. The shRNA structure may comprise a 5' or 3' overhang. As known in the art, an shRNA may undergo intracellular processing, e.g., by the ribonuclease (RNase) III family enzyme known as Dicer, to remove the loop and generate an siRNA.

Mature endogenous miRNAs are short (typically 18-24 nt, e.g., about 22 nt), single-stranded RNAs that are generated by intracellular processing from larger, endogenously encoded precursor RNA molecules termed miRNA precursors (see, e.g., Bartel, D., MicroRNAs: genomics, biogenesis, mechanism, and function. Cell. 116(2):281-97 (2004); Bartel D P. MicroRNAs: target recognition and regulatory functions. Cell. 136(2):215-33 (2009); Winter, J., et al., Nature Cell Biology 11: 228-234 (2009). Artificial miRNA may be designed to take advantage of the endogenous RNAi pathway in order to silence a target RNA of interest.

An RNAi agent that contains a strand sufficiently complementary to an RNA of interest so as to result in reduced expression of the RNA of interest (e.g., as a result of degradation or repression of translation of the RNA) in a cell or in an in vitro system capable of mediating RNAi and/or that comprises a sequence that is at least 80%, 90%, 95%, or more (e.g., 100%) complementary to a sequence comprising at least 10, 12, 15, 17, or 19 consecutive nucleotides of an RNA of interest may be referred to as being "targeted to" the RNA of interest. An RNAi agent targeted to an RNA transcript may also considered to be targeted to a gene from which the transcript is transcribed.

In some embodiments an RNAi agent is a vector (e.g., an expression vector) suitable for causing intracellular expression of one or more transcripts that give rise to a siRNA, shRNA, or miRNA in the cell. Such a vector may be referred to as an "RNAi vector". An RNAi vector may comprise a template that, when transcribed, yields transcripts that may form a siRNA (e.g., as two separate strands that hybridize to each other), shRNA, or miRNA precursor (e.g., pri-miRNA or pre-mRNA).

An RNAi agent may be produced in any of variety of ways in various embodiments. For example, nucleic acid strands may be chemically synthesized (e.g., using standard nucleic acid synthesis techniques) or may be produced in cells or using an in vitro transcription system. Strands may be allowed to hybridize (anneal) in an appropriate liquid composition (sometimes termed an "annealing buffer"). An RNAi vector may be produced using standard recombinant nucleic acid techniques.

A "sample" may be any biological specimen that contains cells, tissue, or cellular material (e.g., material derived from cells, such as a cell lysate or fraction thereof). A sample may be obtained from (i.e., originates from, was initiallyremoved from) a subject. Methods of obtaining samples are known in the art and include, e.g., tissue biopsy, such as excisional biopsy, incisional biopy, or core biopsy; fine needle aspiration biopsy; brushings; lavage; or collecting body fluids that may contain cells, such as blood, sputum, lymph, mucus, saliva, or urine. In some embodiments a sample contains at least some intact cells at the time it is removed from a subject. In some embodiments a sample retains at least some of the microarchitecture of a tissue from which it was removed. A sample may be subjected to one or more processing steps after having been obtained from a subject and/or may be split into one or more portions. The term "sample" encompasses processed samples, portions of samples, etc., and such samples are considered to have been obtained from the subject from whom the initial sample was removed. In some embodiments a sample may be obtained from an individual who has been diagnosed with or is suspected of having a tumor, e.g., a brain tumor. A tumor sample is a sample obtained from or comprising tumor cells or a tumor. A tumor sample may have been obtained from a tumor prior to or after removal of the tumor from a subject. A sample, e.g., a sample used in a method or composition disclosed herein, may have been procured directly from a subject, or indirectly, e.g., by receiving the sample from one or more persons who procured the sample directly from the subject, e.g., by performing a biopsy, surgery, or other procedure on the subject.

A "small molecule" as used herein, is an organic molecule that is less than about 2 kilodaltons (kDa) in mass. In some embodiments, the small molecule is less than about 1.5 kDa, or less than about 1 kDa. In some embodiments, the small molecule is less than about 800 daltons (Da), 600 Da, 500 Da, 400 Da, 300 Da, 200 Da, or 100 Da. Often, a small molecule has a mass of at least 50 Da. In some embodiments, a small molecule is non-polymeric. In some embodiments, a small molecule is not an amino acid. In some embodiments, a small molecule is not a nucleotide. In some embodiments, a small molecule is not a saccharide. In some embodiments, a small molecule contains multiple carbon-carbon bonds and can comprise one or more heteroatoms and/or one or more functional groups important for structural interaction with proteins (e.g., hydrogen bonding), e.g., an amine, carbonyl, hydroxyl, or carboxyl group, and in some embodiments at least two functional groups. Small molecules often comprise one or more cyclic carbon or heterocyclic structures and/or aromatic or polyaromatic structures, optionally substituted with one or more of the above functional groups.

A "subject" may be any vertebrate organism in various embodiments. A subject may be individual to whom an agent is administered, e.g., for experimental, diagnostic, and/or therapeutic purposes or from whom a sample is obtained or on whom a procedure is performed. In some embodiments a subject is a mammal, e.g. a human, non-human primate, rodent (e.g., mouse, rat, rabbit), ungulate (e.g., ovine, bovine, equine, caprine species), canine, or feline. In some embodiments, a subject is an adult. For purposes hereof a human at least18 years of age is considered an adult.

"Treat", "treating" and similar terms refer to providing medical and/or surgical management of a subject. Treatment may include, but is not limited to, administering an agent or composition (e.g., a pharmaceutical composition) to a subject. Treatment is typically undertaken in an effort to alter the course of a disease (which term is used to indicate any disease, disorder, or undesirable condition warranting therapy) in a manner beneficial to the subject. The effect of treatment may include reversing, alleviating, reducing severity of, delaying the onset of, curing, inhibiting the progression of, and/or reducing the likelihood of occurrence or recurrence of the disease or one or more symptoms or manifestations of the disease. A therapeutic agent may be administered to a subject who has a disease or is at increased risk of developing a disease relative to a member of the general population. In some embodiments a therapeutic agent may be administered to a subject who has had a disease but no longer shows evidence of the disease. The agent may be administered e.g., to reduce the likelihood of recurrence of evident disease. A therapeutic agent may be administered prophylactically, i.e., before development of any symptom or manifestation of a disease. "Prophylactic treatment" refers to providing medical and/or surgical management to a subject who has not developed a disease or does not show eveidence of a disease in order, e.g., to reduce the likelihood that the disease will occur or to reduce the severity of the disease should it occur. The subject may have been identified as being at risk of developing the disease (e.g., at increased risk relative to the general population or as having a risk factor that increases the likelihood of developing the disease.

A "variant" of a particular polypeptide or polynucleotide has one or more alterations (e.g., additions, substitutions, and/or deletions, which may be referred to collectively as "mutations") with respect to the polypeptide or polynucleotide, which may be referred to as the "original polypeptide" or "original polynucleotide", respectively. An addition may be an insertion or may be at either terminus. A variant may be shorter or longer than the original polypeptide or polynucleotide. The term "variant" encompasses "fragments". A "fragment" is a continuous portion of a polypeptide or polynucleotide that is shorter than the original polypeptide. In some embodiments a variant comprises or consists of a fragment. In some embodiments a fragment or variant is at least 20%, 30%, 40%, 50%, 60%, 70%, 80%, 90%, 95%, 96%, 97%, 98%, 99%, or more as long as the original polypeptide or polynucleotide. A fragment may be an N-terminal, C-terminal, or internal fragment. In some embodiments a variant polypeptide comprises or consists of at least one domain of an original polypeptide. In some embodiments a variant polynucleotide hybridizes to an original polynucleotide under stringent conditions, e.g., high stringency conditions, for sequences of the length of the original polypeptide. In some embodiments a variant polypeptide or polynucleotide comprises or consists of a polypeptide or polynucleotide that is at least 50%, 60%, 70%, 80%, 90%, 95%, 96%, 97%, 98%, 99%, or more identical in sequence to the original polypeptide or polynucleotide over at least 20%, 30%, 40%, 50%, 60%, 70%, 80%, 90%, 95%, 96%, 97%, 98%, 99%, or 100% of the original polypeptide or polynucleotide. In some embodiments a variant polypeptide comprises or consists of a polypeptide that is at least 50%, 60%, 70%, 80%, 90%, 95%, 96%, 97%, 98%, 99%, or more identical in sequence to the original polypeptide over at least 20%, 30%, 40%, 50%, 60%, 70%, 80%, 90%, 95%, 96%, 97%, 98%, 99%, or 100% of the original polypeptide, with the proviso that, for purposes of computing percent identity, a conservative amino acid substitution is considered identical to the amino acid it replaces. In some embodiments a variant polypeptide comprises or consists of a polypeptide that is at least 50%, 60%, 70%, 80%, 90%, 95%, 96%, 97%, 98%, 99%, or more identical to the original polypeptide over at least 20%, 30%, 40%, 50%, 60%, 70%, 80%, 90%, 95%, 96%, 97%, 98%, 99%, or 100% of the original polypeptide, with the proviso that any one or more amino acid substitutions (up to the total number of such substitutions) may be restricted to conservative substitutions. In some embodiments a percent identity is measured over at least 100; 200; 300; 400; 500; 600; 700; 800; 900; 1,000; 1,200; 1,500; 2,000; 2,500; 3,000; 3,500; 4,000; 4,500; or 5,000 amino acids. In some embodiments the sequence of a variant polypeptide comprises or consists of a sequence that has N amino acid differences with respect to an original sequence, wherein N is any integer between 1 and 10 or between 1 and 20 or any integer up to 1%, 2%, 5%, or 10% of the number of amino acids in the original polypeptide, where an "amino acid difference" refers to a substitution, insertion, or deletion of an amino acid. In some embodiments a difference is a conservative substitution. Conservative substitutions may be made, e.g., on the basis of similarity in side chain size, polarity, charge, solubility, hydrophobicity, hydrophilicity and/or the amphipathic nature of the residues involved. In some embodiments, conservative substitutions may be made according to Table A, wherein amino acids in the same block in the second column and in the same line in the third column may be substituted for one another other in a conservative substitution. Certain conservative substitutions are substituting an amino acid in one row of the third column corresponding to a block in the second column with an amino acid from another row of the third column within the same block in the second column.

TABLE A

| Aliphatic | Non-polar | G A P |
| --- | --- | --- |
| | | I L V |
| | Polar - uncharged | C S T M |
| | | N Q |
| | Polar - charged | D E |
| | | K R |
| Aromatic | | H F W Y |

In some embodiments, proline (P) is considered to be in an individual group. In some embodiments, cysteine (C) is considered to be in an individual group. In some embodiments, proline (P) and cysteine (C) are each considered to be in an individual group.

In some embodiments a variant is a functional variant, i.e., the variant at least in part retains at least one activity of the original polypeptide or polynucleotide. In some embodiments a variant at least in part retains more than one or substantially all known biologically significant activities of the original polypeptide or polynucleotide. An activity may be, e.g., a catalytic activity, binding activity, ability to perform or participate in a biological function or process, etc. In some embodiments an activity of a variant may be at least 10%, 20%, 30%, 40%, 50%, 60%, 70%, 80%, 90%, 95%, or more, of the activity of the original polypeptide or polynucleotide, up to approximately 100%, approximately 125%, or approximately 150% of the activity of the original polypeptide or polynucleotide, in various embodiments. In some embodiments a variant, e.g., a functional variant, comprises or consists of a polypeptide at least 95%, 96%, 97%, 98%, 99%. 99.5% or 100% identical to an original polypeptide or polynucleotide over at least 70%, 75%, 80%, 85%, 90%, 95%, 96%, 97%, 98%, or 99% or 100% of the original polypeptide or polynucleotide. In some embodiments an alteration, e.g., a substitution or deletion, e.g., in a functional variant, does not alter or delete an amino acid or nucleotide that is known or predicted to be important for an activity, e.g., a known or predicted catalytic residue or residue involved in binding a substrate or cofactor. In some embodiments nucleotide(s), amino acid(s), or region(s) exhibiting lower degrees of conservation across species as compared with other amino acids or regions may be selected for alteration. As will be understood, variants can be created by introducing one or more nucleotide alterations, e.g., one or more substitution(s), addition(s_and/or deletion(s) into a nucleotide sequence encoding a polypeptide, such that one or more amino acid alterations, e.g., substitution(s), addition(s) and/or deletion(s) are introduced into the encoded polypeptide. Alterations can be introduced by standard techniques, such as site-directed mutagenesis, PCR-mediated mutagenesis, etc. Variants may be tested in one or more suitable assays to assess activity.

A "vector" may be any of a number of nucleic acid molecules or viruses or portions thereof that are capable of mediating entry of, e.g., transferring, transporting, etc., a nucleic acid of interest between different genetic environments or into a cell. The nucleic acid of interest may be linked to, e.g., inserted into, the vector using, e.g., restriction and ligation. Vectors include, for example, DNA or RNA plasmids, cosmids, naturally occurring or modified viral genomes or portions thereof, nucleic acids that can be packaged into viral capsids, mini-chromosomes, artificial chromosomes, etc. Plasmid vectors typically include an origin of replication (e.g., for replication in prokaryotic cells). A plasmid may include part or all of a viral genome (e.g., a viral promoter, enhancer, processing or packaging signals, and/or sequences sufficient to give rise to a nucleic acid that can be integrated into the host cell genome and/or to give rise to infectious virus). Viruses or portions thereof that can be used to introduce nucleic acids into cells may be referred to as viral vectors. Viral vectors include, e.g., adenoviruses, adeno-associated viruses, retroviruses (e.g., lentiviruses), vaccinia virus and other poxviruses, herpesviruses (e.g., herpes simplex virus), and others. Viral vectors may or may not contain sufficient viral genetic information for production of infectious virus when introduced into host cells, i.e., viral vectors may be replication-competent or replication-defective. In some embodiments, e.g., where sufficient information for production of infectious virus is lacking, it may be supplied by a host cell or by another vector introduced into the cell, e.g., if production of virus is desired. In some embodiments such information is not supplied, e.g., if production of virus is not desired. A nucleic acid to be transferred may be incorporated into a naturally occurring or modified viral genome or a portion thereof or may be present within a viral capsid as a separate nucleic acid molecule. A vector may contain one or more nucleic acids encoding a marker suitable for identifying and/or selecting cells that have taken up the vector. Markers include, for example, various proteins that increase or decrease either resistance or sensitivity to antibiotics or other agents (e.g., a protein that confers resistance to an antibiotic such as puromycin, hygromycin or blasticidin), enzymes whose activities are detectable by assays known in the art (e.g., β-galactosidase or alkaline phosphatase), and proteins or RNAs that detectably affect the phenotype of cells that express them (e.g., fluorescent proteins). Vectors often include one or more appropriately positioned sites for restriction enzymes, which may be used to facilitate insertion into the vector of a nucleic acid, e.g., a nucleic acid to be expressed. An expression vector is a vector into which a desired nucleic acid has been inserted or may be inserted such that it is operably linked to regulatory elements (also termed "regulatory sequences", "expression control elements", or "expression control sequences") and may be expressed as an RNA transcript (e.g., an mRNA that can be translated into protein or a noncoding RNA such as an shRNA or miRNA precursor). Expression vectors include regulatory sequence(s), e.g., expression control sequences, sufficient to direct transcription of an operably linked nucleic acid under at least some conditions; other elements required or helpful for expression may be supplied by, e.g., the host cell or by an in vitro expression system. Such regulatory sequences typically include a promoter and may include enhancer sequences or upstream activator sequences. In some embodiments a vector may include sequences that encode a 5' untranslated region and/or a 3' untranslated region, which may comprise a cleavage and/or polyadenylation signal. In general, regulatory elements may be contained in a vector prior to insertion of a nucleic acid whose expression is desired or may be contained in an inserted nucleic acid or may be inserted into a vector following insertion of a nucleic acid whose expression is desired. As used herein, a nucleic acid and regulatory element(s) are said to be "operably linked" when they are covalently linked so as to place the expression or transcription of the nucleic acid under the influence or control of the regulatory element(s). For example, a promoter region would be operably linked to a nucleic acid if the promoter region were capable of effecting transcription of that nucleic acid. One of ordinary skill in the art will be aware that the precise nature of the regulatory sequences useful for gene expression may vary between species or cell types, but may in general include, as appropriate, sequences involved with the initiation of transcription, RNA processing, or initiation of translation. The choice and design of an appropriate vector and regulatory element(s) is within the ability and discretion of one of ordinary skill in the art. For example, one of skill in the art will select an appropriate promoter (or other expression control sequences) for expression in a desired species (e.g., a mammalian species) or cell type. A vector may contain a promoter capable of directing expression in mammalian cells, such as a suitable viral promoter, e.g., from a cytomegalovirus (CMV), retrovirus, simian virus (e.g., SV40), papilloma virus, herpes virus or other virus that infects mammalian cells, or a mammalian promoter from, e.g., a gene such as EF1alpha, ubiquitin (e.g., ubiquitin B or C), globin, actin, phosphoglycerate kinase (PGK), etc., or a composite promoter such as a CAG promoter (combination of the CMV early enhancer element and chicken beta-actin promoter). In some embodiments a human promoter may be used. In some embodiments, a promoter that ordinarily directs transcription by a eukaryotic RNA polymerase I (a "pol I promoter"), e.g., (a U6, H1, 7SK or tRNA promoter or a functional variant thereof) may be used. In some embodiments, a promoter that ordinarily directs transcription by a eukaryotic RNA polymerase II (a "pol II promoter") or a functional variant thereof is used. In some embodiments, a promoter that ordinarily directs transcription by a eukaryotic RNA polymerase III (a "pol III promoter"), e.g., a promoter for transcription of ribosomal RNA (other than 5S rRNA) or a functional variant thereof is used. One of ordinary skill in the art will select an appropriate promoter for directing transcription of a sequence of interest. Examples of expression vectors that may be used in mammalian cells include, e.g., the pcDNA vector series, pSV2 vector series, pCMV vector series, pRSV vector series, pEF1 vector series, Gateway® vectors, etc. Examples of virus vectors that may be used in mammalian cells include, e.g., adenoviruses, adeno-associated viruses, poxviruses such as vaccinia viruses and attenuated poxviruses, retroviruses (e.g., lentiviruses), Semliki Forest virus, Sindbis virus, etc. In some embodiments, regulatable (e.g., inducible or repressible) expression control element(s), e.g., a regulatable promoter, is/are used so that expression can be regulated, e.g., turned on or increased or turned off or decreased. For example, the tetracycline-regulatable gene expression system (Gossen & Bujard, Proc. Natl. Acad. Sci. 89:5547-5551, 1992) or variants thereof (see, e.g., Allen, N, et al. (2000) Mouse Genetics and Transgenics: 259-263; Urlinger, S, et al. (2000). Proc. Natl. Acad. Sci. U.S.A. 97 (14): 7963-8; Zhou, X., et al (2006). Gene Ther. 13 (19): 1382-1390 for examples) can be employed to provide inducible or repressible expression. Other inducible/repressible systems may be used in various embodiments. For example, expression control elements that can be regulated by small molecules such as artificial or naturally occurring hormone receptor ligands (e.g., steroid receptor ligands such as naturally occurring or synthetic estrogen receptor or glucocorticoid receptor ligands), tetracycline or analogs thereof, metal-regulated systems (e.g., metallothionein promoter) may be used in certain embodiments. In some embodiments, tissue-specific or cell type specific regulatory element(s) may be used, e.g., in order to direct expression in one or more selected tissues or cell types. In some embodiments a vector may comprise a polynucleotide sequence that encodes a polypeptide, wherein the polynucleotide sequence is positioned in frame with a nucleic acid inserted into the vector so that an N- or C-terminal fusion is created. In some embodiments the polypeptide encoded by the polynucleotide sequence may be a targeting peptide. A targeting peptide may comprise a signal sequence (which directs secretion of a protein) or a sequence that directs the expressed protein to a specific organelle or location in the cell such as the nucleus or mitochondria. In some embodiments the polypeptide comprises a tag. A tag may be useful to facilitate detection and/or purification of a protein that contains it. Examples of tags include polyhistidine-tag (e.g., 6×-His tag), glutathione-S-transferase, maltose binding protein, NUS tag, SNUT tag, Strep tag, epitope tags such as V5, HA, Myc, or FLAG. In some embodiments a protease cleavage site is located in the region between the protein encoded by the inserted nucleic acid and the polypeptide, allowing the polypeptide to be removed by exposure to the protease.

For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. General principles of organic chemistry, as well as specific functional moieties and reactivity, are described in, e.g., Organic Chemistry, Thomas Sorrell, University Science Books, Sausalito: 1999, "March's Advanced Organic Chemistry", 5th. Ed. Smith, M. B. and March, J., John Wiley & Sons, New York: 2001, or more recent editions of either of the foregoing, which are incorporated herein by reference. Definitions of various specific functional groups and chemical terms are set forth below and/or in PCT/US2009/005656 (WO/2010/044885). Definitions of various terms may be found in IUPAC Compendium of Chemical Terminology (1997) compiled by Alan D. McNaught and Andrew Wilkinson (Royal Society of Chemistry, Cambridge, UK) or updated online version thereof available at the IUPAC website (http://old.iupac.org/publications/compendium/index.html). The practice of certain aspects described herein may employ conventional techniques of molecular biology, cell culture, recombinant nucleic acid (e.g., DNA) technology, immunology, nucleic acid and polypeptide synthesis, detection, manipulation, and quantification, and RNA interference that are within the ordinary skill of the art. See, e.g., Ausubel, F., et al., (eds.), Current Protocols in Molecular Biology, Current Protocols in Immunology, Current Protocols in Protein Science, and Current Protocols in Cell Biology, all John Wiley & Sons, N.Y., edition as of December 2008; Sambrook, Russell, and Sambrook, Molecular Cloning: A Laboratory Manual, $3^{rd}$ ed., Cold Spring Harbor Laboratory Press, Cold Spring Harbor, 2001; Harlow, E. and Lane, D., Antibodies—A Laboratory Manual, Cold Spring Harbor Laboratory Press, Cold Spring Harbor, 1988. Further information on cancer and treatment of cancer is found, e.g., in Cancer: Principles and Practice of Oncology (V. T. DeVita et al., eds., J.B. Lippincott Company, 8th ed., 2008 or $9^{th}$ ed., 2011) and/or Brunton, L., et al. (eds.) Goodman and Gilman's The Pharmacological Basis of Therapeutics, $12^{th}$ Ed., McGraw Hill, 2010. All patents, patent applications, books, journal articles, documents, databases, websites, articles, publications, references, etc., cited herein are incorporated by reference in their entirety. In the event of a conflict or inconsistency with the specification, the specification shall control. Applicants reserve the right to amend the specification based, e.g., on any of the incorporated material and/or to correct obvious errors. None of the content of the incorporated material shall limit the invention.

II. The Glycine Cleavage System and its Components as Anti-Tumor Targets

Disclosed herein is identification of the glycine cleavage system (GSC) as an anti-tumor target. In some aspects, methods of inhibiting tumor cell survival or proliferation are provided, the methods comprising inhibiting the GCS of a tumor cell. In some embodiments a method of inhibiting tumor cell survival or proliferation comprises contacting a tumor cell with an inhibitor of the GCS. In some embodiments methods of killing a tumor cell are provided, the methods comprising the step of contacting the tumor cell with a GCS inhibitor. In some embodiments a tumor cell overexpresses serine hydroxymethyltransferase 2 (SHMT2). The term "tumor" as used herein encompasses abnormal growths comprising aberrantly proliferating cells. A tumor is typically characterized by excessive cell proliferation that is not appropriately regulated (e.g., that does not respond normally to physiological influences and signals that would ordinarily constrain proliferation) and may exhibit one or more of the following properties: dysplasia (e.g., lack of normal cell differentiation, resulting in an increased number or proportion of immature cells); anaplasia (e.g., greater loss of differentiation, more loss of structural organization, cellular pleomorphism, abnormalities such as large, hyperchromatic nuclei, high nuclear:cytoplasmic ratio, atypical mitoses, etc.); invasion of adjacent tissues (e.g., breaching a basement membrane); and/or metastasis. In certain embodiments a tumor is a malignant tumor, also referred to herein as a "cancer". Malignant tumors have a tendency for sustained growth and an ability to spread, e.g., to invade locally and/or metastasize regionally and/or todistant locations, whereas benign tumors often remain localized at the site of origin and are often self limiting in terms of growth. The term "tumor" includes malignant solid tumors (e.g., carcinomas, sarcomas) and malignant growths in which there may be no detectable solid tumor mass (e.g., certain hematologic malignancies). The term "cancer" is generally used interchangeably with "tumor" herein and/or to refer to a disease characterized by one or more tumors, e.g., one or more malignant or potentially malignant tumors. Cancer includes, but is not limited to: breast cancer; biliary tract cancer; bladder cancer; brain cancer (e.g., glioblastomas, medulloblastomas); cervical cancer; choriocarcinoma; colon cancer; endometrial cancer; esophageal cancer; gastric cancer; hematological neoplasms including acute lymphocytic leukemia and acute myelogenous leukemia; T-cell acute lymphoblastic leukemia/lymphoma; hairy cell leukemia; chronic lymphocytic leukemia, chronic myelogenous leukemia, multiple myeloma; adult T-cell leukemia/lymphoma; intraepithelial neoplasms including Bowen's disease and Paget's disease; liver cancer; lung cancer; lymphomas including Hodgkin's disease and lymphocytic lymphomas; neuroblastoma; melanoma, oral cancer including squamous cell carcinoma; ovarian cancer including ovarian cancer arising from epithelial cells, stromal cells, germ cells and mesenchymal cells; neuroblastoma, pancreatic cancer; prostate cancer; rectal cancer; sarcomas including angiosarcoma, gastrointestinal stromal tumors, leiomyosarcoma, rhabdomyosarcoma, liposarcoma, fibrosarcoma, and osteosarcoma; renal cancer including renal cell carcinoma and Wilms tumor; skin cancer including basal cell carcinoma and squamous cell cancer; testicular cancer including germinal tumors such as seminoma, non-seminoma (teratomas, choriocarcinomas), stromal tumors, and germ cell tumors; thyroid cancer including thyroid adenocarcinoma and medullary carcinoma. In some embodiments a tumor may be of a type has a relatively low likelihood of invasion or metastasis. For example, in some embodiments a tumor may be associated with neurofibromatosis (e.g., type 1, 2, 3, 4, or 5), tuberous sclerosis, Sturge-Weber syndrome or von Hippel-Lindau disease. In some embodiments a tumor is not detectably invasive, e.g., a carcinoma in situ. It will be appreciated that a variety of different tumor types can arise in certain organs, which may differ with regard to, e.g., clinical and/or pathological features and/or molecular markers. Tumors arising in a variety of different organs are discussed, e.g., in DeVita, supra or in the WHO Classification of Tumours series, $4^{th}$ ed, or $3^{rd}$ ed (Pathology and Genetics of Tumours series), by the International Agency for Research on Cancer (IARC), WHO Press, Geneva, Switzerland, all volumes of which are incorporated herein by reference.

In some embodiments a tumor cell is a brain tumor cell, e.g., a glioblastoma cell. In some embodiments a tumor cell is a bladder tumor cell, breast tumor cell, cervical tumor cell, colorectal tumor cell, embryonal tumor cell, gastric tumor cell, germ cell tumor cell, head and neck tumor cell, hematologic tumor cell, kidney tumor cell, melanoma cell, mesothelial tumor cell, ovarian tumor cell, yolk sac tumor cell, or sarcoma cell. In some embodiments a breast tumor cell is a triple negative breast tumor cell. As known in the art, a "triple negative" breast tumor is a breast tumor that does not express estrogen receptor (ER), progesterone receptor (PR), or or Her2/neu. In general, triple negative breast tumors typically have a worse prognosis than breast tumor that are not triple negative. In some embodiments a tumor cell is a tumor initiating cell. In some embodiments a tumor initiating cell is a glioblastoma stem cell (GBM-SC). In some embodiments a tumor cell is not a lung tumor cell. In some embodiments a tumor cell is not a non-small cell lung cancer cell. In some embodiments a tumor is not a colon cancer. In some embodiments a tumor is not a lung tumor. In some embodiments a cancer is not non-small cell lung cancer. In some embodiments a tumor is not a colon cancer.

In some aspects, methods of inhibiting a tumor are provided, the methods comprising inhibiting the GCS in at least some tumor cells of the tumor. In some embodiments a method of inhibiting a tumor comprises contacting the tumor with an inhibitor of the GCS. In some embodiments a method of inhibiting a tumor comprises contacting the tumor with an inhibitor of a GCS component. In some embodiments inhibiting a tumor comprises inhibiting survival or proliferation of at least some tumor cells of the tumor. In some embodiments inhibiting a tumor comprises killing at least some cells of the tumor. In some embodiments inhibiting a tumor comprises inhibiting survival or proliferation of at least some tumor initiating cells. In some embodiments inhibiting a tumor comprises inhibiting tumor progression, e.g., inhibiting local invasion or metastasis. In some embodiments a tumor comprises tumor cells that overexpress SHMT2. In some embodiments a tumor is of a type that has a tendency to overexpress SHMT2. In some embodiments a tumor is a brain tumor e.g., a glioblastoma. In some embodiments a tumor is a bladder tumor, breast tumor, cervical tumor, colorectal tumor, embryonal tumor, gastric tumor, germ cell tumor, head and neck tumor, hematologic tumor, kidney tumor, melanoma, mesothelial tumor, ovarian tumor, yolk sac tumor or sarcoma. In some embodiments a breast tumor is a triple negative breast tumor.

The term "GCS inhibitor" or "inhibitor of the GCS" refers to an agent that inhibits expression of a GCS component, inhibits one or more activit(ies) of a GCS component, or inhibits the glycine catabolism pathway catalyzed by the GCS (or the reverse reaction). Any of a variety of different agents may be used as a GCS inhibitor in various embodiments. Certain GCS inhibitors and methods of identifying GCS inhibitors are discussed further below.

In some embodiments a method comprises (a) contacting one or more cells with a GCS inhibitor; and (b) assessing the survival and/or proliferation of the one or more cells. In some embodiments the one or more cells comprise tumor cells. In some embodiments the one or more cells comprise tumor initiating cells. In some embodiments the one or more cells comprise tumor cells that overexpress SHMT2. For example, in some embodiments at least, at least 5%, 10%, 20%, 30%, 40%, 50%, 60%, 70%, 80%, 90%, 95%, or more, e.g., all or essentially all of the tumor cells overexpress SHMT2. In some embodiments detecting the level of inhibition of the survival and/or proliferation of the one or more tumor cells comprises determining the capacity of the one or more tumor cells to form colonies in suspension culture. In some embodiments detecting the level of inhibition of the survival or proliferation of the one or more tumor cells comprises determining the capacity of the one or more tumor cells to form colonies in a semi-solid medium. In some embodiments detecting the level of inhibition of the survival and/or proliferation of the one or more tumor cells comprises determine the capacity of the one or more tumor cells to form tumor spheres in culture. In some embodiments detecting the level of inhibition of the survival and/or proliferation of the one or more tumor cells comprises determine the capacity of the one or more tumor cells to form tumors in vivo. In some embodiments a GCS inhibitor is contacted with cells, e.g., tumor cells, in combination with a second anti-tumor agent. In some embodiments a method comprises comparing the effect of a GCS inhibitor in combination with a second agent with the effect of the GCS inhibitor when used as a single agent in an ex vivo or in vivo tumor model.

In some embodiments a tumor cell, tumor cell line, or tumor comprises one or more oncogenes or has reduced or absent expression of one or more tumor suppressor genes (TSGs) or reduced or absent activity of one or more TSG gene products, e.g., as a result of a mutation in the TSG. The term "oncogene" encompasses nucleic acids that, when expressed, can increase the likelihood of or contribute to cancer initiation or progression. Normal cellular sequences ("proto-oncogenes") can be activated to become oncogenes (sometimes termed "activated oncogenes") by mutation and/or aberrant expression. In various embodiments an oncogene can comprise a complete coding sequence for a gene product or a portion that maintains at least in part the oncogenic potential of the complete sequence or a sequence that encodes a fusion protein. Oncogenic mutations can result, e.g., in altered (e.g., increased) protein activity, loss of proper regulation, or an alteration (e.g., an increase) in RNA or protein level. Aberrant expression may occur, e.g., due to chromosomal rearrangement resulting in juxtaposition to regulatory elements such as enhancers, epigenetic mechanisms, or due to amplification, and may result in an increased amount of proto-oncogene product or production in an inappropriate cell type. As known in the art, proto-oncogenes often encode proteins that control or participate in cell proliferation, differentiation, and/or apoptosis. These proteins include, e.g., various transcription factors, chromatin remodelers, growth factors, growth factor receptors, signal transducers, and apoptosis regulators. Oncogenes also include a variety of viral proteins, e.g., from viruses such as polyomaviruses (e.g., SV40 large T antigen) and papillomaviruses (e.g., human papilloma virus E6 and E7). A TSG may be any gene wherein a loss or reduction in function of an expression product of the gene can increase the likelihood of or contribute to cancer initiation or progression. Loss or reduction in function can occur, e.g., due to mutation or epigenetic mechanisms. Many TSGs encode proteins that normally function to restrain or negatively regulate cell proliferation and/or to promote apoptosis. In some embodiments an oncogene or TSG encodes a miRNA. Exemplary oncogenes include, e.g., MYC, SRC, FOS, JUN, MYB, RAS, RAF, ABL, ALK, AKT, TRK, BCL2, WNT, HER2/NEU, EGFR, MAPK, ERK, MDM2, CDK4, GLI1, GLI2, IGF2, TP53, etc. Exemplary TSGs include, e.g., RB, TP53, APC, NF1, BRCA1, BRCA2, PTEN, CDK inhibitory proteins (e.g., p16, p21), PTCH, WT1, etc. It will be understood that a number of these oncogene and TSG names encompass multiple family members and that many other TSGs are known.

In some embodiments methods of inhibiting a tumor initiating cell (TIC) are provided, the methods comprising contacting a tumor initiating cell with a GCS inhibitor. The term "tumor initiating cell" is used interchangeably herein with the term "cancer stem cell" (CSC). CSCs are cells within or originating from a tumor that exhibit properties of extensive self-renewal, capacity for multi-lineage differentiation or multipotency, and capacity for continued proliferation, e.g., under appropriate culture conditions. CSCs can be defined functionally as those cells within a tumor mass that have the capacity to seed and generate secondary tumors. In some aspects, CSCs may be defined by their ability to seed tumors at high dilutions (i.e., using very low numbers of cells) in animal models (e.g., immunocompromised mice). Tumors generated by CSCs may resemble the tumor from which they originate, e.g., in terms of morphological and immunohistochemical phenotype. A CSC may exhibit increased likelihood of (i) initiating a tumor; (ii) growing in suspension culture; (iii) forming a colony in soft agar; (iv) forming a tumor sphere; and/or (v) exhibiting resistance to various commonly used chemotherapy drugs and/or radiation. CSCs may be responsible for phenomena such as metastatic dissemination, the primary cause of cancer mortality in many tumor types, and/or for tumor recurrence after removal or ablation of the bulk of the tumor by, e.g., surgery, radiation, chemotherapy, or radiofrequency ablation. CSCs have been identified from a wide variety of tumor types, including brain tumors, breast tumors, colorectal tumors, and others (see, e.g., Singh, C. et al., Nature 432 (2004): 396-401), Al-Hajj M, et al., Proc Natl Acad Sci USA 2003; 100(7):3983-8; Li C, et al., Cancer Res 2007; 67(3): 1030-7; O'Brien C A, et al., Nature 2007; 445(7123): 106-10; Ricci-Vitiani L, et al., Nature 2007; 445(7123):1 11-5). Exemplary glioblastoma tumor initiating cell lines, also termed glioblastoma stem cells (GMB-SCs) are listed in the Examples. A GBM-SC may be a cell obtained from a GBM, or a descendant thereof (e.g., a member of a cell line derived from a GBM). In some embodiments, GBM-SCs can be propagated in vitro and, when cultured in suitable medium, can form neurospheres resembling those formed by normal neural stem cells. In some embodiments, a suitable medium is a neurobasal medium supplemented with appropriate growth factors such as epidermal growth factor and basic fibroblast growth factor. In some embodiments, GBM-SCs can be induced to differentiate in vitro into multiple different neural or glial cell types, such as cells that exhibit cellular marker profiles and morphological characteristics of astrocytes, oligodendrocytes and neurons. In some embodiments, such differentiation can be induced by addition of serum and/or withdrawal of the culture conditions suitable for neurosphere propagation.

CSCs may be identified or isolated in a variety of ways, if desired. CSCs isolated from various tumor types have been reported to exhibit altered expression (e.g., increased or decreased expression) of various cellular markers, e.g., cell surface markers, as compared with normal cells of the same tissue type or as compared with other cells from the same tumor. In some embodiments CSCs have increased or decreased expression of one or more cellular marker(s), which expression pattern may be used to identify or isolate them. See, e.g., PCT/US2009/002254 and references therein, which are incorporated herein by reference. In certain embodiments, the one or more cellular markers are selected from: CD15, CD20, CD24, CD34, CD38, CD44, CD45, CD105, CD133, CD166, CD171 (L1CAM), EpCAM, ESA, SCAI, Pecam, Strol, and alpha 6 integrin. In some embodiments CSCs are CD44+, CD24– (CD44$^{high}$, CD24$^{low}$). In some embodiments CSCs, e.g., GBM-SCs, express at least one cell surface marker selected from CD133, CD15, alpha 6 integrin, and L1CAM. In some embodiments GBM-SCs are A2B5+. A2B5 is a monoclonal antibody that recognizes GT3 gangliosides. In some embodiments CSCs, e.g., GBM-SCs, express aldehyde dehydrogenase (ALDH), e.g., aldehyde dehydrogenase 1. ALDH+ cells can be identified, for example, using a functional assay that uses the reagent ALDEFLUOR (STEM-CELL Technologies Inc, Vancouver, BC, Canada). The ALDEFLUOR substrate, BODIPY aminoacetaldehyde (BAAA), is converted by ALDH in the cells into a fluorescent molecule that accumulates in cells in the presence of efflux inhibitors, allowing identification of cells with high ALDH activity. In some embodiments CSCs, e.g., GBM-SCs, comprise a "side population" of cells that have the ability to exclude the Hoescht 33342 fluorescent dye from the intracellular compartment. In some embodiments CSCs, e.g., GBM-SCs, express at least one transcription factor selected from OCT4, SOX2, NANOG, c-MYC, and NOTCH. In some embodiments CSCs, e.g., GBM-SCs, may exhibit distinct physical characteristics that may be used to identify or isolate them independent of expression of particular cellular markers. For example, in some embodiments CSCs, e.g., GBM-SCs, may exhibit increased autofluorescence as compared with non-CSCs and/or have a distinctive morphology (e.g., large agranular cells with a very high nuclear:cytoplasmic ratio).

In some embodiments a method of reducing the number of TICs in a tumor comprises contacting the tumor with a GCS inhibitor, whereby the number of TICs in the tumor is reduced. In some embodiments a method of inhibiting treatment resistance or inhibiting emergence of treatment resistance in a tumor comprises contacting the tumor with a GCS inhibitor, whereby resistance or the emergence of treatment resistance is inhibited. In some embodiments a method of inhibiting tumor metastasis comprises contacting a tumor with a GCS inhibitor, whereby tumor metastasis is inhibited. In some embodiments a method of inhibiting tumor recurrence comprises treating a subject in need thereof with a GCS inhibitor, whereby the likelihood of tumor recurrence is inhibited.

In some aspects, methods of treating a subject in need of treatment for a tumor are provided, the methods comprising inhibiting the GCS in at least some tumor cells in the subject. In some embodiments a method of treating a subject in need of treatment for a tumor comprises administering an inhibitor of the GCS to the subject. In some embodiments at least some of the tumor cells overexpress SHMT2. In some embodiments the tumor is of a tumor type that has a tendency to overexpress SHMT2. In some embodiments the tumor is a brain tumor e.g., a glioblastoma. In some embodiments the tumor is a bladder tumor, breast tumor, cervical tumor, colorectal tumor, embryonal tumor, gastric tumor, germ cell tumor, head and neck tumor, hematologic tumor, kidney tumor, melanoma, mesothelial tumor, ovarian tumor, yolk sac tumor or sarcoma.

In some embodiments a method further comprises assessing the response of the tumor to administration of the GCS inhibitor. In some embodiments assessing a response comprises assessing size, growth rate, local progression, or metastasis of the tumor. In some embodiments a method further comprises assessing the subject for presence or severity of one or more symptoms or signs of the tumor. In some embodiments a GCS inhibitor is administered in combination with use of a second anti-tumor agent, e.g., an agent approved for use in treating at least one tumor type.

In some aspects, compositions useful for inhibiting a tumor cell or tumor or for treating a subject in need of treatment for a tumor are provided, the compositions comprising an inhibitor of the GCS. In some embodiments a composition further comprises an additional anti-tumor agent.

The GCS comprises a multienzyme system present in a wide range of organisms and is the major pathway for the catabolism of glycine in humans (7). GCS components include glycine dehydrogenase (GLDC; also called glycine decarboxylase), glycine cleavage system protein H (GCSH), aminomethyltransferase (AMT), and dihydrolipoamide dehydrogenase (DLD). In animals, the proteins of the GCS (GCS proteins) are located in the mitochondria, loosely bound to the inner mitochondrial membrane. Mutations in the gene that encodes GLDC, or, less commonly, mutations in the genes encoding AMT or GCSH, underlie the inherited metabolic disorder non-ketotic hyperglycinemia (NKH) [MIM ID #605899]. NKH, also known as glycine encephalopathy is characterized by accumulation of glycine in tissues and body fluids (e.g., plasma and cerebrospinal fluid) and results in a range of neurodevelopmental defects. It is inherited as an autosomal recessive trait. NKH is discussed in Hamosh A, et al., "Glycine Encephalopathy" in Pagon R A, et al., (eds.) Gene Reviews [Internet]. Seattle (Wash.): University of Washington, Seattle; 1993-2002 [updated 2009 Nov. 24] US National Library of Medicine Bookshelf ID: NBK1357 PMID: 20301531, available at http://www.ncbi.nlm.nih.gov/books/NBK357 and in Applegarth, D. A. and Toone, J. R. Nonketotic hyperglycinemia (glycine encephalopathy): laboratory diagnosis. Mol. Genet. Metab. 74(1-2): 139-146 (2001)).

As described further in the Examples, Applicants surveyed a set of genes involved in amino acid catabolism to assess the potential requirement for expression of these genes in survival and/or proliferation of glioblastoma (GBM) cells. The genes were selected based at least in part on the following criteria: (1) loss-of-function mutations in the gene are a known cause of an inherited metabolic disorder in humans; and (2) expression of the gene was determined to be positively associated with GBM, GBM tumor initiating cells, and stemness. The effect of inhibiting expression of the selected genes was tested using short hairpin RNA (shRNA)-mediated knockdown. It was discovered that knockdown of the gene that encodes the GCS component glycine dehydrogenase (GLDC) significantly reduced viability of a g GBM-derived tumor-initiating cell line (also referred to herein as a GBM stem cell (GBM-SC) line). GLDC knockdown also markedly reduced the viability of a number of other tumor cell lines derived from GBM or derived from a variety of other cancer types. Cell lines were classified as GLDC-knockdown-sensitive or insensitive based on the extent to which GLDC knockdown resulted in reduced viability. Those cell lines that exhibited markedly reduced viability (e.g., at least 10%, 20%, 25%, or more reduction in viability) were considered "GLDC-knockdown-sensitive" while those cell lines that did not exhibit markedly reduced viability (e.g., less than a 6% reduction in viability) were considered "GLDC-knockdown-insensitive" for these experiments. shRNA-mediated inhibition of a different GCS component, glycine cleavage system protein H (GCSH), or treatment with cysteamine, a small molecule that is a known inhibitor of the GCS (9), markedly impaired viability of cell lines in the GLDC-knockdown-sensitive group. Thus, multiple lines of evidence indicate that inhibition of the GCS reduces the viability of tumor cells of a variety of different tumor types. As described further below, it was also discovered that overexpression of SHMT2 correlates with increased likelihood of tumor cell sensitivity to GCS inhibition. In some aspects, assessing the expression of SHMT2 is of use to identify tumor cells and/or tumors that have increased likelihood of being sensitive ("responding") to administration of a GCS inhibitor. In some aspects, assessing the expression of SHMT2 is of use to identify subjects in need of treatment for cancer, who have increased likelihood of benefiting from administration of a GCS inhibitor.

The GCS catalyzes the reversible oxidation of glycine, yielding carbon dioxide, ammonia, N5, N10-methylenetetrahydrofolate (5,10-CH2-H4 folate), and reduced pyridine nucleotide (NADH), according to the following overall reaction scheme:

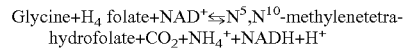

GLDC, also termed P protein, is a pyridoxal phosphate-dependent glycine decarboxylase (EC1.4.4.2). GCSH, also termed H protein, is a lipoic acid-containing protein that serves as a carrier protein. AMT, also termed T protein, is a tetrahydrofolate-requiring enzyme (EC2.1.2.10). DLD, also termed L protein or E3, is a lipoamide dehydrogenase; (EC1.8.1.4). Without wishing to be bound by any theory, the glycine catabolism reaction catalyzed by the GCS is believed to occur in three reactions (sometimes termed partial reactions), as follows:

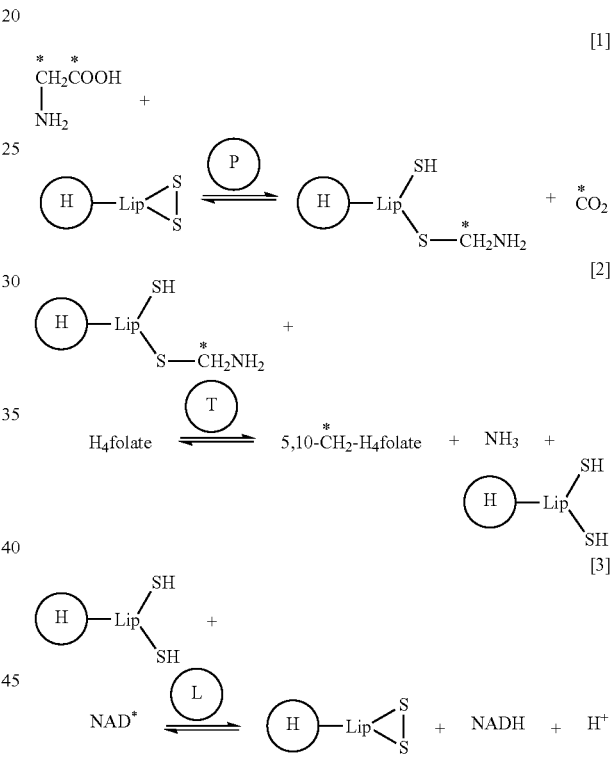

In the above reactions, Lip, H4folate, and 5,10-CH2-H4folate represent lipoyl moiety, tetrahydrofolate, and N5,N10-methylene-H4folate, respectively (7). In the first reaction, P protein catalyzes the decarboxylation of glycine concomitantly with the transfer of the residual aminomethyl group to a sulfur atom on the lipoyl group of the oxidized H-protein, generating aminomethylated H-protein. In the second reaction, T-protein catalyzes the transfer of a methylene group from aminomethylated H-protein to tetrahydrofolate (THF), resulting in the release of $NH_3$ and the generation of reduced H-protein. In the third reaction, the dihydrolipoyl group of reduced H-protein is reoxidized by L-protein (7). Under appropriate conditions, e.g., in anaerobic conditions such as those that exist in anaerobic bacteria, these reactions can function in reverse, resulting in synthesis of glycine.

GCS components from a number of different eukaryotes and prokaryotes have been purified and characterized (see, e.g., references cited in (7), which are incorporated herein by reference). For example, GCS components have been purified from tissue of several vertebrates, including human, rat, chicken, and bovine; from plants (e.g., pea), and from various bacterial species. Glycine cleavage activity has been detected in liver, kidney, and brain in various verterbrate species. cDNAs encoding GLDC, GCSH, AMT, and DLD of a number of species, including humans, other vertebrates, and various bacteria and plants, have been cloned and sequences are known in the art. Sequences are available, e.g., in various publicly available databases such as the National Center for Biotechnology Information (NCBI) databases. Structures (e.g., crystal structures) of GCS components from several species have been obtained. Structure information can be found, e.g., in the Protein Data Bank (PDB) database (www.pdb.org). Table B lists Gene IDs (from the NCBI Gene Database) and mRNA and protein accession numbers from the NCBI Reference Sequence (RefSeq) database for human GCS components. The GLDC, GCSH, AMT, and DLD proteins are naturally produced as "pre-proteins" that include a mitochondrial targeting sequence (MTS) at their N-terminus, which sequence is typically removed when the pre-protein is processed into a mature form in, e.g., a mammalian cell. The sequences listed under the accession numbers in Table B are exemplary normal sequences and include the MTS sequences. It will be understood that other normal sequences may exist in the population. A normal DNA, RNA, or polypeptide sequence is a sequence found in at least some healthy individuals and not known to contribute to or result in a disease. A normal DNA, RNA, or polypeptide sequence may be, e.g., (i) the most common sequence present in a population; (ii) a reference sequence (e.g., an NCBI RefSeq sequence or UniProt reference sequence); (iii) a sequence in which the nucleotide present at each position of the sequence is the most common nucleotide present at that position in a population; or (iv) a sequence in which all difference(s) relative to at least one of the foregoing sequences have a frequency of at least about 1% in a population.

TABLE B

GCS Components (with human Gene IDs and accession numbers)

| Name | Official Gene Symbol | Gene ID | RefSeq mRNA and protein accession numbers |
|---|---|---|---|
| glycine cleavage system protein P (glycine dehydrogenase) | GLDC | 2731 | NM_000170.2; NP_000161.2 |
| glycine cleavage system protein H | GCSH | 2653 | NM_004483.4; NP_004474.2 |
| glycine cleavage system protein L (dihydrolipoamide dehydrogenase) | DLD | 1738 | NM_000108.3; NP_000099.2 |
| glycine cleavage system protein T (aminomethyl-transferase) | AMT | 275 | NM_000481.3; NP_000472.2 (isoform 1) NM_001164710.1; NP_001158182.1 (isoform 2) NM_001164711.1; NP_001158183.1 (isoform 3) NM_001164712.1; NP_001158184.1 (isoform 4) |

GCS components have been expressed in various host cells using recombinant DNA technology and purified in active (or activatable) form. For example, tagged human H protein has been produced and purified (Zay, A., et al., Glycine cleavage enzyme complex: Molecular cloning and expression of the H-protein cDNA from cultured human skin Fibroblasts Biochem. Cell Biol. 89(3):299-307 (2011)). E. coli lipoate protein ligase (LPL) has been expressed and purified and shown to lipoylate (attach the lipoate prosthetic group to) the apo-H-protein, converting it to the functional holo-H-protein. Tagged human T protein has been produced and purified (Okamura-Ikeda, K., et al. Crystal Structure of Human T-protein of Glycine Cleavage System at 2.0 A° Resolution and its Implication for Understanding Non-ketotic Hyperglycinemia. J. Mol. Biol. 351, 1146-1159 (2005)). Human L protein (tagged or untagged) has been produced and purified (Kim, H., et al., Expression of cDNA sequences encoding mature and precursor forms of human dihydrolipoamide dehydrogenase in Escherichia coli. J. Biol. Chem. 266, 9367-9373 (1991); Liu, T., Spectroscopic studies of the characterization of recombinant human dihydrolipoamide dehydrogenase and its site-directed mutants. J. Biol. Chem. 270, 15545-15550 (1995); Brautigam et al., Crystal structure of human dihydrolipoamide dehydrogenase: NAD+/NADH binding and the structural basis of disease-causing mutations, J. Mol. Biol. 350: 543-552 (2005); and references therein). Mutant GCS components have been isolated from various species or generated using recombinant DNA techniques and assessed for activity. Various amino acid residues important for activity have been identified using, e.g., sequence conservation, structural information, and/or assays of activity of naturally occurring GCS proteins (e.g., mutant proteins occurring in NHK) or recombinantly produced GCS proteins containing amino acid alterations (see, e.g., Brautigam et al, 2005; Liu et al, 1995; Nakai, T. et al., Structure of P-protein of the glycine cleavage system: implications for nonketotic hyperglycinemia. EMBO J. 24(8):1523-36 (2005)).

The subunit compositions of P-proteins have been classified into two types: those from eukaryotes and certain prokaryotes (e.g. E. coli) are homodimers while those from various other prokaryotes (e.g., Thermus thermophilus (Tth)) are heterotetramers. Crystal structures of Tth P protein have been determined for the apoenzyme, the holoenzyme, and the holoenzyme in complex with an inhibitor ((aminooxy) acetate) and used to generate a model of the structure of human P protein (Nakai et al., 2005). Sequence conservation and structural information were used to identify the active site and certain functionally important residues of human P protein.

H-protein is a monomeric protein of molecular weight ~14 kDa that plays acentral role in glycine cleavage. The lipoic acid prosthetic group covalently bound to a specific lysine residue of the H-protein interacts with sites on the P-, T- and L-proteins. Structures of H-protein from pea leaves, with a reduced lipoic acid, an oxidized lipoic acid, and aminomethyllipoic acid have been determined (Pares et al., 1994; Pares et al., 1995). A crystal structure of bovine H protein has been reported (Higashiura A, et al., High-resolution X-ray crystal structure of bovine H-protein at 0.88 A resolution. Acta Crystallogr D Biol Crystallogr. 66(Pt 6):698-708 (2010).

Crystal structures of mature human T protein in free form and bound to a competitive inhibitor, 5-methyltetrahydrofolate (5-CH3-H4folate), have been determined (Okamura-Ikeda, K., et al., 2005). Analysis of the structure indicated that human T protein monomer consists of three domains arranged in a cloverleaf-like structure with a central cavity, which 5-CH3-H4folate, an analog of the folate substrate, occupies with extensive hydrogen bonds and hydrophobic contacts. Most of the disease-related residues cluster around the cavity, forming extensive hydrogen bonding networks. Based on structural and mutational analyses it was proposed that Arg292 interacts through water molecules with the folate polyglutamate tail, and that the invariant Asp101, located close to the N10 group of 5-CH3-H4folate, might play a role in the initiation of catalysis.

L protein catalyzes the last step of the glycine cleavage reaction scheme shown above, which involves the oxidation of dihydrolipoamide (Lip-$(SH)_2$), forming lipoamide (Lip-$S_2$). An FAD cofactor is an intermediary in the electron transfer from Lip-$(SH)_2$ to $NAD^+$. L protein functions as a homodimer with two intramolecular disulfide bridges between cysteine residues that are proximal to the FAD cofactors. Crystal structures of human L protein in the presence of NAD+ or NADH have been determined (Brautigam 2005, supra). NKH-causing mutations were found to occur at the dimer interface, the active site, or the FAD and NAD (+)-binding sites.

In some aspects, methods useful for identifying tumor cells, tumor cell lines, or tumors that are sensitive to GCS inhibition are provided herein. In some aspects, methods useful for identifying agents to which tumor cells, tumor cell lines, or tumors are sensitive are provided herein. In some embodiments atumor, tumor cell, or tumor cell line is considered "sensitive" to an agent (e.g., a GCS inhibitor) or intervention if exposure to the agent or intervention has at least one anti-tumor effect on the tumor, tumor cell, or tumor cell line. In some embodiments an "anti-tumor effect" is, e.g., inhibition of tumor cell survival (viability), proliferation, tumor initiating capacity, and/or metastasis, or a decrease in tumor size, growth rate, or likelihood of progression or recurrence. For example, in some embodiments a tumor, tumor cell, or tumor cell line is considered sensitive to a GCS inhibitor if the GCS inhibitor inhibits tumor cell viability or proliferation, e.g., if the tumor, tumor cell, or tumor cell line exhibits a decrease in cell viability and/or cell proliferation following exposure to the GCS inhibitor as compared with a suitable reference value. A suitable reference value may be, e.g., the level of viability or proliferation that existed prior to exposure to the GCS inhibitor or the level of viability and/or proliferation that would be expected in the absence of the GCS inhibitor. In some embodiments a tumor is considered sensitive to a GCS inhibitor if exposure to the GCS inhibitor results in a reduction in tumor size, growth rate, or likelihood of metastasis or recurrence, e.g., if the tumor exhibits a decrease in size, growth rate, or likelihood of metastasis or recurrence following exposure to a GCS inhibitor as compared with a suitable reference value. A suitable reference value may be, e.g., the size, growth rate, or likelihood of metastasis or recurrence that that existed prior to exposure to the GCS inhibitor or that would be expected in the absence of the GCS inhibitor. In some embodiments a level that would be expected in the absence of the GCS inhibitor is determined by performing a control assay in which comparable tumor or tumor cell(s), e.g., tumor cells of the same tumor cell line or a tumor derived from the same tumor cell line, is not exposed to the GCS inhibitor. In some embodiments a level that would be expected in the absence of the GCS inhibitor maisdetermined based on historical data. In some embodiments a level that would be expected in the absence of the GCS inhibitor is determined using a control group of subjects not treated with a GCS inhibitor.

In some embodiments sensitivity of a tumor cell, tumor cell line, or tumor to GCS inhibition or sensitivity to an agent, e.g., a GCS inhibitor, or combination of agents, is assessed using tumor cells in culture. Numerous tumor cell lines and non-tumorigenic cell lines are known in the art. Cell lines can be obtained, e.g., from depositories or cell banks such as the American Type Culture Collection (ATCC), Coriell Cell Repositories, Deutsche Sammlung von Mikroorganismen und Zellkulturen (German Collection of Microorganisms and Cell Cultures; DSMZ), European Collection of Cell Cultures (ECACC), Japanese Collection of Research Bioresources (JCRB), RIKEN, Cell Bank Australia, etc. The paper and online catalogs of the afore-mentioned depositories and cell banks are incorporated herein by reference. Exemplary tumor cell lines and tumors are described in the Examples. In some embodiments a tumor cell or tumor cell line overexpresses SHMT2. In some embodiments tumor cells, e.g., a tumor cell line, originates from a human tumor. In some embodiments tumor cells, e.g., a tumor cell line, originates from a tumor of a non-human animal, e.g., a tumor that was not produced by introduction of tumor cells into the non-human animal. In some embodiments tumor cells originate from a naturally arising tumor (i.e., a tumor that was not intentionally induced or generated for, e.g., experimental purposes).

In some embodiments experimentally produced tumor cells are used. Tumor cells can be produced by genetically modifying a non-tumor cell, e.g., a non-tumor somatic cell, e.g., by expressing or activating an oncogene in the non-tumor cell and/or inactivating or inhibiting expression of one or more tumor suppressor genes (TSG) or inhibiting activity of a gene product of a TSG. Certain experimentally produced tumor cells and exemplary methods of producing tumor cells are described in PCT/US2000/015008 (WO/2000/073420) and/or in USSN 10/U.S. Ser. No. 10/767,018. In certain embodiments a non-tumor cell is immortalized by causing the cell to express telomerase catalytic subunit (e.g., human telomerase catalytic subunit; hTERT). In some embodiments a tumor cell is produced from a non-tumor cell by introducing one or more expression construct(s) or expression vector(s) comprising an oncogene into the cell or modifying an endogenous gene (proto-oncogene) by a targeted insertion into or near the gene or by deletion or replacement of a portion of the gene. In some embodiments a TSG is knocked out or functionally inactivated using gene targeting. For example, a portion of a TSG may be deleted or the TSG may be disrupted by an insertion. In some embodiments a TSG is inhibited by introducing into a cell one or more expression construct(s) or expression vector(s) encoding an inhibitory molecule (e.g., an RNAi agent such as a shRNA or a dominant negative or a negative regulator) that is capable of inhibiting the expression or activity of an expression product of a TSG. Oncogenes and/or TSG inhibitory molecules may be expressed under control of suitable regulatory elements, which may be constitutive or regulatable (e.g., inducible). In some embodiments tumor cells may be produced by expressing or activating multiple oncogenes and/or inhibiting or inactivating multiple TSGs, e.g., 1, 2, 3, 4, or more oncogenes and/or 1, 2, 3, 4, or more TSGs. Many combinations of oncogenes and/or TGSs whose expression/activation or inhibition/inactivation, respectively, can be used to induce tumors are known in the art.

Tumor cells may be maintained in a culture system comprising a culture medium to which an agent (e.g., a GCS inhibitor) is or has been added. The effect of the agent on tumor cell viability, proliferation, tumor-initiating capacity, or any other tumor cell property may be assessed. In general, any suitable method known in the art may be used for assessing tumor cell viability or proliferation or tumor-initiating capacity in various embodiments. In certain embodiments survival and/or proliferation of a cell or cell population, e.g., in cell culture, may be determined by: a cell counting assay (e.g., using visual inspection, automated image analysis, flow cytometer, etc.), a replication assay, a cell membrane integrity assay, a cellular ATP-based assay, a mitochondrial reductase activity assay, a BrdU, EdU, or H3-Thymidine incorporation assay, a DNA content assay using a nucleic acid dye, such as Hoechst Dye, DAPI, Actinomycin D, 7-aminoactinomycin D or propidium iodide, a cellular metabolism assay such as resazurin (sometimes known as AlamarBlue or by various other names), MTT, XTT, and CellTitre Glo, etc., a protein content assay such as SRB (sulforhodamine B) assay; nuclear fragmentation assays; cytoplasmic histone associated DNA fragmentation assay; PARP cleavage assay; TUNEL staining; or annexin staining.

It will be understood that inhibition of cell proliferation or survival by a GCS inhibitor may, or may not, be complete. For example, cell proliferation may, or may not, be decreased to a state of complete arrest for an effect to be considered one of inhibition or reduction of cell proliferation. In some embodiments, "inhibition" may comprise inhibiting proliferation of a cell that is in a non-proliferating state (e.g., a cell that is in the G0 state, also referred to as "quiescent") and/or inhibiting proliferation of a proliferating cell (e.g., a cell that is not quiescent). Similarly, inhibition of cell survival may refer to killing of a cell, or cells, such as by causing or contributing to necrosis or apoptosis, and/or the process of rendering a cell susceptible to death. The inhibition may be at least about 10%, 15%, 20%, 25%, 30%, 35%, 40%, 45%, 50%, 55%, 60%, 65%, 70%, 75%, 80%, 85%, 90%, 95%, 99%, or 100% of a reference level (e.g., a control level). For example, in some embodiments a GCS inhibitor is used, e.g., contacted with tumor cells, e.g., tumor cells that overexpress SHMT2, in an amount (e.g., at a concentration) that inhibits tumor cell proliferation or survival by a selected amount, e.g., by at least about 10%, 15%, 20%, 25%, 30%, 35%, 40%, 45%, 50%, 55%, 60%, 65%, 70%, 75%, 80%, 85%, 90%, 95%, 99%, or 100% of a reference level (e.g., a control level).

In some embodiments an anti-tumor effect is inhibition of the capacity of tumor cells to form colonies in suspension culture. In some embodiments an anti-tumor effect is inhibition of capacity of the one or more tumor cells to form colonies in a semi-solid medium such as soft agar or methylcellulose. In some embodiments an anti-tumor effect is inhibition of capacity of the one or more tumor cells to form tumor spheres in culture. In some embodiments an anti-tumor effect is inhibition of the capacity of the one or more tumor cells to form tumors in vivo.

In some embodiments sensitivity of a tumor cell, tumor cell line, or tumor to GCS inhibition or sensitivity to an agent, e.g., a GCS inhibitor, or combination of agents, is assessed using an in vivo tumor model. An "in vivo" tumor model involves the use of one or more living non-human animals ("test animals"). For example, an in vivo tumor model may involve administration of an agent (e.g., a GCS inhibitor) and/or introduction of tumor cells to one or more test animals. In some embodiments a test animal is a mouse, rat, or dog. Numerous in vivo tumor models are known in the art. By way of example, certain in vivo tumor models are described in U.S. Pat. No. 4,736,866; U.S. Ser. No. 10/990,993; PCT/US2004/028098 (WO/2005/020683); and/or PCT/US2008/085040 (WO/2009/070767). Introduction of one or more cells into a subject (e.g., by injection or implantation) may be referred to as "grafting", and the introduced cell(s) may be referred to as a "graft". In general, any tumor cells may be used in an in vivo tumor model in various embodiments. Tumor cells may be from a tumor cell line or tumor sample. In some embodiments tumor cells originate from a naturally arising tumor (i.e., a tumor that was not intentionally induced or generated for, e.g., experimental purposes). In some embodiments experimentally produced tumor cells may be used. The number of tumor cells introduced may range, e.g., from 1 to about 10, $10^2$, $10^3$, $10^4$, $10^5$, $10^6$, $10^7$, $10^8$, $10^9$, or more. In some embodiments at least some of the tumor cells overexpress SHMT2, e.g., the tumor cells are from a tumor cell line or tumor that overexpresses SHMT2. For example, at least 5%, 10%, 20%, 30%, 40%, 50%, 60%, 70%, 80%, 90%, 95%, or more, e.g., all or essentially all of the tumor cells may overexpress SHMT2. In some embodiments the tumor cells are of the same species or inbred strain as the test animal. In some embodiments tumor cells may originate from the test animal. In some embodiments the tumor cells are of a different species than the test animal. For example, the tumor cells may be human cells. In some embodiments, a test animal is immunocompromised, e.g., in certain embodiments in which the tumor cells are from a different species to the test animal or originate from an immunologically incompatible strain of the same species as the test animal. For example, a test animal may be selected or genetically engineered to have a functionally deficient immune system or may be treated (e.g., with radiation or an immunosuppressive agent or surgery such as removal of the thymus) so as to reduce immune system function. In some embodiments, a test animal is a SCID mouse, NOD mouse, NOD/SCID mouse, nude mouse, and/or Rag1 and/or Rag2 knockout mouse, or a rat having similar immune system dysfunction. Tumor cells may be introduced at an orthotopic or non-orthotopic location. In some embodiments tumor cells are introduced subcutaneously, under the renal capsule, or into the bloodstream. Non-tumor cells (e.g., fibroblasts, bone marrow derived cells), an extracellular matrix component or hydrogel (e.g., collagen or Matrigel®), or an agent that promotes tumor development or growth may be administered to the test animal prior to, together with, or separately from the tumor cells. Tumor cells may be contacted with an agent (e.g., a GCS inhibitor) prior to grafting and/or following grafting (by administering the agent to the test animal). The number, size, growth rate, metastasis, or other properties may be assessed at one or more time points following grafting. In some embodiments a tumor in an in vivo tumor model arises due to neoplastic transformation that occurs in vivo, e.g., at least in part as a result of one or more mutations existing or occurring in a cell in vivo. In some embodiments a test animal is a tumor-prone animal. The animal may, for example, be of a species or strain that naturally has a predisposition to develop tumors and/or may be a genetically engineered animal. For example, in some embodiments the animal is a genetically engineered animal at least some of whose cells comprise, as a result of genetic modification, at least one activated oncogene and/or in which at least one TSG has been functionally inactivated. Standard methods of generating genetically modified animals, e.g., transgenic animals that comprises exogenous genes or animals that have an alteration to an endogenous gene, e.g., an insertion or an at least partial deletion or replacement (sometimes referred to as "knockout" or "knock-in" animal) can be used.

Tumor number, size, growth rate, or metastasis may, for example, be assessed using various imaging modalities, e.g., X-ray, magnetic resonance imaging, functional imaging, e.g., of metabolism (e.g., using PET scan), etc. In some embodiments tumor(s) may be removed from the body (e.g., at necropsy) and assessed (e.g., tumors may be counted, weighed, and/or size (e.g., dimensions) measured). In some embodiments the size and/or number of tumors may be determined non-invasively. For example, in certain tumor models, tumor cells that are fluorescently labeled (e.g., by expressing a fluorescent protein such as GFP) can be monitored by various tumor-imaging techniques or instruments, e.g., non-invasive fluorescence methods such as two-photon microscopy. The size of a tumor implanted subcutaneously can be monitored and measured underneath the skin.

In some embodiments treatment effect or sensitivity of a tumor in a human subject may be evaluated at least in part using objective criteria known in the art. For example, the original or revised (e.g., Version 1.1) Response Evaluation Criteria In Solid Tumors (RECIST), may be used to determine if a cancer patient improves ("responds"), remains about the same ("stable disease"), or worsens ("progressive disease") based on anatomical tumor burden. (Therasse P, et al. J Natl Cancer Inst (2000) 92:205-16; Eisenhauer, E., et al., Eur J Cancer. (2009) 45(2):228-47). Response assessment for brain tumors (e.g., in high-grade gliomas such as glioblastoma) may use the Macdonald criteria (Macdonald D, et al. (1990) Response criteria for phase II studies of supratentorial malignant glioma. J Clin Oncol 8:1277-1280), e.g., as extrapolated to magnetic resonance imaging (Rees J (2003) Advances in magnetic resonance imaging of brain tumours. Curr Opin Neurol 16:643-650) or an updated version of the Macdonald criteria (Wen, P Y, et al., J Clin Oncol. (2010) 28(11):1963-72). Exemplary lymphoma response assessment is described in Cheson B D, et al. J Clin Oncol 2007; 10:579-86).

In some embodiments a tumor may be considered "sensitive" if the subject experiences a response (complete or partial response) or stable disease or a slowing of tumor progression for at least a period of time, e.g., a period of time that would be considered clinically meaningful. Tumor progression may comprise, e.g., progression to a more advanced stage or grade; local, regional, or distant spread (e.g., metastasis). In some embodiments, a decrease in viability, proliferation, size, growth rate, or likelihood of progression or recurrence is statistically significant. In some embodiments a period of time may be at least 4, 6, 8, 12 weeks, or more. The criteria mentioned herein for assessing tumor sensitivity in human subjects are merely exemplary. Modified versions or other reasonable criteria may be used. In general, criteria based on anatomic tumor burden should reasonably correlate with a clinically meaningful benefit such as increased survival (e.g, increased progression-free survival, increased cancer-specific survival, or increased overall survival) or at least improved quality of life, such as reduction in one or more symptoms.

In some embodiments treatment effect or sensitivity of a tumor, e.g., in a human subject, may beassessed by evaluating an outcome. In some embodiments overall survival may be assessed. In some embodiments disease-specific survival (i.e., survival considering only mortality due to cancer) is assessed. In some embodiments progression-free survival is assessed. An outcome may be assessed over a given time period, e.g., 1, 2, 5, 10, 15, or 20 years from, e.g., the date of diagnosis or a date of initiating treatment. Methods and criteria for evaluating progression, response to treatment, existence of metastases, and other outcomes are known in the art and may include objective measurements (e.g., anatomical tumor burden) and criteria, clinical evaluation of symptoms), or combinations thereof. For example, imaging (e.g., using X-ray, CT scan, or MRI scan, etc.) and/or functional imaging may be used to detect or assess lesions (local or metastatic), e.g., to measure anatomical tumor burden, detect new lesions, etc.

III. SHMT2 Expression in Tumors and Uses Relating Thereto

As described further in the Examples, Applicants discovered that (i) expression of mitochondrial serine hydroxymethyltransferase 2 (SHMT2) is elevated in a number of tumor types; and (ii) the level of SHMT2 expression correlates with tumor cell sensitivity to GCS inhibition. Among a panel of tumor cell lines arising from a diverse set of tumor types, analysis of the expression levels of multiple genes involved in glycine metabolism revealed that expression of mitochondrial SHMT2, an enzyme involved in the conversion of serine to glycine in the mitochondria, was tightly correlated with sensitivity to GLDC knockdown. Tumor cell lines that were sensitive to GLDC knockdown (i.e., tumor cells lines whose survival or proliferation was inhibited by GLDC knockdown) had markedly higher expression of SHMT2 compared to insensitive cells. Tumor cell lines that overexpressed SHMT2 relative to, e.g., normal tissue controls, were sensitive to GCS inhibition by a small molecule (cysteamine), whereas tumor cell lines that displayed low or absent expression of SHMT2 were insensitive to GCS inhibition. Thus, expression level of SHMT2 is correlated with tumor cell sensitivity to GCS inhibition. It was also observed that shRNA-mediated knockdown of SHMT2 in tumor cells that were sensitive to GCS inhibition protected these cells against GLDC shRNAs. Without wishing to be bound by any theory, this result suggests that the relationship between SHMT2 levels and sensitivity to GCS inhibition is not simply correlative but may also be functionally relevant.

Human SHMT2 has been assigned Gene ID 6472. SHMT2 genes (homologs of the human gene) have been identified in a wide range of other species (e.g., other vertebrates, insects, fungi). Multiple isoforms of human SHMT2 polypeptide have been identified, and multiple transcript variants are known. Table C lists RefSeq accession numbers of exemplary sequences of human SHMT2 protein isoforms and mRNA transcript variants.

TABLE C

Human SHMT2 and RefSeq accession numbers of isoforms and transcripts)

| Protein Name | RefSeq mRNA and protein accession numbers |
|---|---|
| serine hydroxymethyltransferase, mitochondrial isoform 1 precursor | NM_005412.5; NP_005403.2 (transcript variant 1) |
| serine hydroxymethyltransferase, mitochondrial isoform 2 precursor | NM_001166356.1; NP_001159828.1 (transcript variant 2) |
| serine hydroxymethyltransferase, mitochondrial isoform 3 | NM_001166357.1; NP_001159829.1 (transcript variant 3) |
| | NM_001166358.1; NP_001159830.1 (transcript variant 4) |
| | NM_001166359.1; NP_001159831.1 (transcript variant 5) |

Applicants discovered that SHMT2 mRNA levels were significantly elevated in a large number of cancers, relative to normal tissue controls. For example, microarray-based meta-analyses revealed that SHMT2 expression is increased in a number of cancers, including a variety of brain tumors, bladder tumors, breast tumors, cervical tumors, colorectal tumors, embryonal tumors, gastric tumors, germ cell tumors, head and neck tumors, hematologic tumors, kidney tumors, melanomas, mesothelial tumors, ovarian tumors, yolk sac tumors, and sarcomas. In most cases SHMT2 was within the top 1% of overexpressed genes in that particular cancer (see Table 1 in Examples). Thus, SHMT2 expression level can be used for classification across a broad spectrum of human tumors.

In some aspects, methods of classifying a tumor cell, tumor cell line, tumor, or subject are provided herein. In some embodiments a method of classifying a tumor cell, tumor cell line, or tumor comprises: (a) assessing SHMT2 expression in the tumor cell, tumor cell line, or tumor; and (b) classifying the tumor cell, tumor cell line, or tumor based on results of step (a). In some embodiments a tumor cell, tumor cell line, or tumor is classified into one of at least two groups based on expression of SHMT2. For example, in some embodiments a tumor cell, tumor cell line, or tumor is classified as exhibiting overexpression of SHMT2 or as not exhibiting overexpression of SHMT2. In some embodiments expression levels of SHMT2 are of use to distinguish between tumor cells that are likely to sensitive or less likely to be sensitive to GCS inhibition. For example, in some embodiments the level of SHMT2 expression is used to predict sensitivity of a tumor cell, tumor cell line, or tumor to GCS inhibition. In some embodiments a tumor cell, tumor cell line, or tumor that overexpresses SHMT2 is classified as having an increased likelihood of being sensitive to inhibition of the GCS. In some embodiments a subject in need of treatment for a tumor that overexpresses SHMT2 is classified as having an increased likelihood of being a suitable candidate for treatment with an inhibitor of the GCS, e.g., the subject is classified as having an increased likelihood of benefiting from treatment with a GCS inhibitor.

In some embodiments a method of classifying a tumor comprises: (a) determining whether the tumor is of a type that has a tendency to overexpress SHMT2; and (b) classifying the tumor based on results of step (a). In some embodiments a tumor type that has a tendency to overexpress SHMT2 is a brain tumor, bladder tumor, breast tumor, cervical tumor, colorectal tumor, embryonal tumor, gastric tumor, germ cell tumor, head and neck tumor, hematologic tumor, kidney tumor, melanoma, mesothelial tumor, ovarian tumor, yolk sac tumor, or sarcoma. In some embodiments a breast tumor is a triple negative breast tumor. In some embodiments the method further comprises assessing SHMT2 expression in the tumor.

In general, any cell, cell line, or tumor from which a suitable sample is available may be assessed for SHMT2 expression or activity (and/or used one or more purposes described herein). Numerous tumor cell lines and non-tumorigenic cell lines are known in the art. Cell lines may be obtained, e.g., from depositories or cell banks such as those listed above. Exemplary tumor cell lines and tumors that overexpress SHMT2 or that do not overexpress SHMT2 are described in the Examples.

As used herein "overexpression" or "overexpressed" are used interchangeably to refer to a level of expression (e.g., an amount of a gene product, such as mRNA or protein, produced or present) that is greater than, e.g., at least about 1.5, 2, 3, 4, 5, 6, 7, 8, 9, 10-fold or more higher than, a reference level or control level. However, in some embodiments, overexpression may refer to a level between 1.1 and 1.5-fold higher than a reference or control level. In some embodiments a control level is a level in normal (non-tumor) cells or non-tumor tissue. In some embodiments non-tumor tissue is tissue adjacent to a tumor. In some embodiments non-tumor tissue is tissue of the same tissue type as that from which a tumor arose. In some embodiments non-tumor cells are cells present in non-tumor tissue, e.g., non-tumor tissue adjacent to a tumor. In some embodiments a gene is overexpressed in a tumor cell, tumor cell line, or tumor, if expression is detectably greater than background in the tumor cell, tumor cell line, or tumor, and is not detectably greater than background in control cells. In some embodiments overexpression of SHMT2 refers to an expression level at least about 50%, 60%, 70%, 80%, 90%, or 100% as high as that present in cells of the U-251, BT145, 0308, A2058, ACHN, or LN229 cell line (or an average expression level of these cell lines), where, for those cell lines that can be induced to differentiate by culturing under particular conditions, the expression of SHMT2 is measured in cells cultured under non-differentiation-inducing conditions. In some embodiments overexpression of SHMT2 refers to an expression level at least about 50%, 60%, 70%, 80%, 90%, or 100% as high as that present in any one or more of the cancers listed in Table 1. In some embodiments a level of SHMT2 expression at or below the level of expression exhibited by MCF7, HMC-1-8, U87, PC3, DoTc2-4510, or exhibited by BT145 or 0308 when induced to differentiate, represents a lack of overexpression of SHMT2.

Figure 6:
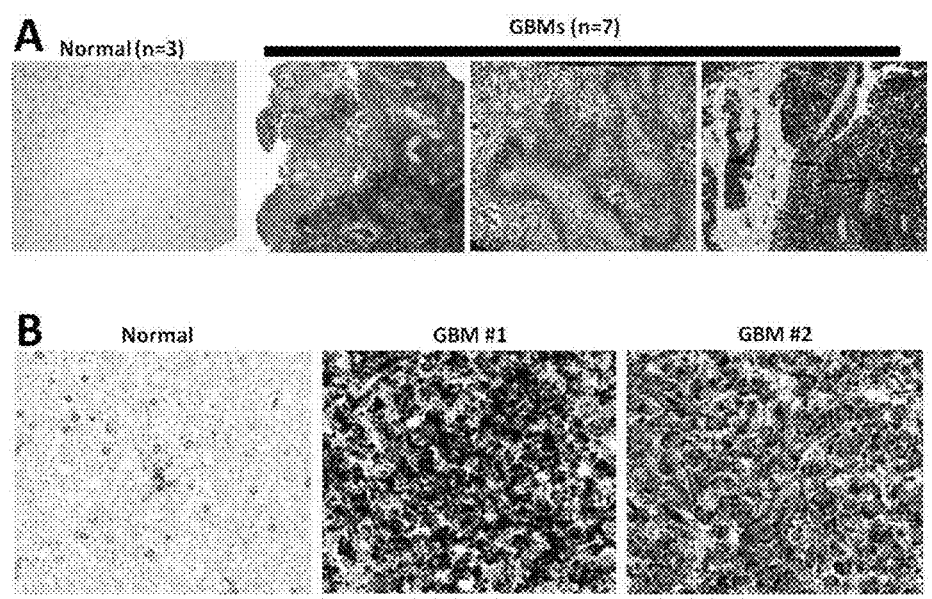
FIGS. 6A-6B. SHMT2 protein expression is elevated in GBM. (A) IHC micrograph of a representative normal brain (white matter region) and three representative GBM tumors. The three images represent the range of signal that is observed across 7 GBMs. Fields of view are at 100× magnification. (B) High magnification micrographs showing cytoplasmic punctate staining pattern of SHMT2 in normal brain and GBM tumors. In some cells in GBM, the signal is so strong that individual punctae are not easily distinguished. DAB incubation times were identical for all samples. Fields of view are at 600× magnification.

In some embodiments assessing the level of SHMT2 expression comprises determining whether at least some tumor cells overexpress SHMT2 or assessing the percentage of tumor cells that overexpress SHMT2. In some embodiments a tumor may be considered to overexpress SHMT2 if at least about 10%, 20%, 30%, 40%, 50%, or more of the tumor cells analyzed overexpress SHMT2. In some embodiments at least about 50%, 60%, 70%, 80%, 90%, or more of tumor cells overexpress SHMT2. In some embodiments at least about 50%, 60%, 70%, 80%, 90%, or more of tumor cells exhibit intense staining for SHMT2. FIG. 6 shows representative examples of brain tumor (GBM) sections exhibiting overexpression of SHMT2 and normal brain tissue (representative of tissue that does not overexpress SHMT2). In some embodiments a cell overexpresses SHMT2 sufficiently strongly such that individual punctae are not easily distinguished by IHC performed using conditions in which such punctae would be readily distinguished in non-cancer control cells that express SHMT2.

In some embodiments a method comprises assessing the level of SHMT2 expression by determining the level of an SHMT2 gene product in a sample, e.g., a tumor sample. Thus in some embodiments methods for classifying a tumor sample according to the level of an SHMT2 gene product in the sample are provided. In some embodiments, a method of classifying a tumor sample comprises steps of: (a) providing a tumor sample; and (b) assessing SHMT2 expression in the tumor sample, wherein the level of SHMT2 expression is correlated with sensitivity to GCS inhibitor, thereby classifying the tumor sample with respect to sensitivity to a GCS inhibitor. In some aspects, a method of classifying a tumor comprises: (a) determining the level of SHMT2 expression in a sample obtained from the tumor; (b) comparing the level of SHMT2 expression with a control level of SHMT2 expression; and (c) classifying the tumor with respect to the likelihood that the tumor is sensitive to a GCS inhibitor based on the result of step (b), wherein a greater (increased) level of SHMT2 gene expression in the sample as compared with the control level of SHMT2 expression is indicative of an increased likelihood that the tumor is sensitive to a GCS inhibitor.

In some aspects a method for tumor diagnosis, prognosis, prediction, or treatment selection comprises assessing the level of SHMT2 expression in the tumor. In some aspects a method for tumor diagnosis, prognosis, prediction, or treatment selection comprises: (a) assessing the level of SHMT2 expression in a tumor; and (b) providing diagnostic, prognostic, predictive, or treatment selection information based at least in part on step (a). In some aspects a method for tumor diagnosis, prognosis, prediction, or treatment selection comprises: (a) providing a tumor sample obtained from a subject; (b) assessing the level of SHMT2 expression in the sample; and (c) providing diagnostic, prognostic, predictive, or treatment selection information based at least in part on step (a). A method may further comprise scoring the sample or tumor based on the level of SHMT2 expression. The score may be used to provide diagnostic, prognostic, predictive, or treatment selection information. In some embodiments diagnostic information comprises diagnosing the presence of a tumor. For example, the presence of cells that express or overexpress SHMT2 in a location or sample that would not normally (in the absence of a tumor) be expected to contain such cells may be indicative of a tumor, or the presence of an increased number of cells that overexpress SHMT2 as compared with the number of such cells that would be expected normally (in the absence of a tumor) may be indicative of a tumor.

In some embodiments it is envisioned that the presence or level of SHMT2 expression may correlate with prognosis, e.g., outcome, independent of a particular treatment. For example, tumors that overexpress SHMT2 may, in general, be more aggressive, be more likely to result in a poor outcome when treated using standard therapy, and/or be more likely to recur after treatment using standard therapy than tumors that do not overexpress SHMT2. Outcome may be assessed, e.g., by disease-free survival, overall survival (e.g., 1, 2, 5, or 10 year survival post-diagnosis). Such a correlation may be established by analysis of SHMT2 expression in tumor samples from a cohort of patients for whom outcome data are available. Subjects may be classified into groups based on SHMT2 expression in tumor samples from the subjects and appropriate analysis, e.g., appropriate statistical analysis, may be performed to detect a difference between groups. For example, Kaplan-Meier analysis may be used.

In some embodiments predictive information comprises predicting the likelihood that a tumor will be sensitive to a GCS inhibitor (will respond to a GCS inhibitor), wherein increased SHMT2 expression indicates an increased likelihood that the tumor will be sensitive to a GCS inhibitor. In some aspects, methods of predicting the likelihood that a tumor cellor tumor is sensitive to a GCS inhibitor, are provided, the methods comprising determining whether the tumor cell or tumor overexpresses SHMT2, wherein if the tumor cell or tumor overexpresses SHMT2, the tumor cell or tumor has increased likelihood of being sensitive to a GCS inhibitor than if the tumor cell or tumor does not overexpress SHMT2.

In some aspects, methods of use to identify a subject who is a suitable candidate for therapy with a GCS inhibitor are provided, the methods comprising assessing the level of SHMT2 expression in a tumor sample obtained from a subject having cancer, wherein an increased level of SHMT2 expression indicates that the subject is a suitable candidate for treatment with a GCS inhibitor. In some embodiments a method of selecting a treatment for a subject in need of treatment for cancer comprises (a) assessing the level of SHMT2 expression in a tumor sample obtained from a subject having cancer; and (b) selecting a therapeutic agent for the subject based at least in part on the result of step (a). In some embodiments a method of selecting a treatment for a subject in need of treatment for cancer comprises (a) assessing the level of SHMT2 expression in a tumor sample obtained from the subject; and (b) selecting a GCS inhibitor as a therapeutic agent for a subject if the tumor overexpresses SHMT2. In some embodiments the method further comprises treating the subject with a GCS inhibitor. In some embodiments a method of treating a subject comprises: (a) providing a subject in need of treatment for a tumor that has been determined to overexpress SHMT2; and (b) treating the subject with a GCS inhibitor.

In some embodiments a method comprises: (a) determining that a subject is in need of treatment for a tumor that overexpresses SHMT2; and (b) treating the subject with a GCS inhibitor. In some embodiments a method comprises: (a) determining that a subject with cancer is a suitable candidate for treatment with a GCS inhibitor, based at least in part on the level of SHMT2 expression in the cancer; and (b) treating the subject with a GCS inhibitor.

In some aspects a method of assessing efficacy of treatment of cancer is provided, the method comprising: (a) assessing the level of SHMT2 expression or SHMT2 activity in a sample obtained from a subject who has been treated for cancer, wherein absence of increased SHMT2 expression or absence of increased SHMT2 activity in the sample indicates effective treatment. In some embodiments, step (a) is repeated at one or more time points following treatment of the subject for cancer, wherein continued absence of increased SHMT2 expression or increased SHMT2 activity of over time indicates effective treatment. The sample may be obtained, for example, from or close to the site of a tumor that was treated (e.g., from or near a site from which a tumor was removed). The tumor may have originally been determined to overexpress SHMT2.

In some aspects a method of assessing efficacy of treatment of cancer is provided, the method comprising: (a) assessing the level of SHMT2 expression or SHMT2 activity in a sample obtained from a subject having cancer, and (b) repeating step (a) at one or more time points during treatment of the subject, wherein decreased SHMT2 expression or decreased SHMT2 activity of over time or maintained reduction in SHMT2 expression or activity over time indicates effective treatment. The sample may be obtained, for example, from or close to the site of a cancer being treated. The tumor may have originally been determined to comprise at least some cells that overexpress SHMT2.

In some aspects a method of monitoring a subject for tumor recurrence is provided, the method comprising: (a) assessing the level of SHMT2 expression or SHMT2 activity in a sample obtained from a subject that has been treated for a tumor, wherein presence of increased SHMT2 expression or increased SHMT2 activity in the sample indicates tumor recurrence. In some embodiments, step (a) is repeated at one or more time points following treatment. The sample may be obtained, for example, from or near the site of a tumor (e.g., from or near a site from which a tumor was removed).

In some embodiments the level of SHMT2 expression may be assessed by assessing the level of an SHMT2 gene product, e.g., RNA or protein. Any suitable method known in the art useful for assessing gene products, e.g., RNA or proteins, may be used in various embodiments. In some embodiments RNA is measured based at least in part on hybridization, amplification, and/or sequencing. Exemplary methods of use to detect RNA, e.g., mRNA, include in situ hybridization, Northern blots, microarray hybridization (e.g., using cDNA or oligonucleotide microarrays), reverse transcription PCR (e.g., real-time reverse transcription PCR; quantitative RT-PCR), reverse transcription followed by sequencing, nanostring technology (Geiss, G., et al., Nature Biotechnology (2008), 26, 317-325), flow cytometry, etc. The TaqMan® assay and the SYBR® Green PCR assay are commonly used real-time PCR techniques. Other assays include the Standardized (Sta) RT-PCR™ (Gene Express, Inc., Toledo, Ohio) and QuantiGene® (Panomics, Inc., Fremont, Calif.). A number of these methods include a step of contacting a sample with one or more nucleic acid probe(s) or primer(s) comprising a sequence (e.g., at least 10 nucleotides in length, e.g., at least 12, 15, 20, or 25 nucleotides in length) substantially or perfectly complementary to a target RNA whose level is to be measured. A probe or primer may be labeled, e.g., with a fluorescent dye. In many embodiments a probe or primer comprises a sequence that is sufficiently complementary to an mRNA of interest to allow the probe or primer to distinguish between such mRNA and most or essentially all (e.g., at least 99%, or more) transcripts from other genes in a mammalian cell, e.g., a human cell, under the conditions of an assay. Primers may be designed using methods and software programs known in the art. For example, PrimerBlast, a program available at the NCBI website that makes use of the algorithm Primer3 (Rozen, S and Skaletsky, H J (2000) Primer3 on the WWW for general users and for biologist programmers. In: Krawetz S, Misener S (eds) Bioinformatics Methods and Protocols: Methods in Molecular Biology. Humana Press, Totowa, N.J.)), may be used. A probe or primer may be attached to a support or may be in solution in various embodiments. A support may be a substantially planar support, e.g., a slide or chip, or a particulate support, e.g., an approximately spherical support such as a microparticle (also referred to as a "bead"). In some embodiments a sequencing-based approach such as serial analysis of gene expression (SAGE) (including variants thereof) or RNA-Seq may be used. RNA-Seq refers to the use of any of a variety of high throughput sequencing techniques to quantify RNA transcripts (see, e.g., Wang, Z., et al. Nature Reviews Genetics (2009), 10, 57-63). Other methods of use for detecting RNA include, e.g., electrochemical detection or fluorescence-correlation spectroscopy. It will be understood that certain methods that detect mRNA may, in some instances, also detect at least some pre-mRNA transcript(s), transcript processing intermediates, non-coding transcript variants, and/or degradation products.

In some embodiments increased copy number of a chromosomal region containing at least a portion of the SHMT2 gene may be used as an indicator of overexpression. In some embodiments copy number of a region is considered increased if more than 2 copies of the region per cell are present in at least 10%, 20%, 30%, 40%, 50%, 60%, 70%, 80%, 90%, 95%, or more of tumor cells in a tumor or tumor cell line. In some embodiments, copy number may be at least 3, 4, 5, 8, 10, or 15. In some embodiments copy number of a region is considered decreased if less than 2 copies of the region per cell are present in at least 10%, 20%, 30%, 40%, 50%, or more of tumor cells in a tumor or tumor cell line. Methods useful for assessing copy number include, e.g., fluorescence in situ hybridization (FISH), multiplex ligation-dependent probe amplification, quantitative multiplex PCR of short fluorescent fragments (QMPSF), comparative genomic hybridization, array comparative genomic hybridization, SNP array technologies, DNA sequencing, etc.

In general, any method suitable for detecting and/or measuring proteins may be used to assess the level of SHMT2 polypeptide in various embodiments. For example, an immunological method or other affinity-based method may be used. Immunological detection methods generally involve detecting specific antibody-antigen interactions, e.g., in a sample. An antibody may be monoclonal or polyclonal. An antibody preparation may comprise multiple monoclonal antibodies, which may have been generated using the same or different portions of a polypeptide of interest as immunogens or binding targets. In some embodiments an antibody is an anti-peptide antibody. In some embodiments an antibody, e.g., an antibody that binds to an antigen (primary antibody) or a secondary antibody that binds to the primary antibody, has been tagged or conjugated with a label. In general, a label (also referred to as a "detectable label") may be any moiety that facilitates detection and, optionally, quantification, of an entity that comprises it or to which it is attached. Labels that may be used in various embodiments include, e.g., organic materials (including small molecule dye fluorophores, quenchers, polymers, fluorescent proteins); inorganic materials such as metal chelates, colloidal metal, metal and semiconductor nanocrystals (e.g., quantum dots); compounds that exhibit luminescensce upon enzymatic catalysis such as naturally occurring or synthetic luciferins (e.g., firefly or Renilla luciferin, coelenterazine), haptens, radioactive atoms, isotopes, or enzymes. Fluorescent dyes include, e.g., acridine dyes; Alexa dyes; BODIPY, coumain, cyanine dyes; fluorescein dyes, rhodamine dyes, xanthene dyes, and derivatives of any of the foregoing. See, e.g., The Handbook—A Guide to Fluorescent Probes and Labeling Technologies, 10th edition (Invitrogen Corp.), which describes numerous fluorescent and otherwise detectable molecules and methods for their use and modification. Enzymes include, e.g., luciferase, beta-galactosidase, horseradish peroxidase, alkaline phosphatase. A label may be directly detectable or indirectly detectable in various embodiments. For example, a fluorescent dye would be directly detectable, whereas an enzyme may be indirectly detectable, e.g., the enzyme reacts with a substrate to generate a directly detectable signal. In some embodiments a label-free detection method may be used.

Exemplary immunological detection methods include, e.g., immunohistochemistry (IHC) which term generally refers to the immunologically based detection of a tissue or cellular constituent in a tissue or cell sample; enzyme-linked immunosorbent assay (ELISA), bead-based assays such as the Luminex® assay platform (Invitrogen), protein microarrays, surface plasmon resonance assays (e.g., using BiaCore® technology), microcantilevers, immunoprecipitation, Western blot, flow cytometry. Traditional ELISA assays typically involve use of primary or secondary antibodies that are linked to an enzyme, which acts on a substrate to produce a detectable signal (e.g., production of a colored product) to indicate the presence of antigen or other analyte. As used herein, the term "ELISA" also encompasses use of non-enzymatic reporters such as fluorogenic, electrochemiluminescent, or real-time PCR reporters that generate quantifiable signals. It will be appreciated that the term "ELISA" encompasses a number of variations such as "indirect", "sandwich", "competitive", and "reverse" ELISA. As used herein, IHC is considered to encompass immunocytochemistry (ICC), which term generally refers to the immunological detection of a cellular constituent in isolated cells that essentially lack extracellular matrix components and tissue microarchitecture that would typically be present in a tissue sample. In some embodiments, e.g., in some embodiments in which IHC is used, a sample is in the form of a tissue section, which may be a fixed or a fresh (e.g., fresh frozen) tissue section or cell smear in various embodiments. A sample, e.g., a tissue section, may be embedded, e.g., in paraffin or a synthetic resin or combination thereof. A sample, e.g., a tissue section, may be fixed using a suitable fixative such as a formalin-based fixative. A section may be a paraffin-embedded, formalin-fixed tissue section. A section may be deparaffinized (a process in which paraffin or other substance in which the tissue section has been embedded is removed at least sufficiently to allow staining of a portion of the tissue section). To facilitate the immunological reaction of antibodies with antigens in fixed tissue or cells it may be helpful to unmask or "retrieve" the antigens through pretreatment of the sample. A variety of antigen retrieval procedures (sometimes called antigen recovery), may be used, e.g., in IHC. Such methods may include, for example, applying heat (optionally with pressure) and/or treating with various proteolytic enzymes. Methods can include microwave oven irradiation, combined microwave oven irradiation and proteolytic enzyme digestion, pressure cooker heating, autoclave heating, water bath heating, steamer heating, high temperature incubator, etc. To reduce background staining in IHC, the sample may be incubated with a buffer that blocks the reactive sites to which the primary or secondary antibodies may otherwise bind. Common blocking buffers include, e.g., normal serum, non-fat dry milk, bovine serum albumin (BSA), or gelatin, and various commercial blocking buffers. After immunological staining, a second stain may be applied, e.g., to provide contrast that helps the primary stain stand out. Such a stain may be referred to as a "counterstain". Such stains may show specificity for discrete cellular compartments or antigens or stain the whole cell. Examples of commonly used counterstains include, e.g., hematoxylin, Hoechst stain, or DAPI. In some embodiments an affinity-based method may use a non-antibody ligand of other specific binding agent as a detection reagent, e.g., in place of an antibody. In some embodiments cell imaging, optionally computer-aided, may be used to detect and, optionally, measure, SHMT2 mRNA or polypeptide. CellProfiler is an exemplary cell image analysis program.

In some embodiments a method comprises assessing at least one SHMT2 isoform or at least one transcript encoding an SHMT2 isoform. In some embodiments at least SHMT2 mitochondrial isoform 1, SHMT2 mitochondrial isoform 1 precursor or a transcript encoding SHMT2 mitochondrial isoform 1 precursor is assessed. In some embodiments at least SHMT2 mitochondrial isoform 2, SHMT2 mitochondrial isoform 2 precursor, or a transcript encoding SHMT2 mitochondrial isoform 2 precursor is assessed. In some embodiments at least SHMT2 mitochondrial isoform 3, SHMT2 mitochondrial isoform 3, or a transcript encoding SHMT2 mitochondrial isoform 3 is assessed. Suitable reagents, e.g., probes, primers, antibodies, capable of detecting specific isoforms or transcripts or multiple isoforms or transcripts may be used. For example, in various embodiments a binding agent, e.g., an antibody that binds to one, more than one, or all isoforms is used. In various embodiments a probe or primer that binds to one, more than one, or all transcript variants is used.

Various antibodies that specifically bind to SHMT2, e.g., human SHMT2, are commercially available, e.g., from Sigma-Aldrich (3050 Spruce St., St. Louis, Mo. 63103), e.g., catalog numbers HPA020543, HPA020549 AV46129, AV46128. One of ordinary skill in the art would readily be able to generate additional antibodies suitable for use to detect SHMT2 polypeptide. In some embodiments an antibody capable of detecting SHMT2 in tissue sections is used.

In some embodiments, an antibody (or other affinity reagent) or procedure for use to detect SHMT2 may be validated, if desired, by showing that a classification, e.g., a classification of tumors, obtained using the antibody or procedure correlates with a characteristic of interest such as tumor sensitivity to a GCS inhibitor in an appropriate set of samples. For example, an antibody may be validated for use in IHC for detection of SHMT2 and classification of samples and subjects into different categories correlated with sensitivity to a GCS inhibitor. In some embodiments, an antibody or antibody preparation or a protocol or procedure for performing IHC may be validated by establishing that its use provides similar results to those obtained using an antibody or procedure described in the Examples on an appropriate set of test samples. For example, an antibody or antibody preparation or a procedure may be validated by establishing that its use results in the same classification (concordant classification) of at least 80%, 85%, 90%, 95% or more of samples in an appropriate set of test samples as is obtained using an antibody described in the Examples. Once a particular antibody or procedure is validated, it can be used to validate additional antibodies or procedures. Likewise, a probe, primer, microarray, or other reagent(s) or procedure(s) to detect SHMT2 RNA may be validated, if desired, by showing that a classification obtained using the reagent or procedure correlates with a characteristic of interest, such as sensitivity to a GCS inhibitor, in an appropriate set of samples.

In some embodiments SHMT2 mRNA or protein level may be used together with levels of one or more other (e.g., up to 10) other mRNAs or proteins that are selected for their utility for classification for diagnostic, prognostic, predictive, or treatment selection purposes in one or more types of cancer. In certain embodiments SHMT2 expression, e.g., the level of SHMT2 mRNA or protein, is not measured or analyzed merely as a contributor to a cluster analysis, dendrogram, or heatmap based on gene expression profiling in which expression at least 20; 50; 100; 500; 1,000, or more genes is assessed. In certain embodiments, if SHMT2 mRNA or protein level is measured as part of such a gene expression profile, the level of SHMT2 mRNA or protein is used to classify samples or tumors (e.g., for diagnostic, prognostic, predictive, or treatment selection purposes) in a manner that is distinct from the manner in which the expression of many or most other genes in the gene expression profile are used. For example, the level of SHMT2 mRNA or polypeptide may be used independently of most or all of the other measured expression levels or may be weighted more strongly than many or most other mRNAs or protein in analyzing or using the results.

In some embodiments measuring the level of SHMT2 protein may comprise measuring SHMT2 activity. For example, SHMT2 activity in converting serine to glycine can be assessed (see, e.g., reference 8). In some embodiments, glycine level and/or glycine production by tumor cells or by a tumor may be assessed. In some embodiments, glycine level is measured in one or more sample(s) obtained from a subject. A sample may be a fluid sample, such as blood, cerebrospinal fluid (CSF), urine, sputum, bronchialveolar lavage, aspirate fine needle biopsy aspirate or, in some embodiments, a tissue sample, e.g., biopsy sample or surgical sample. In some embodiments, an elevated glycine level (as compared with normal glycine levels) may indicate that a subject has a tumor that is sensitive to GCS inhibition. In some embodiments an in vivo method maybe used to measure SHMT2 activity. For example, magnetic resonance spectroscopy may be used to detect glycine, e.g., elevated glycine in vivo (e.g., in the region of a tumor) or ex vivo (e.g., in a sample obtained from a subject).

Suitable controls and normalization procedures maybe used to accurately quantify SHMT2 expression or activity, where appropriate. For example, measured values may be normalized based on the expression of one or more RNAs or polypeptides whose expression is not expected to vary significantly between tumors. In some embodiments expression is normalized based on expression of a housekeeping gene. In some embodiments a housekeeping gene is a structural gene such as actin, e.g., beta-actin. In some embodiments, a measured value may be normalized to account for the fact that different samples may contain different proportions of a cell type of interest, e.g., cancer cells, versus non-cancer cells. For example, in some embodiments, the percentage of various cell types (which may be tumor or non-tumor cells) can be assessed by detecting expression of one or more cellular markers characteristically expressed by such cells. For example, stromal cells, e.g., fibroblasts, may be assessed by detecting expression of a stromal cell-specific cellular marker. Results may be adjusted to more accurately reflect mRNA or polypeptide or activity level specifically in tumor cells or in particular cellular locations. If a sample such as a tissue section contains distinguishable (e.g., based on standard histopathological criteria), areas of neoplastic and non-neoplastic tissue, such as at the margin of a tumor, the level of expression, copy number, or activity may be assessed specifically in the area of neoplastic tissue, e.g., for purposes of comparison with a control level, which may optionally be the level measured in the non-neoplastic tissue.

In some embodiments, the level of an SHMT2 gene product or the level of SHMT2 activity is determined to be "increased" or "not increased" by comparison with a suitable control level or reference level. A suitable control level may be a level that represents a normal level of SHMT2 gene product or SHMT2 activity, e.g., a level of SHMT2 gene product or SHMT2 activity in non-diseased cells or tissue. Any method that includes a step of (a) assessing the level of SHMT2 expression or activity may comprise a step of (b) comparing the level of SHMT2 expression or activity with a control level of SHMT2 expression or activity, wherein if the level determined in (a) is greater than the control level, then the level determined in (a) is considered to be "increased" (or, if the level determined in (a) is not greater than the control level, then the level determined in (a) is considered to be "not increased". For example, if a tumor has an increased level of SHMT2 expression or activity as compared to a control level, the tumor is classified as having an increased likelihood of being sensitive to a GCS inhibitor, while if the tumor does not have a significantly increased level of SHMT2 relative to a control level, the tumor is classified as having a decreased likelihood of being sensitive to a GCS inhibitor. A control level may be determined in a variety of ways. In some embodiments a control level is an absolute level. In some embodiments a control level is a relative level, such as the percentage of tumor cells exhibiting SHMT2 staining or the percentage of tumor cells exhibiting intense staining for SHMT2. A comparison may be performed in various ways. For example, in some embodiments one or more samples are obtained from a tumor, and one or more samples are obtained from nearby normal (non-tumor) tissue composed of similar cell types from the same patient. The relative level of SHMT2 gene product or SHMT2 activity in the tumor sample(s) versus the non-tumor sample(s) is determined. In some embodiments, if the relative level (ratio) of SHMT2 gene product in the tumor samples versus the non-tumor sample(s) is greater than a predetermined value (indicating that cells of the tumor have increased SHMT2), the tumor is classified as likely to be sensitive to a GCS inhibitor. In some embodiments the predetermined value may be, e.g., at least 1.5, 2, 2.5, 3, 5, 10, 20, or more. A control level may be a historical measurement. It will be understood that in at least some embodiments a value may be semi-quantitative, qualitative or approximate. For example, visual inspection (e.g., using light microscopy) of a stained IHC sample can provide an assessment of the level of SHMT2 expression or activity without necessarily counting cells or precisely quantifying the intensity of staining. Certain methods are stated herein mainly in terms of conclusions or predictions that may be drawn or made if SHMT2 expression is increased (overexpressed). Methods could be stated in terms of conclusions or predictions that may be drawn or made if SHMT2 expression is not increased. For example, if SHMT2 expression is absent the tumor may be classified as not having an increased likelihood of being sensitive to a GCS inhibitor.

For purposes of description herein it is assumed that a control or reference level represents normal levels of SHMT2 expression or activity present in non-cancer cells and tissues. However, a level of SHMT2 expression or SHMT2 activity characteristic of a GCS inhibitor-sensitive cancer may be used as a reference or control level in some embodiments. In that case, the presence of SHMT2 expression or SHMT2 activity at a level comparable to, e.g., approximately the same, as or greater than the control level would be indicative of the presence of a cancer that is likely to be sensitive to a GCS inhibitor, while a decreased level of SHMT2 expression or SHMT2 activity as compared with the control level would be predictive, e.g., of less likelihood that a tumor will be sensitive to a GCS inhibitor.

Any of the methods may, in certain embodiments, comprise assigning a score to a sample (or to a tumor from which a sample was obtained) based on the level of SHMT2 expression or SHMT2 activity measured in the sample, e.g., based on the level of an SHMT2 gene product or the level of SHMT2 activity or a combination thereof. In some embodiments two or more scores may be assigned. For example, scoring may comprise assigning a first score based on percentage of cells that express or overexpress SHMT2 and assigning a second score based on the level of expression. In some embodiments a composite score may be generated from two or more scores. A range of scores may be divided into multiple smaller ranges (subranges), and samples or tumors may be assigned differing likelihoods of being sensitive to GCS inhibition based on the subrange into which their score falls. For example, a higher score may indicate increased likelihood that a tumor will be sensitive to GCS inhibition. The number of categories in a useful scoring or classification system may be, e.g., between 2 and 10, e.g., 2, 3, or 4, although the number of categories may be greater than 10 in some embodiments.

In some embodiments a score may be assigned using a scale of 0 to X, where 0 indicates that the sample is "negative" for SHMT2 (e.g., no detectable SHMT2 polypeptide), and X is a number that represents strong (high intensity) staining in the majority of cells. In some embodiments a score is assigned using a scale of 0, 1, or 2, where 0 indicates that the sample is negative for SHMT2 (no detectable SHMT2 protein), 1 is low level staining and 2 is strong (high intensity) staining in the majority of cells. A higher score indicates increased likelihood that a tumor will be sensitive to GCS inhibition. A score may be represented using numbers or using any suitable set of symbols or words instead of, or in combination with numbers. For example, scores can be represented as 0, 1, 2; negative, positive;

negative, low, high; −, +, ++, +++; etc. The number of categories may be, e.g., 2, 3, 4, or more.

A score may be obtained by evaluating one field or multiple fields in a cell sample or tissue sample. Multiple samples from a tumor may be evaluated in some embodiments. It will be understood that "no detectable SHMT2" may mean that the level detected, if any, is not noticeably or not significantly different to background levels. In some embodiments, at least 10, 20, 50, 100, 200, 300, 400, 500, 1000 cells, or more (e.g., tumor cells) are assessed to evaluate SHMT2 expression or activity in a sample or tumor, e.g., to assign a score to a sample or tumor.

Various methods described herein, e.g., methods of classification, diagnosis, prognosis, prediction, or treatment selection may be described in terms of samples, tumors, or subjects. Such descriptions maybe considered equivalent and freely interchangeable. For example, where reference is made herein to a method of classifying a sample, such method may be expressed as a method of classifying a tumor from which the sample was obtained. Similarly, where reference is made herein to assessing the level of SHMT2 in a sample, such method may be expressed as a method of assessing the level of SHMT2 expression in a tumor from which the sample was obtained.

One of ordinary skill in the art will appreciate that a useful diagnostic, prognostic, predictive, or treatment selection method need not be completely accurate. For example, "predicting", "predicting the likelihood", and like terms typically refer to forecast of an increased or a decreased probability that a result, outcome, event, etc., of interest exists or will occur, e.g., when particular criteria or conditions are met, as compared with the probability that such result, outcome, or event, etc., exists or will occur when such criteria or conditions are not met. "Predicting", "predicting the likelihood", and like terms do not imply or require the ability to predict with 100% accuracy and do not imply or require the ability to provide a numerical value for a likelihood (although such value may be provided in some embodiments). It will also be understood that a method for predicting the likelihood of tumor sensitivity may be used together with one or more other methods. Thus a method of predicting likelihood can be a method useful to assist in predicting likelihood in combination with one or more other methods, e.g., as part of an overall method.

Although SHMT2 expression correlates with sensitivity to GCS inhibition, tumors or tumor types that are sensitive to GCS inhibition even though they do not overexpress SHMT2 may exist. Such tumors may usefully be treated with GCS inhibitors Such tumors or tumor types may be identified by testing larger panels of tumors or tumor cell lines than have been examined to date. Furthermore, without wishing to be bound by any theory, administration of a GCS inhibitor may inhibit emergence of tumor subclones that overexpress SHMT2. If SHMT2 overexpression confers a survival or proliferation advantage on tumor cells, suppressing emergence of such subclones may be therapeutically useful. It is reasonable to expect that SHMT2 activity may be elevated in some tumors by mechanisms that do not involve increased SHMT2 expression. For example, SHMT2 may be activated by certain mutations. It is also reasonable to expect that alternate approaches to identifying tumors or tumor cell lines that are sensitive to GCS inhibition based, e.g., on expression of selected RNA or proteins other than SHMT2, may be discovered.

In some embodiments a tumor that contains only a small number of SHMT2 positive cellsor may lack evidence of SHMT2 positive cells may be usefully treated with a GCS inhibitor. For example, without wishing to be bound by any theory, tumor initiating cells may have an increased likelihood of being SHMT2 positive (e.g., overexpressing SHMT2). A GCS inhibitor may be useful in eliminating tumor initiating cells or inhibiting proliferation of tumor initiating cells or inhibiting emergence of additional tumor initiating cells. Tumor initiating cells may constitute only a small fraction of a tumor in vivo. In some embodiments a GCS inhibitor may be used to specifically inhibit this subpopulation of tumor cells, optionally in combination with an agent that inhibits the bulk tumor cell population. In some embodiments treatment with a GCS inhibitor may inhibit tumor recurrence, e.g., by inhibiting survival or proliferation or emergence of tumor initiating cells. In some embodiments treatment with a GCS inhibitor may begin or continue after a tumor has been apparently eradicated, e.g., by surgery, radiation, and/or pharmacological therapy.

In some aspects, the disclosure provides a method of monitoring a subject in need of treatment for a tumor, the method comprising: (a) administering a GCS inhibitor to the subject; and (b) monitoring the subject at one or more time points after administration. In some aspects, a method of monitoring a subject in need of treatment for a tumor comprises: (a) providing a subject in need of monitoring for a tumor, the subject having been administered a GCS inhibitor; and (b) monitoring the subject at one or more time points after administration. In some embodiments the tumor overexpresses SHMT2. In some embodiments the tumor has been determined to overexpress SHMT2. In some embodiments monitoring the subject comprises monitoring for the presence of a tumor, tumor size, metastasis, or one or more symptoms, e.g., one or more symptoms associated with a tumor. Monitoring may comprise, e.g., any standard means of monitoring subjects with cancer or who have been treated for cancer, e.g., symptom assessment, physical examination, imaging, etc. Monitoring may be useful, e.g., to assess tumor sensitivity, assess tolerability of the GCS inhibitor to the subject, or select a dose level.

In some aspects, the disclosure provides methods of modulating tumor cell or tumor sensitivity to GCS inhibition, the methods comprising modulating SHMT2 expression or activity in the tumor. For example, in some embodiments sensivity of a tumor cell or tumor (e.g., a tumor cell or tumor that expresses or overexpresses SHMT2) to GCS inhibition may be decreased by inhibiting SHMT2 expression or activity in the tumor cell or tumor. In some embodiments SHMT2 expression may be inhibited using an SHMT2 inhibitor which may be, e.g., an RNAi agent targeted to SHMT2, a small molecule, antisense agent, etc. In some embodiments such inhibition may be useful, e.g., for research or testing purposes.

In some embodiments sensivity of a tumor cell or tumor (e.g., a tumor cell or tumor that does not express or overexpress SHMT2) to GCS inhibition may be increased by causing a tumor cell or tumor to overexpress SHMT2 or a functional variant thereof or by otherwise causing a tumor cell or tumor to have increased levels of SHMT2 or increased SHMT2 activity. In some embodiments causing a tumor cell or tumor to have increased SHMT2 or increased SHMT2 activity comprises delivering a nucleic acid encoding SHMT2 or a functional variant thereof to the tumor cell or tumor, e.g., by contacting the tumor cell or tumor with the nucleic acid. In some embodiments the nucleic acid is in a vector. In some embodiments causing a tumor cell or tumor to have increased SHMT2 or increased SHMT2 activity comprises delivering a polypeptide comprising SHMT2 or a functional variant to the tumor cell or tumor, e.g., by contacting the tumor cell or tumor with a polypeptide comprising SHMT2 or a functional variant thereof. In some embodiments the polypeptide comprises a protein transduction domain or mitochondrial targeting sequence. In some embodiments contacting the tumor cell or tumor comprises administering to a subject. In some embodiments an agent that causes a tumor cell or tumor to have increased SHMT2 or increased SHMT2 activity may be targeted to, expressed in, or applied directly to or in the vicinity of tumor cells or a tumor.

IV. GCS Inhibitors

In some embodiments a GCS inhibitor comprises a small molecule, nucleic acid, or polypeptide. In some embodiments a GCS inhibitor comprises an RNAi agent, an antisense oligonucleotide, or an aptamer. In some embodiments a GCS inhibitor is a direct GCS inhibitor, i.e., the GCS inhibitor acts at least in part by physically interacting with, e.g., binding to, a GCS component. For example, a GCS inhibitor may bind to an active site of a GCS protein. In some embodiments binding of a GCS inhibitor to a GCS protein inhibits binding of the natural substrate or cofactor, e.g., by sterically blocking access of the substrate or cofactor. In some embodiments it is contemplated that a GCS inhibitor may be an indirect GCS inhibitor, i.e., the GCS inhibitor may act by a mechanism that does not require physical interaction of the inhibitor with a GCS component. For example, an indirect GCS inhibitor may modulate a protein that is involved in post-translational modification or localization of a GCS protein. In some embodiments a GCS inhibitor acts at least in part in the cytoplasm. For example, in some embodiments a GCS inhibitor induces degradation or translational repression of cytoplasmic mRNA that encodes a GCS protein. In some embodiments a GCS inhibitor may interact with, e.g., bind to, a GCS protein in the cytoplasm. The inhibitor may, for example, inhibit entry of the GCS protein into mitochondria or may remain associated with and inhibit a GCS protein that enters mitochondria. In some embodiments a GCS inhibitor acts at least in part in mitochondria, e.g., the GCS inhibitor inhibits a GCS protein located in mitochondria.

In some embodiments a GCS inhibitor inhibits expression of a gene that encodes a GCS protein, so that a decreased amount of the protein is produced. In some embodiments expression of a gene encoding a GCS component is inhibited by RNAi or using an antisense oligonucleotide. For example, a cell may be contacted with an RNAi agent targeted to mRNA that encodes GLDC, GCSH, AMT, or DLD. In some embodiments an RNAi agent comprises a first portion and a second portion, wherein the first portion and the second portion form a duplex between 15-30 nucleotides in length and the first portion comprises a sequence that is at least 90% complementary to a sequence comprising at least 10, 12, 15, 17, or 19 consecutive nucleotides of a mRNA encoding a mammalian GLDC, GCSH, AMT, or DLD. In some embodiments the first portion comprises a sequence that is 100% complementary to a sequence comprising at least 10, 12, 15, 17, or 19 consecutive nucleotides of a mRNA encoding a mammalian GLDC, GCSH, AMT, or DLD. In some embodiments the first and second portions are at least 80%, 90%, or 100% complementary to each other. In some embodiments the RNAi agent is an siRNA. In some embodiments the RNAi agent is an RNAi vector. In some embodiments the the RNAi agent is a shRNA or a miRNA precursor, which may be expressed intracellularly, e.g., by cells that have taken up an RNAi vector. In some embodiments an RNAi agent is targeted to RNA that encodes a target selected from GLDC, GCSH, and AMT. In some embodiments an RNAi agent is targeted to RNA that encodes a target selected from GLDC and GCSH. Exemplary target sequences for RNAi agents that inhibit human GLDC or GCSH expression are provided in the Examples. For example, shRNA denoted G1, G4, and G5 effectively inhibited GLDC expression and were toxic to tumor cells. shRNA denoted GS1, GS2, GS3, and GS4 effectively inhibited GCSH expression and were toxic to tumor cells. In some embodiments an RNAi agent comprises a first sequence that is perfectly complementary to 18, 19, 20, or 21 continuous nucleotides of target sequence of G1, G4, G5, GS1, GS2, GS3, or GS4 and a second sequence that is perfectly complementary to the first sequence. Sequences of additional targets within mRNA encoding a GCS component and sequences of RNAi agents useful for inhibiting expression of a GCS component can be selected using, e.g., any of various known approaches useful for design of RNAi agents. In some embodiments one or more sequences may be selected to minimize "off-target" effects. For example, a sequence that has less than about 70%, 75%, 80%, 85%, 90%, or 95% complementarity to known or predicted mRNAs (other than the target GCS mRNA) of a species of interest (e.g., human) may be selected as a guide strand and/or a sequence that has less than about 70%, 75%, 80%, 85%, 90%, or 95% complementarity to known or predicted mRNAs of a species of interest may be selected as a passenger strand. In some embodiments an RNAi agent is designed so as to promote use of the strand that is complementary to (anti-sense to) RNA that encodes a GCS component as a guide strand. For example, in some embodiments an RNAi agent may be designed so that the duplex portion of the RNAi agent has lower thermodynamic stability at the 5' end of the guide strand than at the 3' end (see, e.g., Khvorova, A., et al., (2003) Cell, 115(2): 209-216). In some embodiments position-specific chemical modification may be used to reduce potential off-target effects. In some embodiments at least two different RNAi agents may be used in combination. Different RNAi agents may be targeted to the same gene or may be targeted to genes encoding different GCS components in various embodiments. In some embodiments two or more different RNAi agents targeted to GLDC are used. In some embodiments two or more different RNAi agents targeted to GCSH are used. In some embodiments one or more RNAi agents targeted to GLDC and one or more RNAi agents targeted to GCSH are used. In some embodiments RNAi agents targeted to GLDC, GCSH, and AMT are used in combination. In some embodiments up to 5, 10, or more different RNAi agents are used. RNAi agents may be used in different amounts or concentrations or in about the same amounts or concentrations in various embodiments. In some embodiments an RNAi agent may be selected at least in part empirically, e.g., to achieve a high degree of inhibition of its target and/or a high specificity. For example, multiple RNAi agents may be tested in cell culture or administered to test animals to identify one or more RNAi agents that exhibit a selected degree of silencing and/or a selected specificity for their intended target.

In some embodiments expression of a gene encoding a GCS component may be inhibited using an antisense approach. Antisense approaches encompass methods in which one or more single-stranded oligonucleotides complementary to RNA (e.g., mRNA) that encodes a protein whose inhibition is desired (e.g., a GCS protein) is contacted with cells, e.g., in a culture medium or by administration to a subject. The single-stranded oligonucleotide enters cells and hybridizes to a RNA target. Such hybridization may result in, e.g., degradation of mRNA by RNase H or blockage of translation. The oligonucleotide sequence may be about 90%, 95%, 99%, or 100% complementarity to a RNA target over at least 10, 12, 14, 16, 18, 20, 22, 24, 26, 28, or 30 nt may be selected. The oligonucleotide sequence may be selected to minimize off-target effects. For example, a sequence that has less than about 70%, 75%, 80%, 85%, 90%, 95%, 99%, or 100% complementarity to known or predicted mRNAs (other than a GCS mRNA) of a species to which the antisense agent is to be administered over at least 10, 12, 14, 16, 18, 20, 22, 24, 26, 28, or 30 nt may be selected. An antisense agent may inhibit GLDC, GCSH, AMT, or DLD. Multiple antisense agents may be contacted with cells in combination. The antisense agents may be designed to inhibit the same GCS component or different GCS components.

In some embodiments a GCS inhibitor inhibits at least one activity of a GCS component. "Activity" typically refers to the ability of an entity of interest, e.g., a GCS component, to produce an effect, e.g., on a biomolecule or on a biological system such as a cell or organism. Various activities of GCS proteins, e.g., catalytic activities, are described above. An alteration in activity, e.g., a reduction in activity (inhibition), may be measured, e.g., on a per molecule basis, per mole basis, or per weight basis of protein. In some embodiments a catalytic activity of a GCS protein is inhibited. In some embodiments, an agent is a direct inhibitor of a GCS protein. For example, a direct inhibitor may bind to GLDC, GCSH, or AMT and interfere with the enzyme's ability to catalyze a reaction and/or may prevent a substrate from entering the active site. In some embodiments a direct inhibitor is a structural analog of a substrate, a structural analog of a transition state, or a structural analog of a cofactor of an enzyme, wherein the analog is sufficiently similar in structure to a normal substrate, transition state, or cofactor to be capable of physically interacting with the enzyme but cannot, for example, be productively acted on or used by the enzyme. In some embodiments a substrate analog, transition state analog, or cofactor analog competes with a normal substrate or cofactor for binding to an enzyme.

In some embodiments a GCS inhibitor comprises a structural analog of glycine (glycine analog). In some embodiments a glycine analog may act as a substrate analog to inhibit P protein. In some embodiments a structural analog of glycine is a molecule that comprises a primary amine group and a group that substitutes for the carboxylic function of glycine. In some embodiments a group that substitutes for the carboxylic function comprises a π-electron system. For example, aminoacetonitrile (H₂NCC≡C), propargylamine (3-Amino-1-propyne; HC≡CCH2NH2), and various other glycine analogs that have a primary amine group and a π-electron system present in the group substituting for the carboxylic function were reported to inhibit the GCS (Benavides J, Biochemical Pharmacology; 32 (2):287-291 (1983)). In some embodiments a glycine analog is a molecule in which the amino group of glycine or the amino group of a glycine analog that comprises an amino group is replaced by an aminooxy (ONH₂) group. For example, carboxymethoxylamine (aminooxy) acetatic acid)) is a glycine analog reported to inhibit P protein (Gueguen, 1999, supra; Sarojini G, et al., Inhibition of glycine oxidation by carboxymethoxylamine, methoxylamine, and acethydrazide, Plant Physiol. 77(3):786-9 (1985)).

In some embodiments a GCS inhibitor comprises cysteamine (2-aminoethanethiol; chemical formula HSCH₂CH₂NH₂), a cysteamine salt, or a cysteamine derivative. Cysteamine is a known inhibitor of the GCS (Hayasaka K, Tada K. Effects of the metabolites of the branched-chain amino acids and cysteamine on the glycinecleavage system. Biochem Int 6:225-230 (1983)). Without wishing to be bound by any theory, cysteamine may act at least in part by inhibiting P protein. In some embodiments a GCS inhibitor comprises cysteamine bitartrate (also known as mercaptamine bitartrate). Cysteamine bitartrate is used clinically in the treatment of disorders of cystine excretion (cystinosis) and is available in the form of oral capsules under the trade name Cystagon™.

In some embodiments a GCS inhibitor comprises a cysteamine prodrug. In some embodiments a cysteamine prodrug comprises an agent that is capable of releasing multiple molecules of cysteamine upon cleavage of disulfide and/or amide bonds. For example, in some embodiments, a GCS inhibitor comprises cystamine (2,2'-dithiobis(ethylamine)). The disulfide bond in cystamine may be readily cleaved, e.g., in vivo, to yield two molecules of cysteamine.

In some embodiments a GCS inhibitor comprises a compound of formula I:

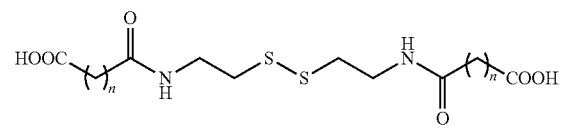

Formula I

In some embodiments a GCS inhibitor comprises a compound having the following structure:

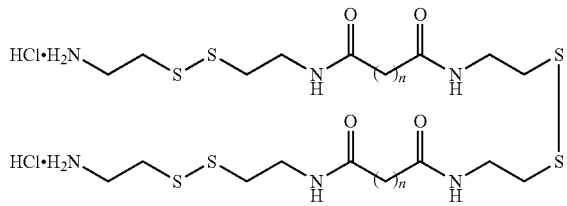

Formula II

Each instance of n in Formulas I and II can independently range, e.g., from 1 to 20, in various embodiments. Compounds of Formula I or II may act as cysteamine prodrugs.

Nephropathic cystinosis, an autosomal recessive disease characterised by raised lysosomal levels of cystine in the cells of most organs, can be treated by regular administration of cysteamine. Various prodrugs and derivatives of cysteamine or cystamine have been designed (and in at least some cases evaluated) as potential treatments for nephropathic cystinosis, including, but not limited to, certain of the compounds described above. See, e.g., McCaughan B, et al., Bioorg Med Chem Lett., 18(5):1716-9 (2008); Omran, Z., et al., Bioorg Med Chem Lett., 21(8):2502-4 (2011); Omran, Z, et al., Bioorg Med Chem. 19(11):3492-6 (2011); Omran, Z., et al., Bioorg Med Chem Lett. 21(1):45-7 (2011). In some embodiments a GCS inhibitor is a prodrug or derivative of cysteamine or cystamine has been designed and/or evaluated as a potential treatment for nephropathic cystinosis. In some embodiments a GCS inhibitor has the ability to decrease intracellular cystine in cystinotic cells, e.g., in cell culture or in animals.

In some embodiments a GCS inhibitor comprises valproic acid (CAS No. 99-66-1, also referred to as dipropylacetic acid or 2-propylpentanoic acid, among other names). Administration of valproic acid to rats has been shown to inhibit glycine cleavage activity in the liver (Kochi, et al, 1979, supra). It was suggested that the reduction in activity appeared to be due mainly to a reduced level of P protein, though P protein activity was also shown to be reduced in vitro. Administration of valproic acid to patients with NKH has been associated with an increase in seizure frequency. Without wishing to be bound by any theory, this is consistent with the notion that valproic acid, by inhibiting the GCS, causes a further reduction in residual GCS activity that may be present in these patients. In some embodiments a GCS inhibitor comprises valproate or a valproate salt. In some embodiments the valproate salt is sodium valproate. In some embodiments a GCS inhibitor is valproate semisodium, also termed divalproex sodium. Valproate semisodium is a coordination compound comprised of sodium valproate and valproic acid in a 1:1 molar relationship and is also known as sodium hydrogen bis(2-propylpentanoate). Valproate semisodium dissociates to valproate ion in the gastrointestinal tract. It is as available in an enteric coated tablet form as Depakote®. Disclosed herein are methods comprising using valproic acid, valproate, a valproate salt, or a prodrug, analog, or derivative of valproic acid or valproate, to inhibit survival or proliferation of tumor cells, e.g., in vitro or in vivo. In some embodiments, a method of inhibiting survival or proliferation of tumor cells comprises contacting tumor cells with valproic acid, valproate, a valproate salt, or a prodrug, analog, or derivative of valproic acid or valproate. In some embodiments, a method comprises administering valproic acid, valproate, a valproate salt, or a prodrug, analog, or derivative of valproic acid or valproate, to a subject in need treatment for a tumor. In certain embodiments a GCS inhibitor does not comprise valproic acid, valproate, a valproate salt, or a prodrug of valproic acid or valproate, or, in some embodiments, an analog of valproate.

In some embodiments a GCS inhibitor comprises coenzyme A (CoA) or a CoA derivative such as tiglyl CoA, isobutyryl CoA, succinyl CoA, methylmalonyl CoA, isovaleryl CoA, or propionyl CoA (Hayasaka and Tada 1983, supra).

In some embodiments a GCS inhibitor is a structural analog of folic acid or folate. In some embodiments, a folic acid or folate analog may act a substrate analog to inhibit T protein. For example, as noted above, 5-methyltetrahydrofolate (5-CH3-H4folate) is a folate analog that inhibits T protein. Other folate analogs include methotrexate, pemetrexed, raltitrexed, pralatrexate, trimethoprim, plevitrexed, GW1843, AG337, ZD1694, nolatrexed, and piritrexim. In some embodiments a folate analog is an inhibitor of an enzyme involved in folate metabolism, such as dihydrofolate reductase, β-glycinamide ribonucleotide transformylase, 5'-amino-4'-imidazolecarboxamide ribonucleotide transformylase, or thymidylate synthetase. See, e.g., Gangjee A, et al. Recent advances in classical and non-classical antifolates as anti-tumor and antiopportunistic infection agents: part I. Anti-cancer Agents Med Chem 7 (5): 524-42 (2007); Gangjee A, et al. Recent advances in classical and non-classical antifolates as anti-tumor and antiopportunistic infection agents: part II. Anti-cancer Agents Med Chem., 8(2):205-31 (2008); Hagner N and Joerger M. Cancer chemotherapy: targeting folic acid synthesis, Cancer Manag Res., 2:293-30 (2010). In certain embodiments a GCS inhibitor does not comprise an analog of folic acid or folate.

In some embodiments a GCS inhibitor is an aptamer, antibody, or non-antibody polypeptide that binds to a GCS component, e.g., GLDC, GCSH, AMT, or DLD in various embodiments. In some embodiments a GCS inhibitor comprises a single chain antibody or nanobody. Antibodies that bind to GCS proteins are known in the art and a number of such antibodies are commercially available. Additional antibodies may be produced using routine methods. In some embodiments a single chain antibody or other antibody fragment maybe generated from a full size antibody. In some embodiments a humanized antibody or antibody fragment may be used, e.g., for therapeutic purposes.

In some embodiments one or more non-antibody peptides or polypeptides that bind to targets with affinity and specificity comparable to that of antibodies may be used as GCS inhibitors. Peptides that bind to a target of interest (e.g., GLDC, GCSH, AMT, or DLD) may be identified using a variety of different procedures, such as two hybrid assays (e.g., in yeast or mammalian cells) or various display technologies such as phage display, yeast display, ribosome display, bacterial display, or mRNA display technologies, etc. In some embodiments a peptide may be selected from a peptide library, which may be, e.g., a display library or a chemically synthesized library. One or more rounds of selection (e.g., panning) may be performed to identify one or more peptides that, for example, bind to a target with sufficient specificity and affinity to be useful for one or more purposes. In some embodiments a peptide may be inserted into a supporting protein scaffold that may, e.g., enhance specificity and/or affinity by conformationally constraining the peptide. In general, a scaffold may be any of a variety of suitable proteins that have reasonable solubility. Useful scaffolds known in the art include, e.g., those based on folds from protein Z (affibodies), fibronectin (adnexins), ankyrin repeat proteins (DARPins); cysteine-knot miniproteins (knottins) or Armadillo repeat proteins or based on full-length proteins such as lipocalins (anticalins), ColE7 immunity protein (Im7), GFP, thioredoxin A, or cystatin A. A scaffold may comprise one or more alterations relative to a naturally occurring protein. For example, site(s) that potentially react with human proteins may be altered. See, e.g., or PCT/US2009/041570; Gebauer, M. and Skerra, A., Current Opinion in Chemical Biology, (2009), 13(3): 245-255; Hoffman, T., et al. Protein Eng Des Sel., 23(5):403-13, 2010, and references therein, which are incorporated herein by reference, for discussion of various proteins of use as scaffolds. The term "peptide aptamer" is sometimes used to refer to such peptides or to polypeptides comprising them. See, e.g., Colas, P., et al., Nature, 380:548-50, 1996; Bickle, M. B., et al. Nat. Protoc. 1, 1066-1091, 2006: Colas, P., J Biol. 7(1):2, 2008.

In some embodiments a polypeptide comprises a dominant negative version of a GCS component, e.g., a dominant negative version of GLDC, GCSH, AMT, or DLD. In some embodiments a dominant negative version of a protein is a variant that lacks activity or has substantially reduced functional activity relative to normal and antagonizes or interferes with function of the normal version of the protein expressed by a cell. In some embodiments adominant negative variant is a fragment of a normal protein or has an alteration in one or more amino acids (e.g., a catalytic residue) that reduces or eliminates functional activity. In some embodiments a dominant negative variant lacsk at least some amino acid(s) or domain(s) required for normal activity but retains ability to physically interact with (e.g., bind to) a substrate, cofactor, regulator, or binding partner of the normal protein. A dominant negative variant may, for example, compete with a normal version of a protein for interaction with a substrate, cofactor, regulator, or binding partner. A dominant negative variant may be capable of binding a substrate but have reduced ability to catalyze a reaction involving the substrate, as compared with the normal version of the protein. In the case of proteins that normally act as part of a complex (e.g., a dimer) a dominant negative variant may be capable of forming a complex with a normal version of the protein, but the resulting complex lacks activity or has reduced activity relative to a complex formed that comprises the normal protein and not the dominant negative variant.

In some embodiments a GCS inhibitor inhibits homodimerization of a GCS component, e.g., P protein or L protein. Exemplary methods of identifying such agents are described below.

In some embodiments binding of a GCS inhibitor to its target is non-covalent. In some embodiments it is contemplated that binding of a GCS inhibitor to its target is covalent. Inhibition of a GCS component by a GCS inhibitor may be reversible or may be essentially irreversible in various embodiments. An essentially irreversible inhibitor may be characterized in that recovery of activity of the inhibited GCS component in a system would not be detected following removal of unbound GCS inhibitor (unless additional molecules of the GCS component are synthesized or added to the system, in which case activity of such molecules may be detected). In some embodiments a GCS inhibitor that binds non-covalently may be modified to comprise a functional group capable of reacting with a GCS protein to form a covalent bond.

In some embodiments a GCS inhibitor comprises an ester, solvate, salt, or hydrate of a GCS inhibitor described above or identified as described herein.

In some embodiments a GCS inhibitor is altered, e.g., in order to modify or try to modify one or more of its properties. In some embodiments any of the methods may further comprise producing an altered GCS inhibitor and, optionally, testing the altered GCS inhibitor for activity as a GCS inhibitor or anti-tumor agent. Exemplary, properties that may be altered, and exemplary methods of alteration are described further above. Any such methods may be applied to GCS inhibitors described herein or identified as described herein. In some embodiments methods of making altered GCS inhibitors (e.g., structural analogs, GCS inhibitors attached to a second moiety) are provided.

V. Assessing Expression or Activity of GCS Components or Activity of the GCS

In some embodiments expression or activity of one or more GCS components or the overall activity of the glycine catabolism pathway catalyzed by the GCS (or the reverse pathway that results in glycine synthesis) may be assessed (e.g., detected and, optionally, measured). Such assessment may be used for any of a variety of purposes. For example, as described further below, such assessment may be used to identify, characterize, or test an agent (e.g., a GCS inhibitor). In some embodiments expression or activity of one or more GCS components or the overall activity of the glycine catabolism pathway may be used to classify a tumor cell, tumor cell line, or tumor. For example, a tumor cell, tumor cell line, or tumor may be classified as having increased or decreased expression or activity of a GCS component or of the GCS as compared to a reference, e.g., normal cells, or may be compared to other tumor cells, tumor cell lines, or tumors of the same or different tumor types.

In general, expression of GCS components can be assessed using any suitable method known in the art that is useful for assessing gene expression, e.g., for detecting or measuring specific RNAs or proteins of interest, e.g., microarrays, RNA-Seq, immunological methods. See, e.g., discussion above and Examples. In some embodiments expression of a GCS component is assessed after contacting cells with an agent known to inhibit expression of the GCS component or an agent being evaluated for, e.g., ability to modulate (e.g., inhibit) the GCS or ability to modulate (e.g., inhibit) expression of the GCS component. In some embodiments the agent is an RNAi agent. The amount of RNA or protein may be measured and may be optionally normalized and/or compared with a control value, e.g., a value expected in the absence of the agent. If the amount measured after contacting cells with the agent is less than the control value, the agent may be confirmed or identified as a GCS inhibitor or, specifically, as an inhibitor of the expression of the GCS component.

Activity of a GCS component or overall activity of the GCS may be assessed using any of variety of approaches. A number of methods that can be used to assess (e.g., detect, measure, etc.) activity of individual GCS components or combinations of two or more GCS components are known in the art. See, e.g., Sato, T., et al., Glycine metabolism by rat liver mitochondria. III. The glycine cleavage and the exchange of carboxyl carbon of glycine with bicarbonate. J. Biochem. (Tokyo). 65: 77-83 (1969); Motokawa, Y., and G. Kikuchi. Glycine metabolism by rat liver mitochondria. II. Methylene tetrahydrofolate as the direct one carbon donor in the reaction of glycine synthesis. J. Biochem. (Tokyo). 65: 71-76 (1969); Hayasaka K, et al., Purification and properties of glycine decarboxylase, a component of the glycine cleavage system, from rat liver mitochondria and immunochemical comparison of this enzyme from various sources. J Biochem. 88(4): 1193-9 (1980); Hayasaka K, et al., The mitochondrial glycine cleavage system: Purification and properties of glycine decarboxylase from chicken liver mitochondria. J Biol Chem 255:11664-11670 (1980); Hiraga K., et al., Defective glycine cleavage system in nonketotic hyperglycinemia. Occurrence of a less active glycine decarboxylase and an abnormal aminomethyl carrier protein. J Clin Invest. 68(2):525-34 (1981), Walker J L & Oliver D J. Glycine decarboxylase multienzyme complex. Purification and partial characterization from pea leaf mitochondria J Biol Chem. 15; 261(5):2214-21 (1986), for descriptions of exemplary glycine cleavage assays and assays for P, T, H, and/or L protein activity.

In some embodiments performing an assay for activity of the GCS or a GCS protein comprises (a) providing a composition comprising a GCS protein and a substrate for a reaction catalyzed by the GCS component; and (b) assessing at least one indicator of the reaction. A suitable assay, and assay details, e.g., suitable substrate(s), suitable reaction conditions, detection methods, etc., are selected as appropriate for the GCS component(s) and reaction. Assessing at least one indicator of the reaction may comprise detecting and, in some embodiments measuring, the indicator or a change in the indicator. The composition may contain one or more other ingredients such as a buffer, a salt, an antioxidant such as beta-mercaptoethanol or dithiothreitol, etc. The composition may comprise one or more co-factors or other ingredients that promote or are necessary for a reaction. The composition may comprise any one or more GCS protein(s) in various embodiments. In some embodiments a substrate is labeled. The ingredients and amounts thereof in the composition are typically selected so as to be sufficient for a reaction to occur to a detectable extent, at least in the absence of a GCS inhibitor. The composition may be provided in any suitable vessel, such as a tube, well, dish, etc. In some embodiments the assay utilizes isolated GCS protein(s), e.g., one or more at least partially purified GCS protein(s). In some embodiments the GCS protein(s) are recombinantly produced and, optionally, at least partially purified. In some embodiments human GCS component(s) are used. In some embodiments a reaction is, e.g., a glycine cleavage reaction, a glycine synthesis reaction, or any of the individual reactions described above that comprise the overall glycine cleavage reaction or glycine synthesis reaction. In some embodiments a substrate, product, or intermediate of the reaction serves as an indicator of the reaction. For example, in some embodiments an increased amount of a product, or a decreased amount of a substrate is indicative of a reaction. In some embodiments a cell-based assay is used, in which the reaction occurs in living cells, and an indicator of the reaction is then assessed. In some embodiments an indicator of the reaction is assessed in cells. In some embodiments an indicator of the reaction is assessed after lysing the cells.

In some embodiments activity of the GCS or of a GCS protein may be expressed in terms of amount of product formed or amount of substrate consumed in a given period of time per milligram (mg) of protein. For example, activity may be expressed as mol of product formed/min/mg.

In general, any suitable method and/or instrument that can detect the indicator or a change in the indicator can be used. For example, detection and/or measurement may be performed using spectroscopic, colorimetric, electrochemical (e.g., amperometric or coulometric), chromatographic (e.g., gas or liquid chromatography), optical, calorimetric, thermometric, photometric, piezoelectric, radiometric, and/or magnetic approaches in various embodiments. In certain embodiments radiation is detected using scintillation counting. In certain embodiments absorbance and/or emission of light is detected, e.g., using a spectrometer. In some embodiments a substrate or product is directly detected, thereby serving as a direct indicator of the reaction. In some embodiments a detection reagent is used as an indicator of a reaction. For example, in some embodiments a detection reagent is converted into a compound that is amenable (or more amenable) to colorimetric, fluorimetric, or chemiluminescent detection. Any of a variety of chromogenic, flourogenic, or chemiluminogenic detection reagents can be used in various embodiments. In some embodiments a detection reagent that can be readily detected without interference from one or more ingredients of an assay composition is selected. In some embodiments a coupled assay is used. For example, in some embodiments the product of a reaction catalyzed by the GCS is used as a substrate of another reaction (coupled reaction), e.g., a more readily detectable or more conveniently detectable reaction. In some embodiments the coupled reaction is catalyzed by an enzyme, in which case the assay may be referred to as a coupled enzyme assay. In some embodiments one or more reactions catalyzed by the GCS is coupled to a reaction that results in a detectable change in a detection reagent. For example, in some embodiments a product of a reaction catalyzed by the GCS serves as a substrate for a coupled reaction. In some embodiments the coupled reaction is catalyzed by a suitable enzyme. In some embodiments a first coupled reaction is coupled to one or more additional reactions, that may, for example, amplify a signal from the first coupled reaction, or result in a detectable change in a detection reagent. The detectable product is detected using a suitable detection approach and apparatus, which will generally depend at least in part on the particular product. For example, absorbance of a colored product or emission of light by a fluorescent product can be detected using a microplate reader such as the Victor2 (PerkinElmer, Newton, Mass.) or the SpectraMax M5 (Molecular Devices). In some embodiments a reaction is visually detectable, e.g., by a change in color. It will be understood that a fluorescent product is typically excited at an appropriate wavelength to cause it to emit light. In various embodiments the amount of a detectable product formed (e.g., within a specified time period) or the rate of production of a detectable product (e.g., at a specified time after starting the reaction) provides an indicator of the reaction. In various embodiments a reaction ismonitored continuously or at one or more time points. In some embodiments a reaction is assessed in the vessel in which it takes place, without requiring removal of a sample. In some embodiments one or more samples are removed from the vessel and assessed.

In some embodiments GCS activity is assessed using a glycine cleavage assay in which GCS components (P, H, T, and L proteins) and cofactors are provided, and glycine is provided as a substrate. In some embodiments, glycine cleavage may be assessed by measuring the amount of $CO_2$ that is produced when the GCS components are incubated in the presence of glycine. The glycine may be labeled, e.g., by incorporating a carbon or oxygen isotope (e.g., $C^{14}$, $O^{18}$) in the carboxyl group. Production of radiolabeled $CO_2$ can be detected, e.g., using a scintillation counter. In some embodiments, $CO_2$ is absorbed by a suitable substance (such as hyamine) or treated with one or more reactants so as to generate a liquid or solid, which may facilitate such measurements. See, e.g., Sato, et al. (1969). In some embodiments a solid state carbon dioxide sensor is used. In some embodiments glycine consumption is measured using, e.g., high performance liquid chromatography (HPLC) or Raman spectroscopy to detect glycine.

In some embodiments GCS activity is assessed by measuring glycine-dependent NADH formation (e.g., spectrophotometrically at 340 nm or fluorimetrically by excitation at 340 nm and emission at 450 nm) or disappearance of H4folate (see, e.g., Bourguignon, J., et al., Resolution and characterization of the glycine-cleavage reaction in pea leaf mitochondria: Properties of the forward reaction catalysed by glycine decarboxylase and serine hydroxymethyltransferase, Biochem J., 255, 169-178 (1988) for examples of such assays performed using GCS components from pea leaves).

In some embodiments NADH is detected and, in some embodiments measured, using a coupled assay in which NADH is oxidized to NAD+, concomitantly with the transfer of a hydride to a compound that serves as a detection reagent, followed by detection of the resulting reduced compound. In certain embodiments reduction of the detection reagent results in a detectable change, e.g., a change in a directly detectable property of the reagent. For example, in some embodiments the detection reagent, when reduced, becomes colored (or changes or loses color if it was initially colored) or becomes fluorescent (or changes its fluorescent properties (e.g., changes its emission frequency or is quenched) if it was initially fluorescent). In some embodiments the detection reagent comprises a tetrazolium salt (e.g., MTT, XTT, INT, XTS, WTS (water-soluble tetrazolium salt)), which can be reduced to yield a colored product (a formazan). In some embodiments the detection reagent comprises resazurin, which can be reduced to a fluorescent product (resofurin). In some embodiments oxidation of NADH in the coupled reaction is accomplished by a suitable NAD+ oxidoreductase, e.g., a diaphorase (e.g., EC 1.8.1.4), or by a non-enzyme electron transfer agent, such as phenazine methosulfate (PMS). In some embodiments the amount of detectable product formed provides an indicator of the amount of NADH produced and thus the activity of the GCS. In some embodiments the rate of formation of a detectable product formed provides an indicator of the rate of production of NADH and thus the activity of the GCS.

In some embodiments, a glycine exchange reaction is used, e.g., to assess activity of P and/or H proteins and/or to identify agents that inhibit activity of P and/or H protein. The glycine exchange reaction measures exchange of the glycine carboxyl carbon with the carbon atom in $CO_2$ or bicarbonate ($HCO_3^-$). For example, the amount of [$^{14}C$] bicarbonate fixed in the carbonyl carbon of glycine can be measured. The reaction does not require T protein. The glycine exchange reaction can be used to specifically measure P-protein activity when excess purified H-protein is added to the reaction. (See, e.g., Hayasaka, 1980 or Toone, JR, Biochemical and molecular investigations of patients with nonketotic hyperglycinemia. Mol Genet Metab. 70(2): 116-21 (2000)). H-protein activity can be assayed using the glycine exchange reaction in a manner similar to the assay for P-protein except that the reaction mixture is supplemented with an excess of P-protein. In some embodiments an agent that inhibits the glycine exchange reaction may be classified as an inhibitor of P protein or an inhibitor of H protein by perfoming the reaction in the presence of varying amounts of P protein and/or H protein. For example, if altering the amount of P protein does not significantly affect the reaction and/or if altering the amount of H protein does significantly affect the reaction, it may be concluded that the inhibitor does not inhibit P protein and, instead, inhibits H protein. On the other hand, if altering the amount of H protein does not significantly affect the reaction and/or if altering the amount of P protein does significantly affect the reaction, it may be concluded that the inhibitor does not inhibit H protein and, instead, inhibits P protein. In some embodiments an agent that inhibits the glycine cleavage reaction may be classified as an inhibitor of a particular GCS component by performing the reaction in the presence of the agent and varying amounts of each component, comparing the results with those obtained when the reactions are performed in the absence of the agent, and determining which set of reactions is affected by the presence of the agent. In some embodiments an agent that inhibits the glycine cleavage reaction may be classified as an inhibitor of a particular GCS component by testing the ability of the inhibitor to block CO2 production, or by testing its ability to inhibit the activity of DLD or AMT in isolation, e.g., as described below. In some embodiments an agent that inhibits the glycine cleavage reaction may be classified as an inhibitor of a particular GCS component by testing the ability of the inhibitor (e.g., a small molecule) to bind to one of the GCS components.

In some embodiments H protein activity may be assessed by following the reaction of H protein with 5,5'-dithiobis (2-nitrobenzoic acid) (Nbs) (Neuburger M, et al., Biochem J. 1991 Sep. 15; 278 (Pt 3):765-9 (1991)). In the presence of NADH, lipoamide dehydrogenase catalyses the conversion of the disulfide bond of the lipoamide into two SH groups. A large excess of Nbs, rapidly catalyses conversion of the SH groups into the disulfide bond with the formation of two molecules of 2-nitro-5-thiobenzoate (Nbs). The reaction is followed spectrophotometrically at 412 nm and H protein activity expressed as pmol Nbs formed.

T protein activity can be assessed using a variety of approaches. In some embodiments, the ability of T protein to catalzye the reverse of the reaction that it catalyzes in the glycine cleavage pathway is measured. In the reverse reaction, T protein catalyzes the synthesis of the H-protein-bound intermediate from methylenetetrahydrofolate, ammonia, and H-protein having a reduced lipoyl prosthetic group. In some embodiments T protein activity in the reverse reaction can be measured as described in Okamura-Ikeda K, et al., Mechanism of the glycine cleavage reaction. Properties of the reverse reaction catalyzed by T-protein. J Biol Chem. 15; 262(14):6746-9 (1987). The conversion of 5,10-CH2-H4folate to H4folate can be followed by measuring the decrease in absorbance at 290 nm. In some embodiments T protein activity can be assayed by measuring the synthesis of glycine from methylene-tetrahydrofolate, NH4Cl and [14C] bicarbonate in the presence of excess P-protein and H-protein, e.g., according to the method described by Motokawa, Y., and G. Kikuchi, supra (1969) or Hiraga, et al., supra (1981).

In some embodiments, ammonia (NH3), produced in the reaction catalyzed by T protein, serves as an indicator. In some embodiments ammonia is detected using a Berthelot reaction. In some embodiments ammonia is detected using a coupled assay, using, e.g., a glutamate dehydrogenase (GLDH) to catalyze a reaction in which NADH is oxidized to NAD+, thereby making possible the indirect monitoring of ammonia by, e.g., measuring the consumption of NADH. In some embodiments ammonia is detected directly, e.g., using an ion-selective probe. The consumption of NADH can be monitored at a wavelength of 340 nm or NADH can be detected using a coupled assay, e.g., as described below.

L protein utilizes dihydrolipoic acid (in H protein as a prosthetic group N-linked to a lysine residue or in the free form with diminished activity) as a hydrogen donor to catalyze the reduction of $NAD^+$ to NADH. In some embodiments, a dihydolipoamide dehydrogenase/Tris(2-carboxyethyl)phosphine (TCEP) assay in which TCEP is used as a reductant for lipoic acid can be used to measure the activity of L protein and/or H protein. This reduction can be measured, e.g., spectrophotometrically at 340 nm (see, e.g., Gueguen, V., et al. Structural and functional characterization of H protein mutants of the glycine decarboxylase complex. J. Biol. Chem. 274(37): 26344-26352 (1999); see also Zay, et al., 2011, supra).

It will be understood that the assay details described herein and/or in the references cited herein are exemplary and may be modified in any of a variety of ways. For example, different sources or amounts of GCS components and/or different labels, reagents, methods, or instruments may be used.

In some embodiments activity of a GCS component may be measured after contacting the GCS component with an agent known to inhibit activity of the GCS component or an agent being evaluated, e.g., for ability to modulate (e.g., inhibit) the GCS or ability to modulate (e.g., inhibit) activity of the GCS component. In some embodiments the agent is or comprises a small molecule. The activity measured may be compared with a control value, e.g., a value expected or obtained in the absence of the agent. If the activity measured after contacting cells with the agent is less than the control value, the agent may be confirmed or identified as a GCS inhibitor or, specifically, as an inhibitor of the activity of the GCS component.

In some embodiments aGCS inhibitor may be used at a concentration that reduces GCS activity or reduces activity of a particular GCS component to a selected amount or level or to within a selected range as assessed, e.g., using one or more of the above-mentioned assays. In some embodiments the reduction isat least about 5%, 10%, 15%, 20%, 25%, 30%, 35%, 40%, 45%, 50%, 55%, 60%, 65%, 70%, 75%, 80%, 85%, 90%, 95%, 99%, or 100% of a reference level (e.g., a control level), or any intervening range, using a suitable assay. In some embodiments the reduction is at least 5%, 10%, 15%, 20%, 25%, 30%, 35%, 40%, 45%, 50%, 55%, 60%, 65%, 70%, 75%, 80%, 85%, 90%, 95%, 99%, or 100% of a reference level (e.g., a control level). In some embodiments a reference level is a level that exists in the absence of the GCS inhibitor. In some embodiments, 100% inhibition refers to reduction to a background level.

VI. Methods of Identifying, Assessing, or Generating Agents

In some aspects, methods of identifying or assessing a candidate agent for treatment of cancer (also referred to herein as a "candidate anti-cancer agent" or "candidate anti-tumor agent") are provided. In some aspects, compositions useful for performing one or more of the methods of identifying or assessing a candidate agent for treatment of cancer are provided. In ome embodiments a method of identifying a candidate agent for treatment of cancer comprises (a) performing a screen or assay to identify an inhibitor of the GCS. In some embodiments the method further comprises testing an inhibitor identified in step (a) in a tumor model.

Any of a variety of cell-free or cell-based assays may be used to identify or assess modulators, e.g., inhibitors, of the GCS or a GCS component in various embodiments. In some embodiments a cell-free assay comprises contacting one or more GCS component(s) and an agent (e.g., a test agent) in a composition outside of a living cell. In some embodiments the composition comprises a cell lysate or one or more GCS component(s) that is/are at least partially purified or synthesized outside living cells. The GCS component(s) may be purified to a selected degree of purity. In some embodiments a composition may comprise a cytoplasmic lysate or organelle-specific lysate. In some embodiments a lysate is prepared from cells that naturally express or are engineered to express a GCS component. In some embodiments a composition may comprise membranes or membrane constituents (e.g., lipids). Such membranes or constituents may be naturally occurring (e.g., components present in mitochondria or mitochondrial membranes), artificial, or a combination thereof in various embodiments. In some embodiments a composition may comprise a subcellular organelle, e.g., mitochondria. In some embodiments the composition comprises one or more GCS protein(s) or an RNA encoding a GCS protein. In some embodiments the RNA or protein has been synthesized using recombinant nucleic acid techniques. For example, a GCS protein can be expressed in appropriate prokaryotic or eukaryotic host cells and purified.

In some embodiments an RNA or protein has a sequence that consists of or comprises a naturally occurring sequence, e.g., a normal sequence. In some embodiments the sequence of a GCS component comprises the sequence of a naturally occurring GCS component. In some embodiments a GCS component that is a variant, e.g., a functional variant, of a naturally occurring normal GCS component is used. For example, in some embodiments a polypeptide comprising a sequence at least 80%, 90%, 95%, 96%, 97%, 98%, 99% identical, or 100% identical, to a mammalian, e.g., human, GLDC, GCSH, AMT, or DLD or at least 80%, 90%, 95%, 96%, 97%, 98%, 99% identical, or 100% identical, to a functional portion of a mammalian, e.g., human, GLDC, GCSH, AMT, or DLD is used. In some embodiments a polypeptide comprising a sequence at least 80%, 90%, 95%, 96%, 97%, 98%, 99% identical, or 100% identical, to at least a catalytic domain of a mammalian, e.g., human GLDC, GCSH, or AMT is used. In some embodiments a GCS component comprising a tag is used. In some embodiments information obtained from sequence comparison, mutational analysis, analysis of naturally occurring mutants, structural analysis, may be used to generate a functional variant. In some embodiments a protein that at least in part lacks a mitochondrial targeting sequence, which sequence is found in a naturally occurring precursor protein (pre-protein) is used. In some embodiments a fragment is used. In some embodiments a fragment comprises at least a catalytic domain. A cell-based assay is an assay performed at least in part using living cells. In some embodiments a cell-based assay comprises contacting living cells that express a GCS component with a test agent) and assessing the effect of the test agent on expression or activity of the GCS component. The GCS component may be assessed in the cellular environment or may first be isolated from the cells and then assessed. The term "test agent" may be used to refer to an agent that is to be assessed, is being assessed, or has been assessed, e.g., for one or more activit(ies) or for suitability for one or more purposes, but is not to be construed as implying any limitation on the agent or its use.

In some embodiments performing an assay to identify a GCS inhibitor comprises: (a) providing a composition comprising a test agent and at least one GCS component or RNA encoding a GCS component; and (b) assessing the effect of the test agent on the GCS or on the GCS component or RNA encoding the GCS component, e.g., determining whether the test agent inhibits the GCS or inhibits the GCS component. If the test agent inhibits the GCS or GCS component the test agent is identified as a GCS inhibitor. In some embodiments, step (b) comprises assessing expression of a GCS component. In some embodiments, step (b) comprises assessing activity of a GCS component or assessing activity of the GCS. In some embodiments a method comprises: (a) identifying a GCS inhibitor; and (b) testing the GCS inhibitor identified in step (a) in at least one tumor model. In some embodiments a method for assessing a candidate anti-tumor agent comprises steps of (a) performing an assay to identify a GCS inhibitor; and (b) testing the GCS inhibitor identified in step (a) in at least one tumor model. In some embodiments a method of assessing a candidate anti-tumor agent comprises: (a) providing a GCS inhibitor; and (b) testing the GCS inhibitor in at least one tumor model. In some embodiments, testing comprises determining whether the GCS inhibitor exhibits at least one anti-tumor effect. In some embodiments of the methods, step (b) comprises (i) contacting one or more tumor cells with the GCS inhibitor; and (ii) assessing survival (viability) or proliferation of the one or more tumor cells, wherein the GCS inhibitor is confirmed as a candidate anti-cancer agent if the survival or proliferation of the one or more tumor cells is inhibited. In some embodiments a method further comprises determining whether the survival or proliferation of the one or more tumor cells is inhibited, e.g., as compared with survival or proliferation of one or more suitable control cells. A suitable control cell may be, e.g., a tumor cell that has not been contacted with the GCS inhibitor or that has been contacted with a lower amount of the GCS inhibitor. In some embodiments tumor cells are contacted with the test agent in a culture system. In some embodiments at least some of the tumor cells overexpress SHMT2.

In some embodiments a method of identifying an agent that modulates expression of a gene that encodes a GCS protein comprises (a) contacting a gene that encodes a GCS protein and a test agent; and (b) assessing the effect of the test agent on expression of the gene. In some embodiments step (b) of method of identifying an agent that modulates expression of a gene comprises assessing the level of an expression product of the gene (e.g., mRNA or protein). The level may be compared with a suitable reference level, e.g., the level that would be expected in the absence of the test agent, e.g., in the absence of an agent, or in the presence of an agent known or believed to be inactive in the system. If the level measured in step (b) differs from the reference level, the test agent is identified as a modulator of expression of the gene. For example, if the level measured in step (b) is increased or decreased as compared with the reference level, the test agent enhances or inhibits expression of the gene, respectively. In some embodiments a measured level is normalized, based, e.g., on expression of one or more suitable genes. In some embodiments expression is normalized based on expression of a gene whose expression level is not expected to be specifically affected by a test agent. In some embodiments a measured level is normalized based on expression of a structural gene.

In some embodiments, the method comprises contacting cells with the test agent and assessing the effect of the test agent on expression of the gene by the cells. The step of contacting cells with a test agent may occur in culture or in vivo in various embodiments. The cells or composition may be maintained for a suitable time period after being contacted with the test agent and prior to assessing the effect of the test agent. A suitable time period may be a time period sufficient for at least some of the gene product existing at the time of contacting to be degraded. In some embodiments the time period may be, e.g., at least 1, 4, 8, 12, 24, or 48 hours up to about 7 days, e.g., between 12 and 24 hours, between 24 and 48 hours, between 48 and 72 hours, etc. In some embodiments cells are exposed to the test agent during only part of such time period. In some embodiments cells are exposed to the test agent throughout time period. Additional test agent may be added during the time period. In some embodiments cells that naturally express the target gene may be used. In some embodiments cells that have been engineered to express a target gene or a portion thereof of that have been engineered to express a reporter gene may be used. In some embodiments an agent may be assessed for ability to inhibit expression of a target gene by RNAi. In some embodiments an RNAi agent is contacted with cells, e.g., by adding the agent to medium containing the cells, and the effect on level of the target RNA or a translation product thereof is assessed. For example, degradation of the target RNA may be detected. In some embodiments an RNAi agent is expressed intracellularly, and the effect on expression of a target gene is assessed.

Methods known in the art may be used for detecting or measuring expression products, e.g., mRNA or protein. See, e.g., discussion above for further details of assays that may be used to assess RNA or proteins. In some embodiments an assay of GCS protein activity may be used as an indicator of protein level. In some embodiments a reporter gene based assay is used. A reporter gene comprises a nucleic acid in which one or more expression control elements (e.g., at least a promoter) of a target gene are operably linked to a sequence that encodes a reporter molecule ("reporter"). For example, in some embodiments a GCS reporter gene comprises a nucleic acid in which one or more expression control elements (e.g., at least a promoter) of the GLDC, GCSH, AMT, or DLD gene are operably linked to a sequence that encodes a reporter. The level of the reporter is detected and serves as a readout that reflects transcriptional activity from the expression control element(s). Reporters may be detectable molecules, such as proteins that produce a fluorescent, luminescent, or colorimetric signal or are capable of absorbing light of a particular wavelength. In some embodiments, a reporter molecule comprises an enzyme that acts on a substrate to produce a fluorescent, luminescent, or colorimetric signal. Exemplary reporter molecules include, e.g., green, blue, sapphire, yellow, red, orange, and cyan fluorescent proteins and derivatives thereof; monomeric red fluorescent protein and derivatives such as those known as "mFruits", e.g., mCherry, mStrawberry, mTomato; enzymes such as luciferase; beta-galactosidase; horseradish peroxidase; alkaline phosphatase; etc. In some embodiments, a reporter is a secreted protein.

Agents that modulate, e.g., inhibit, activity of a GCS protein may be identified using a variety of different cell-free or cell-based assays. In some embodiments a test agent is contacted with one or more GCS protein(s), e.g., by preparing a composition comprising the test agent and the GCS protein(s). The composition may be incubated for a suitable period of time under suitable conditions to allow, e.g., binding or reaction to occur. One or more parameters are measured, e.g., binding of the test agent to the GCS protein, activity (e.g., enzymatic activity) of the GCS protein, etc. The composition may comprise other component(s) necessary or helpful for a reaction or for detecting binding or enzymatic activity or identifying a compound of interest. In some embodiments, an assay comprises determining whether a test agent binds to a GCS protein and/or quantifying one or more binding characteristics. Numerous binding assay formats are known in the art. In some embodiments, a label-free assay may be used, while in other embodiments the target or test agent may be labeled. A binding assay may include a solid phase or fluid phase binding event. The test agent, the GCS protein, an indicator of either, or an indicator of the binding event may be detected. In some embodiments a GCS protein or a test agent is attached to a support. In some embodiments a support is an article having a rigid or semi-rigid surface. In some embodiments at least one surface is substantially flat. In some embodiments a support is approximately spherical. A support may be composed of an inorganic or organic material or combination thereof. In some embodiment, a support is composed at least in part of a metal, ceramic, glass, plastic, gel, or other matrix. Such articles may, for example, take the form of plates (e.g., multiwell plates), slides, particles (e.g., "beads", e.g., magnetic beads), pellets, bars, rods, pins, disks, chips, filters, or other suitable forms. In some embodiments a support comprises a sensor, e.g., a sensor capable of detecting binding or a change in binding. For example, the sensor may detect a change in weight or a signal such as fluorescence. In some embodiments the support comprises an electrode. In some embodiments test agents may be arranged as a small molecule microarray. Test agents may be present in multiple locations on a surface, in individual wells or vessels, etc. See, e.g., Vegas A J, et al., Chem Soc Rev. 37(7):1385-94, 2008. In some embodiments a GCS protein or a test agent is noncovalently or covalently attached to the support. In some embodiments multiple test agents are immobilized in multiple locations (e.g., in an array format). A GCS protein is added and the composition is maintained for a suitable time period to allow binding to occur. In some embodiments, unbound material is removed by washing, and the GCS protein is detected. In some embodiments a washing step may be omitted. In some embodiments binding may be detected by measuring a change in fluorescence polarization, fluorescence resonance energy transfer, or electrochemiluminescence. In some embodiments a GCS protein is immobilized, test agents are added, and binding is measured using similar approaches. In some embodiments a method for screening one or more test agents to identify those that bind to a GCS component comprises steps of: (a) introducing into each of one or more reaction vessels: one or more GCS components and one or more test agents whose binding to a GCS component is to be evaluated; (b) incubating the vessels under suitable conditions and for a time sufficient to allow binding to occur; and (c) assaying for binding, thereby determining whether one or more of the test agents binds to a GCS component. Reaction vessels may be, e.g., wells of a multiwell plate. In various embodiments a screen may be performed using a single GCS component or multiple GCS components in a given vessel. In various embodiments a screen may be performed using a single test agent or multiple test agents in a given reaction vessel.

In some embodiments surface plasmon resonance (SPR) may be used to measure kinetics (on and/or off rates) and/or detect or measure binding strength (affinity) between a test agent and a GCS protein. For example, using SPR technology (e.g., systems such as those available from Biacore, Life Sciences, GE Healthcare) the binding and dissociation of a test agent to a protein immobilized on a chip can be measured, and the measured values compared with those obtained when a solution not containing the test compound is loaded on the chip. A test agent capable of binding to the protein can be selected on the basis of the binding and dissociation rate and/or binding level. Other useful methods for detecting and/or quantifying binding include use of a quartz crystal microbalance, optical cantilever, microchannel resonator, dual polarisation interferometer, coupled waveguide plasmon resonance, immunoprecipitation or other antibody-based detection methods, isothermal titration and differential scanning calorimetry, capillary electrophoresis, resonance energy transfer, electrochemiluminesce, fluorescence anisotropy or fluorescence polarization, and fluorescent correlation analysis.

In some embodiments an agent that is known to bind to a GCS protein is used as a tool for screening test agents (e.g., small molecules) for ability to bind to and/or inhibit activity of the target GCS protein. The agent that is known to bind to a target may be labeled. The label may comprise, e.g., a radioactive, fluorescent, or other detectable moiety. The ability of a test agent to compete with the labeled agent can be detected and serves as an indicator of the binding of the test agent to the target protein. In some embodiments a scintillation proximity assay (SPA) may be used. In some embodiments of an SPA for identifying agents that bind to a target protein, the target protein is attached to beads containing a scintillant material. The beads are typically located in wells or other vessels. In some embodiments a target protein is attached to scintillant material embedded directly into wells. A test agent and a radiolabeled compound capable of binding to the target protein are added to the well. Binding of the radiolabeled compound to the target protein results in a signal. The signal is reduced in the presence of a test agent that competes with the radiolabelled compound for binding. See, e.g., J. Fraser Glickman, et al., Scintillation Proximity Assays in High-Throughput Screening. Assay and Drug Development Technologies. 6(3): 433-455, 2008, for a review of SPA.

In some embodiments, a test agent that binds to a GCS protein, with a Kd equal to or less than approximately 1 mM, 500 μM, 100 μM, 50 μM, 10 μM, 5 μM, or 1 μM is identified or selected. In some embodiments a test agent that binds to a GCS protein with a Kd equal to or less than approximately 500 nM, 100 nM, 50 nM, or 10 nM is identified or selected. In some embodiments, a test agent that binds to a GCS protein with a Kd between 0.1-10 nM is identified or selected. Test agents that bind to a GCS protein may be further tested, e.g., in one or more cell-free or cell-based assays, to determine the extent to which they modulate, e.g., inhibit, activity of the target protein and/or to determine the extent to which they modulate, e.g., inhibit, overall activity of the GCS. For example, test agents that bind to a GCS protein, may be further tested, e.g., in one or more cell-free or cell-based assays, to determine the extent to which they modulate, e.g., inhibit, activity of the protein and/or overall activity of the GCS. In some embodiments the ability of a test agent to inhibit dimerization of a GCS component may be assessed. Methods of assessing protein-protein interactions, such as protein-fragment complementation assays (PCA), or FRET or BRET-based assays, SPA assays, etc.

In some embodiments performing an assay to identify a GCS inhibitor comprises: (a) providing a composition comprising a test agent, a substrate, and one or more GCS component(s); and (b) assessing the effect of the test agent on a reaction catalyzed by the one or more GCS component(s). In some embodiments the ability of a test agent to inhibit catalysis of a chemical reaction by a GCS protein is assessed. If the test agent inhibits the reaction, the test agent is identified as a GCS inhibitor. In various embodiments the reaction is any of the reactions of the GCS described above. In various embodiments the reaction is assessed using any of the methods described herein. In some embodiments a method of identifying a modulator of a GCS protein comprises (a) providing a composition comprising a GCS protein, a substrate for a reaction catalyzed by the GCSprotein, and a test agent; and (b) detecting at least one indicator of the reaction. In some embodiments the method further comprises (c) comparing the result of step (b) with a reference value and (d) identifying the test agent as a GCS modulator if the result of step (b) indicates that the test agent increased or inhibited the reaction. In some embodiments a method of identifying a GCS inhibitor comprises: (a) providing a composition comprising a test agent, a substrate, and one or more GCS protein(s); (b) measuring an indicator of a reaction catalyzed by the one or more GCS protein(s); (c) comparing the result of step (b) with a reference value; and (d) identifying the test agent as a GCS inhibitor if the result of step (c) indicates that the test agent inhibited the reaction. In various embodiments the composition comprises any one, more than one, or all of the GCS proteins. The GCS protein(s), substrate, and test agent may be provided in a suitable liquid medium. In some embodiments the liquid medium is an aqueous medium that comprises at least 50%, 60%, 70%, 80%, 90%, 95%, 96%, 97%, 98%, 99% or more water (v/v). In some embodiments a liquid medium may comprise an organic solvent such as DMSO, e.g., in an amount that does not significantly affect the activity of the target protein as compared with activity in the absence of the organic solvent. Other ingredients may be present in the composition, such as co-factors, buffer substances, etc. Buffer substances include, e.g., Tris-HCl, sodium borate, HEPES, MOPS, etc. The concentration of the substrate, GCS protein(s), other ingredients, and conditions such as pH and temperature may vary. They are typically selected so as to provide a detectable level of reaction in a reasonable time period, at least in the absence of an inhibitor of the GCS. The composition is maintained for a suitable time period under conditions that would (in the absence of a test agent that is a potential inhibitor) be appropriate for the GCS protein to catalyze a reaction in which the substrate(s) is/are converted to one or more product(s) at a detectable level. The reaction may be stopped after a selected time period by, e.g., adding an agent that stops the reaction. An indicator of the reaction is detected. In some embodiments the amount of product produced and/or the rate of product formation is determined. The effect of the test agent on the amount of product produced and/or the rate at which the product is produced is assessed, e.g., by comparison with a suitable reference value. If the amount of product or rate of product production is decreased in the presence of the test agent as compared with a suitable reference value, the test agent is considered to inhibit the ability of the GCS protein to catalyze the reaction, i.e., the test agent is considered an inhibitor of the GCS protein. In some embodiments the rate of substrate consumption or the amount of substrate consumed is determined or the amount of substrate remaining is determined. If the amount of substrate consumed or the rate of substrate consumption is decreased (or the amount of substrate remaining is increased) in the presence of the test agent as compared with a suitable reference value, the test agent is considered to inhibit the ability of the protein to catalyze the reaction, i.e., the test agent is considered an inhibitor of the protein. In some embodiments the composition comprises a detection reagent. In some embodiments at least one reaction of the GCS is coupled to a reaction in which a detection reagent undergoes a detectable change, and the change is detected as an indicator of the reaction. For example, in some embodiments the detection reagent is converted to a detectable compound, which compound is detected as an indicator of the reaction. In some embodiments a detection reagent is added after the reaction has been stopped or is combined with a sample removed from the vessel in which the reaction occurred. In some embodiments a composition comprises one or more enzymes, electron transfer agents, or other ingredients suitable for performing a coupled assay. A reference value in any of these assays may be, e.g., a value measured under similar, substantially identical, or identical assay conditions in the absence of the test agent (optionally in the presence of a vehicle or inactive agent) or in the presence of substantially lower amount of test agent than used in the assay. In general, a reference value may be a previously obtained, contemporaneously obtained, subsequently obtained, or historical value.

Various substrates and products that can be detected and measured are described above. For example, in some embodiments production of ammonia is measured. In some embodiments consumption of NAD+ or production of NADH is measured. In some embodiments production of carbon dioxide is measured. In some embodiments disappearance of glycine is measured. In some embodiments a substrate comprises a moiety that facilitates detection of a product of a reaction catalyzed by a target protein. For example, the substrate may comprise one or more labels (e.g., radioactive atoms, fluorescent labels, and/or fluorescence quenchers). In some embodiments the substrate comprises a moiety that emits a signal upon reaction of the substrate. In some embodiments the substrate comprises a moiety that can be readily detected upon release from the substrate. For example, the moiety may react with another compound to produce a colorimetric, fluorescent, or luminescent signal. In some embodiments an assay readout may be based on resonance energy transfer (RET), e.g., fluorescence resonance energy transfer (FRET), luminescence resonance energy transfer (LRET), or bioluminescence resonance energy transfer (BRET). A wide variety of RET-based assays may be implemented. In general, such assays make use of a distance-dependent interaction involving energy transfer between two moieties (sometimes termed a donor and acceptor). If both moieties are present as part of a substrate and positioned so that cleavage of the substrate releases one of the moieties, a signal (e.g., an increase or decrease in a signal) may be detected. In some embodiments one or more of the assay components is attached to or otherwise physically associated with a support. In some embodiments an enzyme is immobilized to a support or matrix such as a gel. In some embodiments a support comprises a sensor, e.g., a sensor capable of detecting an indicator of a reaction.

In general, an appropriate assay may be selected for a target of interest depending at least in part on the particular activit(ies) characteristic of the target. For example, various assays that may be used for assessing activity of GCS proteins or overall activity of the GCS are described above. In some embodiments a glycine cleavage assay may be used. In some embodiments, a glycine exchange reaction may be used, e.g., to assess activity of P and/or H proteins and/or to identify agents that inhibit activity of P and/or H protein. In some embodiments H protein activity may be measured by following the reaction of H protein with Nbs. In some embodiments, the ability of T protein to catalzye the reverse of the reaction that it catalyzes in the glycine cleavage pathway is measured. In some embodiments a dihydolipoamide dehydrogenase/Tris(2-carboxyethyl)phosphine (TCEP) assay in which TCEP is used as a reductant for lipoic acid may be used to measure the activity of L protein and/or H protein.

Embodiments are directed towards each of the assays described herein, e.g., to identify or characterize GCS inhibitors.

In some embodiments a method for screening one or more test agents to identify those that exert an effect on the GCS or a GCS component comprises steps of: (a) introducing into each of one or more reaction vessels: one or more GCS components; one or more substrates; and one or more test agents whose effect on the GCS or on a GCS component is to be evaluated; (b) incubating the vessels under suitable conditions and for a time sufficient to allow a reaction to occur; and (c) assaying for the occurrence of the reaction, thereby revealing the effect of the test agent on the GCS or on a GCS component. In some embodiments the method comprises comparing the result of step (c) with a reference value, e.g., a value obtained or expected under otherwise similar conditions in the absence of the test agent. In some embodiments the method further comprises identifying a test agent as an inhibitor of the GCS or a GCS component if the extent of the reaction as assessed in step (c) is reduced as compared with the reference value. In various embodiments a screen may be performed using a single GCS component or multiple GCS components in a given vessel. In various embodiments a screen may be performed using a single substrate or multiple substrates in a given vessel. In various embodiments a screen may be performed using a single test agent or multiple test agents in a given reaction vessel. In some embodiments, if the reaction vessel contained multiple test agents, the method further comprises testing at least some of the test agents individually to determine which one(s) exert an effet on the GCS or a GCS component. In various embodiments the number of reaction vessels and/or test agents is at least 10; 100; 1000; 10,000; 100,000, or more. In some embodiments the reaction vessels are wells of a multiwell plate.

In some embodiments, a test agent identified as a GCS modulator, e.g., a GCS inhibitor, in an initial ("primary") assay or screen may be considered a "candidate modulator". One or more "confirmatory" or "secondary" assays or screens may be performed to confirm that a test agent modulates a GCS protein or GCS activity or to measure the extent or specifity of modulation or to assess specificity. Such confirmatory testing may utilize the same assay or a different assay as that used to identify the test agent. In some embodiments a secondary assay comprises determining whether a test agent functions as a specific inhibitor of the GCS or a GCS component or as a non-specific inhibitor, e.g., of transcription, translation, or protein activity. In some embodiments a test agent that exhibits a reasonable degree of specificity for the GCS or a GCS component is identified or selected, e.g., for further testing or development or use.

A wide variety of cells may be used for one or more purposes described herein, e.g., in one or more assays or screens described herein. In some embodiments, the cells express or contain a target, e.g., a GCS gene product, either naturally or as a result of genetic modification. In some embodiments cells that do not express a target may be useful, e.g., for control purposes. A cell may originate from any organism of interest, e.g., a vertebrate, e.g., a mammal. In some embodiments, a cell is a primate cell, e.g., a human cell. A cell may be a primary cell, immortalized cell, normal cell, abnormal cell, non-tumor cell, tumor cell, etc., in various embodiments. A cell may originate from a particular tissue or organ of interest or may be of a particular cell type. In some embodiments a cell is a member of a population of cells, e.g., a non-immortalized or immortalized cell line. In some embodiments, a "cell line" refers to a population of cells that has been maintained in culture for at least 10 passages or at least 10 population doublings. In some embodiments, a cell line is derived from a single cell. In some embodiments, a cell line is derived from multiple cells. In some embodiments a cell line is derived from a sample of cells obtained from a particular individual. In some embodiments, the cells of a cell line are descended from a cell or cells originating from a single sample (e.g., a sample obtained from a tumor) or individual. A cell may be a member of a cell line that is capable of prolonged proliferation in culture (e.g., for longer than about 3 months or longer than about 25 population doublings). In some embodiments, a cell line is capable of indefinite proliferation in culture (immortalized cells). An immortalized cell line has acquired an essentially infinite life span, i.e., the cell line is capable of proliferating essentially indefinitely. For purposes hereof, a cell line that has undergone or is capable of undergoing at least 100 population doublings in culture may be considered immortal. A non-immortalized cell line may, for example, be capable of undergoing between about 20-80 population doublings in culture before senescence. In some embodiments, cells are maintained in culture and may be passaged or allowed to double once or more following their isolation from an individual (e.g., between 2-5, 5-10, 10-20, 20-50, 50-100 times, or more) prior to their use in a method disclosed herein. In some embodiments, cells have been passaged or permitted to double no more than 1, 2, 5, 10, 20, or 50 times following their isolation from an individual prior to their use in a method disclosed herein. If desired, cells may be tested to confirm whether they are derived from a single individual or a particular cell line by any of a variety of methods known in the art such as DNA fingerprinting (e.g., short tandem repeat (STR) analysis) or single nucleotide polymorphism (SNP) analysis (which may be performed using, e.g., SNP arrays (e.g., SNP chips) or sequencing).

In some embodiments a high throughput screen (HTS) is performed. A high throughput screen may utilize one or more cell-free or cell-based assays. High throughput screens often involve testing large numbers of test agents with high efficiency, e.g., in parallel. For example, tens or hundreds of thousands of agents may be routinely screened in short periods of time, e.g., hours to days. Such screening is often performed in multiwell plates (sometimes referred to as microwell or microtiter plates or microplates) containing, e.g., 96, 384, 1536, 3456, or more wells or other vessels in which multiple physically separated depressions, wells, cavities, or areas (collectively "wells") are present in or on a substrate. Different test agent(s) may be present in or added to the different wells. It will be understood that some wells may be empty, may comprise replicates, or may contain control agents or vehicle. High throughput screens may involve use of automation, e.g., for liquid handling, imaging, and/or data acquisition or processing, etc. In some embodiments an integrated robot system comprising one or more robots transports assay-microplates from station to station for, e.g., addition, mixing, and/or incubation of assay constituents (e.g., test agent, target, substrate) and, in some embodiments, readout or detection. A HTS system may prepare, incubate, and analyze many plates simultaneously. Certain general principles and techniques that may be applied in embodiments of a HTS are described in Macarrón R & Hertzberg RP. Design and implementation of high-throughput screening assays. Methods Mol Biol., 565:1-32, 2009 and/or An WF & Tolliday NJ., Introduction: cell-based assays for high-throughput screening. Methods Mol Biol. 486:1-12, 2009, and/or references in either of these. Exemplary methods are also disclosed in High Throughput Screening: Methods and Protocols (Methods in Molecular Biology) by William P. Janzen (2002) and High-Throughput Screening in Drug Discovery (Methods and Principles in Medicinal Chemistry) (2006) by Jorg Hüser. Test agent(s) showing an activity of interest (sometimes termed "hits") may be retested and/or, optionally (e.g., depending at least in part on results of restesting) selected for further testing, development, or use.

Positive and/or negative controls may be used in any of the assays. An appropriate positive or negative control can be selected based at least in part on the assay. In some embodiments an agent known to modulate a GCS protein may be used as a positive control. For example, a known GCS inhibitor may be used as a positive control in a screen to identify additional GCS inhibitors. A negative control may be to perform the assay in the absence of a test agent. In some embodiments one or more test agents that exhibit a selected degree of activity (e.g., inhibitory activity on a GCS protein) may be identified and, optionally, selected for further testing or development or use. For example, one or more test agents that exhibit at least 50%, 60%, 70%, 80%, 90%, 100%, 125%, 150%, 200%, or more, of the activity of a positive control may be identified and, optionally, selected for further testing, development, or use.

In some embodiments a first screen is performed to identify agents that bind to a target protein, e.g., a GCS protein, and a second screen is performed to identify those agents that inhibit the target protein and/or have a selected potency. In some embodiments one or more assays or screens is/are performed to identify test agents that bind to and/or inhibit a GCS protein, and the ability of identified test agents to inhibit survival or proliferation of tumor cells, e.g., tumor cells that overexpress SHMT2, is then assessed. The effect of a test agent may be assessed using one or more tumor cell lines, e.g., tumor cell lines that overexpress SHMT2. In some embodiments efficacy may be assessed in 2, 5, 10, or more tumor cell lines. In some embodiments efficacy may be assessed using a tumor cell line comprising CSCs.

GCS proteins (or RNA encoding them) or cells may be contacted with one or more test agent(s) for various periods of time. An appropriate duration may be selected based, e.g., on any of a variety of considerations, e.g., the indicator to be detected, the reaction being assessed, the amount or rate of synthesis or degradation or activity of a target, the concentration or amount of test agent, etc. In some embodiments target RNA(s), protein(s), or cells are contacted with test agent(s) for between 5 minutes and 20 days, e.g., for between 5 and 60 minutes, between 1 hours (h) and 6 h, between 6 h and 12 h, between 12 h and 48 h, between 48 h and 72 h, between 3 days and 5 days, between 5 days and 10 days, between 10 days and 20 days, or any intervening range or particular value. Cells may be contacted with a test agent during all or part of a culture period. A test agent may be replenished once or more during a culture period, e.g., between media changes or at the time of media changes. In some embodiments a test agent may be removed prior to assessing expression or activity. In some embodiments cells are contacted in vivo by administering a test agent to a subject, e.g., a test animal. A test agent may be administered once or more than once (multiple doses). The effect of the test agent on a tumor or subject may be assessed at one or more time points following administration. In some embodiments the effect of a test agent on a tumor or subject may be assessed at one or more time points between 12 h and 52 weeks after initial administration. For example, the effect may be assessed between 1 week and 4 weeks following administration, between 4 weeks and 12 weeks following administration, between 12 weeks and 24 weeks following administration, between 24 weeks and 48 weeks following administration, or any intervening range or particular value, e.g., about 1, 2, 4, 6, 8, 12, 16, 20, 24, or more weeks following initial administration.

In some embodiments a method comprises (a) contacting one or more test cells with a GCS inhibitor; and (b) assessing the survival and/or proliferation of the one or more test cells. In some embodiments, the method further comprises contacting one or more control cells with the GCS inhibitor; and assessing the survival and/or proliferation of the one or more control cells by the GCS inhibitor. In some embodiments a method comprises (a) contacting one or more test cells with a GCS inhibitor; and (b) detecting the level of inhibition of the survival and/or proliferation of the one or more test cells by the GCS inhibitor. In some embodiments, the method further comprises contacting one or more control cells with the GCS inhibitor; and detecting the level of inhibition of the survival and/or proliferation of the one or more control cells by the GCS inhibitor. In some embodiments the one or more test cells comprise tumor cells. In some embodiments the one or more test cells comprise tumor initiating cells. In some embodiments the one or more test cells comprise tumor cells, and the one or more control cells comprise non-tumor cells. In some embodiments the one or more test cells comprise tumor cells that overexpress SHMT2. In some embodiments the one or more test cells and the one or more control cells originate from the same individual or cell line. In some embodiments the one or more test cells and the one or more control cells originate from the same tissue type or organ type. In some embodiments a GCS inhibitor is contacted with cells in combination with a second anti-tumor agent.

In some embodiments, test cells and control cells are maintained in separate vessels (e.g., separate wells of a microwell plate) under substantially identical conditions when contacted with an agent. In some embodiments the activity of an agent (e.g., a lead compound) may be tested by contacting test cells and control cells that are grown in a co-culture. Co-cultures permit evaluation of the selective survival and/or proliferation properties of two or more populations of cells (e.g., test and control cells) in contact with an agent in a common culture vessel. Typically, each population of cells in a co-culture will have an identifying characteristic that is detectable and distinct from an identifying characteristic of the other population(s) of cells in the co-culture. In some embodiments, the identifying characteristic comprises a level of expression of GFP or other reporter protein and/or a tumor cell marker. However, other identifying characteristics known in the art may be suitable, provided that the identifying characteristic enables measurement of the level of survival and/or proliferation of each of two or more populations of cells in the co-culture. A co-culture may comprise, e.g., between 1% and 99% test cells in some embodiments. In some embodiments the percentage of test cells is between 10% and 90%, between 20% and 80%, between 30% and 70%, between 40% and 60%, e.g., about 50%.

In some embodiments of any of the methods, a GCS component is contacted with multiple different doses (e.g., different concentrations or amounts) of a test agent and/or a GCS component is contacted with a test agent for multiple different durations. For example, in some embodiments of any of the methods, cells are contacted with multiple different doses (e.g., different concentrations or amounts) of a test agent and/or cells are contacted with a test agent for multiple different durations. In some embodiments any of the methods may include obtaining or analyzing a dose response curve for an agent. In some embodiments a dose response curve indicates the level of inhibition of activity of a target by an agent at a plurality of doses. In some embodiments a control dose response curve may be obtained or analyzed, wherein the control dose response curve indicates the level of inhibition of a target by vehicle or an inactive agent at a plurality of doses. In some embodiments a method comprises assessing the potency of an agent, e.g., using a dose response assay. In some embodiments analyzing comprises determining an IC50 or EC50 value for an agent. In some embodiments potency is characterized as a half maximal inhibitor concentration (IC50) of an agent, which is used herein to refer to the concentration of an agent that inhibits a given biological process or component, etc., by 50% (half). In some embodiments potency is characterized as a half maximal effective concentration (EC50) of an agent, which is used herein to refer to the concentration of an agent at which 50% of the maximal response induced by the agent (e.g., inhibition, activation) is observed. In some embodiments the biological process is a metabolic pathway, e.g., the reaction catalyzed by the GCS. In some embodiments the component is a component of a metabolic pathway, e.g., an enzyme. In some embodiments the biological process is cell proliferation or viability. In some embodiments a method comprises determining a GI50 for an agent, which term refers to the concentration of an agent required to inhibit cell proliferation by 50%. In some embodiments a dose response curve, IC50, EC50, or GI50 may be determined using an agent in one or more different compositions or in combination with one or more different agents. In some embodiments a dose response curve, IC50, EC50, or GI50 may be determined for exposure to an agent for a selected time period, e.g., any of the time periods mentioned herein.

In some embodiments any of the methods may include obtaining or analyzing a dose response curve using test cells and/or control cells. In some embodiments a test dose response curve indicates the level of inhibition of test cell survival or proliferation by an agent at a plurality of doses; and a control dose response curve indicates the level of inhibition of control cell survival or proliferation by the agent at a plurality of doses. Test cells may be, e.g., tumor cells that express a target of an agent. Control cells may be, e.g., non-tumor cells, or tumor cells that do not express a target of the agent. In some embodiments control cells are non-tumor cells that originate from the same tissue, organ, or cell type as test cells. In some embodiments a test dose response curve indicates the level of inhibition of test cell survival or proliferation by an agent at a plurality of doses; and a control dose response curve indicates the level of inhibition of control cell survival or proliferation by vehicle or an inactive agent at a plurality of doses. In some embodiments analyzing comprises determining an IC50 value for an agent on test cells and/or control cells. In some embodiments the IC50 value for the agent on test cells differs from the IC50 value for the agent on control cells in a statistically significant manner. In some embodiments the IC50 value for the agent on tumor cells is statistically significantly lower than the IC50 value for the agent on non-tumor cells. In some embodiments the IC50 of a GCS inhibitor may be between about 2 and about 1000-fold lower, e.g., about 2, 5, 10, 20, 50, 100, 250, 500, or 1000-fold lower, for test cells versus control cells. In some embodiments, the IC50 of an agent may be between about 2 and about 1000-fold lower, e.g., about 2, 5, 10, 20, 50, 100, 250, 500, or 1000-fold lower, for tumor cells than for normal (non-tumor) cells.

Assays of anti-tumor activity of test agents, e.g., candidate anti-tumor agents, may be conducted in vitro and/or in vivo using cells (e.g., tumor cells, tumor cell lines, identified, obtained, or generated using any suitable method) and/or non-human subjects, human subjects, or any suitable system for testing efficacy. In general, any suitable assay may be used to assess the effect of a candidate anti-tumor agent on a tumor cell or tumor. For example, any of a variety of assays for cell viability and/or proliferation may be used in various embodiments; any of a variety of assays for tumor size, growth rate, progression may be used in various embodiments. See, e.g., discussion above for examples. In some embodiments an agent is first identified or characterized in one or more cell-free and/or cell-based assays or screens and then tested in subjects (e.g., test animals), e.g., to assess its effect on tumors in vivo. In general, a test agent, e.g., a candidate anti-tumor agent, may be administered to a subject using any suitable route of administration and may be formulated appropriately (e.g., with one or more carriers) for the selected route of administration. In some embodiments a candidate anti-tumor agent described or identified as described herein may be tested in combination with a second anti-tumor agent.

In some embodiments one or more test agents, e.g., a compound library, is tested to identify compound(s) that enhance the activity of a GCS inhibitor. For example, in some embodiments, a test agent is tested in combination with a known GCS inhibitor and the effect of the combination is compared with the effect of the GCS inhibitor in the absence of the test agent. In some embodiments, a test agent identified as a modulator (e.g., inhibitor) of GCS activity is tested in a secondary assay to measure its effect on one or more individual GCS components. For example, a test agent identified may be tested to determine whether it specifically inhibits GLDC, GCSH, or AMT.

Any of a wide variety of test agents may be used in various embodiments. For example, a test agent may be a small molecule, polypeptide, peptide, nucleic acid, oligonucleotide, lipid, carbohydrate, or hybrid molecule. Agents can be obtained from natural sources or produced synthetically. Agents may be at least partially pure or may be present in extracts or other types of mixtures. Extracts or fractions thereof can be produced from, e.g., plants, animals, microorganisms, marine organisms, fermentation broths (e.g., soil, bacterial or fungal fermentation broths), etc. In some embodiments, a compound collection ("library") is tested. The library may comprise, e.g., between 100 and 500,000 compounds, or more. Compounds are often arrayed in multwell plates. They may be dissolved in a solvent (e.g., DMSO) or provided in dry form, e.g., as a powder or solid. Collections of synthetic, semi-synthetic, and/or naturally occurring compounds may be tested. Compound libraries can comprise structurally related, structurally diverse, or structurally unrelated compounds. Compounds may be artificial (having a structure invented by man and not found in nature) or naturally occurring. In some embodiments a library comprises at least some compounds that have been identified as "hits" or "leads" in a drug discovery program and/or analogs thereof. A compound library may comprise natural products and/or compounds generated using non-directed or directed synthetic organic chemistry. A compound library may be a small molecule library. Other libraries of interest include peptide or peptoid libraries, cDNA libraries, and oligonucleotide libraries.

A library may be focused (e.g., composed primarily of compounds having the same core structure, derived from the same precursor, or having at least one biochemical activity in common). Compound libraries are available from a number of commercial vendors such as Tocris BioScience, Nanosyn, BioFocus, and from government entities. For example, the Molecular Libraries Small Molecule Repository (MLSMR), a component of the U.S. National Institutes of Health (NIH) Molecular Libraries Program distributes a collection of >300,000 chemically diverse compounds with known and unknown biological activities for use, e.g., in high-throughput screening assays (see https://mli.nih.gov/mli/). The NIH Clinical Collection (NCC) is a plated array of approximately 450 small molecules that have a history of use in human clinical trials. These compounds are highly "drug-like" with known safety profiles. The NCC collection is arrayed in six 96-well plates. 50 µl of each compound is supplied, as an approximately 10 mM solution in 100% DMSO. In some embodiments, a collection of compounds comprising "approved human drugs" may be tested. An "approved human drug" is an agent that has been approved for use in treating humans by a government regulatory agency such as the US Food and Drug Administration, European Medicines Evaluation Agency, or a similar agency responsible for evaluating at least the safety of therapeutic agents prior to allowing them to be marketed. A test agent may be, e.g., an antineoplastic, antibacterial, antiviral, antifungal, antiprotozoal, antiparasitic, antidepressant, antipsychotic, anesthetic, antianginal, antihypertensive, antiarrhythmic, antiinflammatory, analgesic, antithrombotic, antiemetic, immunomodulator, antidiabetic, lipid- or cholesterol-lowering (e.g., statin), anticonvulsant, anticoagulant, antianxiety, hypnotic (sleep-inducing), hormonal, or antihormonal drug, etc. In some embodiments an agent has undergone at least some preclinical or clinical development or has been determined or predicted to have "drug-like" properties. For example, an agent may have completed a Phase I trial or at least a preclinical study in non-human animals and shown evidence of safety and tolerability. In some embodiments an agent is not an agent that is found in a cell culture medium known or used in the art, e.g., for culturing vertebrate, e.g., mammalian cells, e.g., an agent provided for purposes of culturing the cells, or, if the agent is found in a cell culture medium known or used in the art, the agent may be used at a different, e.g., higher, concentration when used in a method or composition described herein. In some embodiments an agent is not an agent known in the art as being useful for treating tumors (e.g., for inhibiting tumor cell survival or proliferation or for inhibiting tumor maintenance, growth, or progression) or for treating side effects associated with chemotherapy.

In some embodiments, information derived from sequence analysis, mutational analysis, and/or structural analysis may be used in the identification or analysis of GCS modulators, e.g., GCS inhibitor(s). For example, in some embodiments a structure (e.g., a two-dimensional or three-dimensional structure) of a target, e.g., a GCS protein, generated at least in part using, e.g., nuclear magnetic resonance, homology modeling, and/or X-ray crystallography is used. In some embodiments a structure obtained with a ligand (e.g., an inhibitor) bound to the target may be used. In some embodiments a computer-aided computational approach sometimes referred to as "virtual screening" is used in the identification of candidate modulators, e.g., candidate GCS inhibitors. Structures of compounds may be screened for ability to bind to an enzyme, e.g., to a region (e.g., a "pocket") accessible to the compound. The region may be a known or potential active site or any region accessible to the compound, e.g., a concave region on the surface or a cleft. A variety of docking and pharmacophore-based algorithms are known in the art, and computer programs implementing such algorithms are available. Commonly used programs include Gold, Dock, Glide, FlexX, Fred, and LigandFit (including the most recent releases thereof). See, e.g., Ghosh, S., et al., Current Opinion in Chemical Biology, 10(3): 194-2-2, 2006; McInnes C., Current Opinion in Chemical Biology; 11(5): 494-502, 2007, and references in either of the foregoing articles, which are incorporated herein by reference. In some embodiments a virtual screening algorithm may involve two major phases: searching (also called "docking") and scoring. During the first phase, the program automatically generates a set of candidate complexes of two molecules (test compound and target molecule) and determines the energy of interaction of the candidate complexes. The scoring phase assigns scores to the candidate complexes and selects a structure that displays favorable interactions based at least in part on the energy. To perform virtual screening, this process may be repeated with a large number of test compounds to identify those that, for example, display the most favorable interactions with the target. In some embodiments, low-energy binding modes of a small molecule within an active site or possible active site are identified. Variations may include the use of rigid or flexible docking algorithms and/or including the potential binding of water molecules. In some embodiments the three-dimensional structure of an enzyme's active site may be used to identify potential inhibitors. Agent(s) that have the potential to bind in or near an active site may be identified. These predictions may then be tested using the actual compound. A new inhibitor thus identified may then be used to obtain a structure of the enzyme in an inhibitor/enzyme complex to show how the molecule is binding to the active site. Further changes may be made to the inhibitor, e.g., to try to improve binding. This cycle may be repeated until an inhibitor of sufficient predicted or actual potency (e.g., a desired potency for therapeutic purposes) is identified. Numerous small molecule structures are available and can be used for virtual screening. A collection of compound structures may sometimes referred to as a "virtual library".

For example, ZINC is a publicly available database containing structures of millions of commercially available compounds that can be used for virtual screening (http://zinc.docking.org/; Shoichet, J. Chem. Inf. Model., 45(1): 177-82, 2005). A database containing about 250,000 small molecule structures is available on the National Cancer Institute (U.S.) website (at http://129.43.27.140/ncidb2/). In some embodiments multiple small molecules may be screened, e.g., up to 50,000; 100,000; 250,000; 500,000, or up to 1 million, 2 million, 5 million, 10 million, or more. Compounds can be scored and, optionally, ranked by their potential to bind to a target. Compounds identified in virtual screens can be tested in cell-free or cell-based assays or in animal models to confirm their ability to inhibit activity of a target, e.g., the GCS or a GCS component, and/or to assess their effect on tumor cell survival or proliferation or tumor maintenance or progression. Computational approaches may be used to predict one or more physico-chemical, pharmacokinetic and/or pharmacodynamic properties of compounds identified in a physical or virtual screen. Such information may be used, e.g., to select one or more hits for, e.g., further testing, development, or use. For example, small molecules having characteristics typical of "drug-like" molecules may be selected and/or small molecules having one or more undesired characteristics may be avoided.

In some embodiments one or more agents, e.g., one or more known modulators of the GCS or a GCS component or one or more hits identified in a screen, may be selected for, e.g., further testing, development, or use. A selected hit may be referred to as a "lead" or "lead agent". For example, a lead may be an agent that is determined or predicted to have higher potency, greater selectivity for a target, one or more drug-like properties, potential for useful modification, or any other propert(ies) of interest, e.g., as compared with one or more other hits, e.g., as compared with the majority of other hits. Further testing may comprise, e.g., resynthesis of a hit, retesting of a hit in the same or a different assay, etc. Development of an agent may comprise producing an altered agent, e.g., an altered lead agent. In some embodiments structures of hit compounds may be examined to identify a pharmacophore, which may be used to design additional compounds (e.g., structural analogs). In some embodiments any of the methods may comprise producing an altered agent, e.g., an altered lead agent. In some embodiments a method comprises modifying an agent to achieve or seek to achieve an alteration in one or more properties, e.g., (1) increased affinity for a target of interest; (2) decreased affinity for a non-target molecule, (3) increased solubility (e.g., increased aqueous solubility); (4) increased stability (e.g., in vivo); (5) increased potency; (6) increased selectivity, e.g., for a target molecule or for tumor cells, e.g., a higher selectivity (e.g., higher cytotoxicity) for tumor versus non-tumaor cells; (7) a decrease in one or more side effects (e.g., decreased adverse side effects, e.g., decreased toxicity); (8) increased therapeutic index; (9) one or modified pharmacokinetic properties (e.g., absorption, distribution, metabolism and/or excretion); (10) modified onset of therapeutic action or duration of effect; (11) modified, e.g., increased, oral bioavailability; (12) modified, e.g., increased, tissue or tumor penetration; (13) modified, e.g., increased, cell permeability; (14) modified, e.g., increased, delivery to a selected subcellular organelle; (15) modified, e.g., increased, increased ability to cross the blood-brain barrier (increased ability to cross the blood-brain barrier may be desirable in some embodiments if the agent is to be used to treat central nervous system tumors, e.g., brain tumors; decreased ability to cross the blood-brain barrier may be desirable in some embodiments if the agent has adverse effects on the CNS); (16) altered immunogenicity; (17) altered plasma protein binding.

In some embodiments any of the methods further comprises determining an in vitro activity or in vivo activity or toxicology profile of an altered agent, e.g., an altered lead agent. One or more additional alterations may be performed, e.g., based at least in part on such analysis. Multiple cycles of alteration and testing may be performed, thereby generating additional altered agents. In some embodiments any of the methods may further comprise performing a quantitative structure activity relationship analysis of multiple hit, lead, or altered agents. Alteration may be accomplished through at least partly random or non-predetermined modification, predetermined modification, and/or using computational approaches in various embodiments. In some embodiments alteration may make use of established principles or techniques of medicinal chemistry, e.g., to predictably alter one or more properties. In some embodiments, a first library of test agents is screened using any of the methods described herein, one or more test agents that are "hits" or "leads" is identified. and at least one such hit or lead is subjected to systematic structural alteration to create a second library of compounds structurally related to the hit or lead. The second library is then screened using methods described herein or other methods.

In some embodiments, an agent identified as described herein, e.g., a GCS inhibitor identified as described herein, may have an unknown structure and/or may be part of a mixture comprising multiple potentially active agents. A variety of techniques useful for determining the structures of agents are known and may be used to determine the structure, if desired, such as NMR, infrared (IR) spectroscopy, ultraviolet-visible (UV-Vis) spectroscopy, mass spectrometry, X-ray crystallography, etc. A variety of techniques useful for separating agents are known and may be used to separate agents present in a mixture.

In some embodiments one or more known modulators or one or more identified hits, leads, or altered agents that act on the same target or on different targets, e.g., the same GCS component or different GCS components, may be linked to each other directly or via one or more linkers or a scaffold.

In some embodiments any of the methods may comprise producing an altered agent, e.g., an altered lead agent, by modifying an agent to incorporate or be attached to a label, which may optionally be used to detect or measure the agent or a metabolite of the agent, e.g., in a pharmacokinetic study. In some embodiments any of the methods may comprise producing an altered agent, e.g., an altered lead agent, by modifying an agent to incorporate or be attached to a second moiety (or more than two moieties). In some embodiments a second (or additional) moiety comprises a linker, tag, or targeting moiety. In some embodiments a second (or additional) moiety may modify one or more properties (1)-(17) listed above. In some embodiments a modification may increase delivery of the agent to, or or accumulation of the agent at, a site of desired activity in the body of a subject. A site may be, e.g., a tumor, organ, tissue, cellular compartment (e.g., cytoplasm, organelle), etc.

In some embodiments a moiety that enhances cell permeability may comprise a protein transduction domain (PTD). "Cell permeability" is used interchangeably with "cell uptake" herein and is not intended to imply any particular mechanism. Uptake may comprise traversal of the plasma membrane into the cytoplasm. A PTD is a peptide or peptoid that can enhance uptake by cells, e.g., mammalian cells, of an entitythat comprises it or to which it is attached. Many PTDs are known in the art. Exemplary PTDs include various sequences rich in amino acids having positively charged side chains (e.g., guanidino-, amidino- and amino-containing side chains (e.g., U.S. Pat. No. 6,593,292) such as arginine-rich peptides, sequences from HIV Tat protein (e.g., U.S. Pat. No. 6,316,003); penetratin (sequence derived from the homeodomain of Antennapedia); sequences from a phage display library (e.g., U.S. 20030104622); MTS peptide (sequence derived from the Kaposi fibroblast growth factor signal peptide), etc. Organelle-specific PTDs provide a means to target specific subcellular sites. See, e.g., Jain M, et al. Cancer Res. 65:7840-7846, 2005; Torchilin VP. Adv Drug Deliv Rev.58:1532-1555, 2006; Juliano R L, et al. Wiley Interdiscip Rev Nanomed Nanobiotechnol. 1:324-335, 2009; Stewart K M, et al. Org Biomol Chem. 6(13): 2242-55, 2008; Fonseca S B, et al., Adv Drug Deliv Rev., 61(11):953-64, 2009; Heitz F, et al., Br J Pharmacol., 157(2):195-206, 2009, and references in any of the foregoing, which are incorporated herein by reference. In some embodiments, a PTD may be used to enhance cell uptake of a small molecule, RNAi agent, aptamer, or polypeptide that inhibits a GCS component or a microparticle or nanoparticle that incorporates a GCS inhibitor.

In some embodiments a GCS inhibitor comprises or is physically associated with a moiety that increases mitochondrial localization of the agent, e.g., that increases entry of the agent into the mitochondria. In some embodiments a GCS inhibitor is modified to comprise or be physically associated with such a moiety. Mitochondrial targeting moieties in certain embodiments can include a variety of peptides, peptide mimetics, and non-peptide species. In some embodiments such a moiety is conjugated to a GCS inhibitor or expressed as a fusion protein with a GCS inhibitor in order to target the agent to mitochondria. In some embodiments a mitochondrial targeting moiety comprises or is a functional variant of a naturally occurring mitochondrial targeting signal (MTS). MTSs are often N-terminal, or less frequently C-terminal, cleavable amino acid sequences of, e.g., about 15-40 residues in length, which are often positively charged with relatively few negatively charged residues. They may, e.g., comprise multiple basic (e.g., arginine), hydrophobic (e.g., alanine, leucine), and polar residues (e.g., serine). The targeting signal is generally proteolytically removed by mitochondria processing peptidase during import or inside the mitochondrial matrix. Some mitochondrial proteins are targeted to mitochondria by similar internal sequences that do not undergo cleavage. MTSs are believed to form amphipathic α-helices, which may be important for their recognition by the translocation machineries in the mitochondrial outer (TOM complex) and inner (TIM complex) membranes. In general a sequence having amphiphilicity in combination with localized positive charges from basic residues may direct successful mitochondrial import. Exemplary peptides that may be used to enhance mitochondrial import, include, e.g., SS peptides or XJB peptide mimetics or a series of cationic, lipophilic cell-permeable mitochondrial penetrating peptides at least 4-8 amino acids in length comprising lysine (K) and arginine (R) or d-arginine (r) (selected to provide positive charge), and phenylalanine (F) and cyclohexylalanine (FX) residues (toimpart lipophilicity) (Horton, K H, et al., Chemistry & Biology 15: 375-382 (2008). SS tetrapeptides feature a common structural motif of alternating aromatic and basic residues. XJB peptides are derived from the sequence of gramicidin S antibiotics. Non-peptide mitochondrial targeting species include various lipophilic cationic compounds such as triphenylphosphonium (TPP) or a derivative thereof, e.g., a lower alkyl derivative thereof (e.g., a C1-6 alkyl, e.g., methyl derivative), (2-oxo-ethyl)-triphenyl-phosphonium, or stearyltriphenyl phosphonium. See, e.g., Hoye, A T, et al., Accounts of Chemical Research, Vol. 41(1): 87-97 (2008) and/or Mossalam, M., et al., Ther Deliv. 1(1): 169-193 (2010) or references in either of the foregoing for additional discussion of mitochondrial targeting.

In some embodiments a GCS inhibitor comprises or is modified to comprise or be physically associated with a moiety that increases passage across the blood brain barrier (BBB). In some embodiments a GCS inhibitor is modified to increase its lipophilicity by, e.g., conjugating a lipophilic moiety thereto. In some embodiments an agent, e.g., a GCS inhibitor, may be conjugated to a moiety such as polyethylene glycol (PEG) or a derivative thereof, or another biocompatible organic polymer (either naturally occurring or artificial), resulting in an agent of increased size that has an increased circulation time in the body (e.g., after intravenous administration). The moiety may have a molecular weight, or average molecular weight, of, e.g., between 10 kD and 200 kD in various embodiments. PEGylation (the process of covalent attachment of polyethylene glycol polymer chains to another molecule) may be achieved by incubation of a reactive derivative of PEG with the target molecule. In some embodiments the covalent attachment of PEG to an agent may "mask" the agent from the immune system (reducing immunogenicity and antigenicity), and increase the hydrodynamic size of the agent, which prolongs its circulatory time by reducing renal clearance. PEGylation may provide enhanced water solubility to hydrophobic agents.

In some embodiments a GCS inhibitor comprises or is linked to a targeting moiety. In some embodiments, a targeting moiety binds to a tumor cell surface marker. In some embodiments, a targeting moiety comprises an antibody that binds to a cell surface marker, e.g., a tumor cell surface marker. In some embodiments, a targeting moiety comprises a ligand that binds to a cell surface marker. A small molecule ligand, aptamer, or polypeptide maybe used in some embodiments. For example, folate may be used as a targeting moiety to direct a GCS inhibitor to tumors that express the folate receptor.

In some aspects, altered GCS inhibitors and methods of making an altered GCS inhibitor are provided. In some embodiments an altered GCS inhibitor may be produced as a fusion protein. In some embodiments an altered GCS inhibitor may be produced at least in part by covalently attaching asecond moiety to the agent. In some embodiments the GCS inhibitor and moiety are linked using a linker. A wide variety of linkers, reactive functional groups useful for covalent attachment, and methods of linking various molecules or other entities are known in the art and may be used in various embodiments. Nonlimiting examples are found in Hermanson, G., *Bioconjugate Techniques, 2$^{nd}$* ed., Academic Press (2008). One of ordinary skill in the art will be able to select appropriate linkers and methods. Any suitable linker and/or method can be used to link an agent that inhibits the GCS to a targeting moiety in order to generate a targeted GCS inhibitor. For example, a bifunctional linker may be used. In some embodiments, a linker comprises a cleavage site for an intracellular enzyme, so that the GCS inhibitor may be released from the targeting moiety inside cells that contain the enzyme.

In some embodiments any of the methods may comprise producing a composition by formulating an agent, e.g., a lead agent or altered agent, e.g., an altered lead agent, with a pharmaceutically acceptable carrier. In some embodiments any of the methods may comprise testing a lead or altered agent in vivo, by administering one or more doses of the composition to a subject, optionally a subject harboring a tumor cell or tumor, and evaluating one or more pharmacokinetic parameters, evaluating the effect of the agent on the subject (e.g., monitoring for adverse effects) and/or evaluating the effect of the agent on the growth and/or survival of the cancer cell in the subject. In some embodiments any of the methods may comprise testing a lead or altered agent in a tumor model in vivo, by administering one or more doses of the composition to a non-human animal that serves as a tumor model and evaluating the effect of the agent on the tumor in the subject. For example, tumor size, number, growth rate, or metastasis may be assessed, e.g., as discussed above. In some embodiments samples or data may be acquired at multiple time points, e.g., during or after a dose or series of doses. In some embodiments a suitable computer program may be used for data analysis, e.g., to calculate one or more pharmacokinetic parameters. In certain embodiments, the subject is a mouse, rat, rabbit, dog, cat, sheep, pig, non-human primate, or human. It will be understood that an altered agent, e.g., an altered lead agent, may be produced using any suitable method. In some embodiments an agent or an intermediate obtained in the course of synthesis of the agent may be used as a starting material for alteration. In some embodiments an altered agent may be synthesized using any suitable materials and/or synthesis route.

In some embodiments one or more agents that inhibit the GCS or a GCS component may be identified, designed, or produced based on a known GCS inhibitor or based one or more hits identified in a screen for GCS inhibitors. For example, a known GCS inhibitor or an agent identified as a GCS inhibitor in an assay or screen may be altered, e.g., to produce an altered agent having one or more altered properties, e.g., as described above.

In some aspects, a computer-readable medium is provided. In some embodiments a computer-readable medium stores at least some results of a screen to identify agents that inhibit the GCS or a GCS component. The results may be stored in a database and may include one or more screening protocols, results obtained from a screen, predicted properties of hits, leads, or altered leads, or results of additional testing of hits, leads, or altered leads.

In some embodiments an agent capable of causing a decrease in level or activity of a target, e.g., the GCS or a GCS component, of at least 50% when used in a cell-free or cell-based assay at a concentration equal to or less than approximately 1 mM, 500 µM, 100 µM, 50 µM, 10 µM, 5 µM, or 1 µM, may be screened for, identified, selected, designed, provided, or used. In some embodiments an agent capable of causing a decrease in level or activity of a target, e.g., the GCS or a GCS component, of at least 50% (i.e., a decrease to 50% or less of the activity that would be expected in the absence of the compound) when used in a cell-free or cell-based assay at lower concentrations, e.g., equal to or less than approximately 500 nM, 100 nM, 50 nM, or 10 nM or less, may be identified, selected, designed, or used. In some embodiments an agent capable of causing a decrease in level or activity of a target, e.g., the GCS or a GCS component, of at least 50% when used at a concentration between 0.1-10 nM, may be screened for, identified, selected, designed, provided, or used.

In some embodiments an agent, e.g., a GCS inhibitor, that is capable of causing a decrease of at least 50% in tumor cell survival or proliferation (i.e., a decrease to 50% or less of the number of viable cells that would be expected in the absence of the agent) when used in a suitable cell culture system at a concentration equal to or less than approximately 1 mM, 500 µM, 100 µM, 50 µM, 10 µM, 5 µM, or 1 µM may be screened for, identified, selected, designed, produced, provided, or used. In some embodiments an agent, e.g., a GCS inhibitor, that is capable of causing a decrease of at least 50% in tumor cell survival or proliferation when used in a suitable cell culture system at lower concentrations, e.g., equal to or less than approximately 500 nM, 100 nM, 50 nM, or 10 nM or less may be screened for, identified, selected, designed, produced, provided, or used. In some embodiments an agent, e.g., a GCS inhibitor, that is capable of causing a decrease of at least 50% in tumor cell survival or proliferation when used in a suitable cell culture system when used at a concentration between 0.1-10 nM may be screened for, identified, selected, designed, produced, provided, or used. In some embodiments at least 50% is between 50% and 75%, between 75% and 90%, between 90% and 95%, between 95% and 100%. A decrease of 100% may be a reduction to background levels or essentially no viable cells or no cell proliferation.

In some embodiments, a test agent may be contacted with tumor cells (e.g., tumor cells that overexpress SHMT2) ex vivo, and the tumor cells are then introduced into a test animal that serves as a tumor model. The ability of the test agent to inhibit tumor development, tumor size, or tumor growth is assessed.

In some embodiments a test agent is administered to a test animal that serves as a tumor model. A test agent may be administered by any route or regimen in various embodiments. For example, the test agentcan be administered prior to, concomitant with, and/or following the administration of tumor cells or development of a tumor. A test agent may be administered once or more during the course of the testing period, for example, one, two, three, four, or more times a day, weekly, bi-weekly, or monthly, beginning before or after tumor cells have been administered. In some embodiments, the test agent is administered continuously to the subject (e.g., intravenously or by release from an implant, pump, sustained release formulation, etc.). The dose of the test agent to be administered can depend on multiple factors, including the type of agent, weight of the test animal, frequency of administration, etc. Determination of dosages is routine for one of ordinary skill in the art. In some embodiments doses are 0.01-200 mg/kg (e.g., 0.1-20 mg/kg or 1-10 mg/kg). In some embodiments an agent is administered to a non-human subject, e.g., a non-human mammal, e.g., a rodent such as a mouse, rat, hamster, rabbit, or guinea pig; a dog, a cat, a bovine or ovine, a non-human primate (e.g., a monkey such as a cynomolgus or rhesus monkey). The non-human animal may be used to assess effect of the agent or a combination of agents on tumor formation, growth, progression (e.g., local invasion, regional or distant metastasis), etc. In some embodiments a non-human animal is used to assess efficacy and/or toxicity of an agent or combination of agents. Methods known in the art can be used for such assessment.

A candidate anti-tumor agent that has been assessed in an ex vivo or in vivo tumor model and shown to inhibit tumor cell survival or proliferation or to inhibit tumor maintenance, growth, invasion, metastasis, resistance to chemotherapy, recurrence, or otherwise shown a useful anti-tumor effect may be considered an anti-tumor agent. An anti-tumor agent may be tested in a clinical trial in a population of subjects in need of treatment for cancer to confirm its therapeutic utility or further define subject characteristics or tumor characteristics that correlate with (e.g,. are predictive of) efficacy or to identify particularly effective agents, combinations, doses, etc.

In some aspects, articles, systems, and compositions suitable for performing any of the methods, assays, or screens are provided. In some embodiments a composition comprises a GCS inhibitor and a tumor cell that overexpresses SHMT2. The composition may further include a cell culture medium. The composition may further comprise an agent, e.g., a test agent. An agent may be combined with one or more substances, which may be physiologically acceptable substances or combinations thereof. In general, a physiologically acceptable substance can be contacted with vertebrate cells, e.g., mammalian cells, e.g., human cells, of many types without causing undue cytotoxicity in the amount used.

A difference between two or more values (e.g., measurements) or groups, or a relationship between two or more variables, may be statistically significant. For example, a level of inhibition or reduction of expression, activity, cell proliferation, cell survival, or tumor size, e.g., as compared with a reference or control level, may be statistically significant. As used herein, "statistically significant" may refer to a p-value of less than 0.05 using an appropriate statistical test. One of ordinary skill in the art will be aware of appropriate statistical tests and models for assessing statistical significance, e.g., of differences in measurements, relationships between variables, etc., in a given context. Exemplary tests and models include, e.g., t-test, ANOVA, chi-square test, Wilcoxon rank sum test, log-rank test, Cox proportional hazards model, etc. In some embodiments multiple regression analysis may be used. In some embodiments, a p-value may be less than 0.025. In some embodiments, a p-value may be less than 0.01. In some embodiments a two-sided statistical test is used. In some embodiments, a result or outcome or difference between two or more values is "statistically significant" if it has less than a 5%, less than a 2.5%, or less than a 1% probability of occurring by chance. In some embodiments, a difference between two or more values or a relationship between two or more variables may be statistically significant with a p-value of less than 0.05, less than 0.025, or less than 0.01. In some embodiments, values may be average values obtained from a set of measurements obtained from different individuals, different samples, or different replicates of an experiment. Software packages such as SAS, GraphPad, etc., may be used for performing statistical analysis.

In some embodiments a method of identifying an agent that modulates sensitivity to GCS inhibition comprises (a) performing a screen or assay to identify an agent that modulates, e.g., increases, expression or activity of SHMT2. In some embodiments a method of identifying a candidate agent for treatment of cancer comprises (a) performing a screen or assay to identify an agent that modulates, e.g., increases, expression or activity of SHMT2. In some embodiments a method further comprises (b) testing an agent identified in step (a) in a tumor model, e.g., in combination with a GCS inhibitor. In various embodiments binding assays, activity assays, computer-aided screens, and/or methods of generating altered agents described herein may be used to identify agents that modulate SHMT2 expression or activity.

VII. Methods of Treatment, Systems, and Kits

In some aspects the present disclosure provides methods of treatment. In some embodiments a method of treating a subject in need of treatment for a tumor comprises inhibiting the GCS in the tumor. In some embodiments a method comprises administering a GCS inhibitor to the subject. In some embodiments, any of the methods may comprise predicting the likelihood that a tumor will be sensitive to a GCS inhibitor. For example, in some embodiments, a method comprises determining whether the tumor overexpresses SHMT2, wherein if the tumor overexpresses SHMT2, the tumor has increased likelihood of being sensitive to a GCS inhibitor. In some embodiments, the method comprises determining whether the tumor is of a tumor type that has a tendency to overexpress SHMT2, wherein if the tumor is of a tumor type that has a tendency to overexpresses SHMT2, the tumor has increased likelihood of being sensitive to a GCS inhibitor. In some embodiments a method comprises (a) determining that a subject is in need of treatment for a tumor; and (b) administering a GCS inhibitor to the subject. In some embodiments a method comprises (a) determining that a subject is in need of treatment for an SHMT2-overexpressing tumor; and (b) administering a GCS inhibitor to the subject. In some embodiments a method comprises (a) diagnosing a subject as having a tumor; and (b) administering a GCS inhibitor to the subject. In some embodiments a method comprises (a) diagnosing a subject as having an SHMT2-overexpressing tumor; and (b) administering a GCS inhibitor to the subject. In various embodiments a GCS inhibitor may be any GCS inhibitor described herein, known in the art, or identified or produced as described herein.

A subject may be in need of treatment of a tumor of any type in various embodiments. In some embodiments providing a subject in need of treatment for a tumor comprises diagnosing the subject as having a tumor. A subject may be diagnosed as having cancer or may have been diagnosed as having cancer using any method of diagnosis known in the art. Methods may include, e.g., physical examination, imaging (e.g., CT scan, MRI), histopathological examination and/or molecular analysis of biopsy or surgical specimens, or combinations thereof. See, e.g., DeVita, supra. In some embodiments the subject has a solid tumor. In some embodiments the subject has a carcinoma. In some embodiments the subject has a sarcoma. In some embodiments a subject is in need of treatment for a tumor of a type that has a tendency to overexpress SHMT2. In some embodiments a subject is in need of treatment for a brain tumor, bladder tumor, breast cancer, cervical tumor, colorectal tumor, embryonal tumor, gastric tumor, germ cell tumor, head and neck tumor, hematologic tumor, kidney tumor, melanoma, mesothelial tumor, ovarian tumor, yolk sac tumor, or sarcoma. In some embodiments a tumor is a central nervous system (CNS) tumor. In some embodiments, the CNS tumor is a brain tumor. In some embodiments, the CNS tumor is a glioma. In some embodiments, the glioma is an astrocytic glioma, e.g., an anaplastic astrocytoma (World Health Organization grade III) or glioblastoma (World Health Organization grade IV). In some embodiments a subject is a human. In some embodiments a subject is a non-human animal. In some embodiments a method of treating a tumor in a subject comprises administering an effective amount of a GCS inhibitor to a subject in need thereof. In some embodiments the tumor overexpresses SHMT2. In some embodiments, GCS inhibitors are useful in treating a subject in clinical remission. In some embodiments, the subject has been treated by surgery and may have limited unresected disease.

In some embodiments a subject is at risk of cancer or at risk of cancer recurrence. A subject at risk of cancer may be, e.g., a subject who has not been diagnosed with cancer but has an increased risk of developing cancer. A subject at increased risk of cancer may be, e.g., a subject who has not been diagnosed with cancer but has an increased risk of developing cancer as compared with a control, who may be matched with regard to one or more demographic characteristics such as age, gender, etc. For example, the subject may have a risk at least 1.2, 1.5, 2, 3, 5, 10 or more times that of an age-matched control (e.g., of the same gender), in various embodiments. It will be understood that "age-matched" can refer to the same number of years of age as the subject or within the same age range as the subject (e.g., a range of 5 or 10 years). For example, a control may be up to 5 years older or younger than the subject. Determining whether a subject is considered "at increased risk" of cancer is within the skill of the ordinarily skilled medical practitioner. Any suitable test(s) and/or criteria can be used. For example, a subject may be considered "at increased risk" of developing cancer if any one or more of the following apply: (i) the subject has an inherited mutation or genetic polymorphism that is associated with increased risk of developing or having cancer relative to other members of the general population not having such mutation or genetic polymorphism (e.g., inherited mutations in certain TSGs are known to be associated with increased risk of cancer); (ii) the subject has a gene or protein expression profile, and/or presence of particular substance(s) in a sample obtained from the subject (e.g., blood), that is/are associated with increased risk of developing or having cancer relative to the general population; (iii) the subject has one or more risk factors such as a family history of cancer, exposure to a tumor-promoting agent or carcinogen (e.g., a physical carcinogen, such as ultraviolet or ionizing radiation; a chemical carcinogen such as asbestos, tobacco or smoke components, aflatoxin, arsenic; a biological carcinogen such as certain viruses or parasites); (iv) the subject is over a specified age, e.g., over 60 years of age. A subject suspected of having cancer may be a subject who has one or more symptoms of cancer or who has had a diagnostic procedure performed that suggested or was consistent with the possible existence of cancer. A subject at risk of cancer recurrence may be a subject who has been treated for cancer and appears to be free of cancer, e.g., as assessed by an appropriate method.

Candidate anti-tumor agents and anti-tumor agents, e.g., GCS inhibitors, can be incorporated into compositions, e.g., pharmaceutical compositions. In addition to the active agent(s), e.g., an anti-tumor agent, pharmaceutical compositions typically comprise one or more pharmaceutically acceptable carriers. In some aspects compositions comprising a GCS inhibitor and a pharmaceutically acceptable carrier are provided. In general, a GCS inhibitor can be any of the GCS inhibitors described above or identified as described above. Invarious embodiments pharmaceutical compositions comprising aGCS inhibitor and any pharmaceutically acceptable carrier(s) are provided. In various embodiments pharmaceutical compositions comprising two or more GCS inhibitors and any pharmaceutically acceptable carrier(s). In some embodiments a composition comprises first and second GCS inhibitors, wherein the first and second GCS inhibitors inhibit different GCS components. Certain embodiments are directed to compositions comprising each combination of two or more GCS inhibitors described above or identified as described herein, together with any pharmaceutically acceptable carrier(s). In some embodiments, at least one of the GCS inhibitors inhibits GLDC. In some embodiments, at least one of the GCS inhibitors inhibits GCSH. In some embodiments, at least one of the GCS inhibitors comprises cysteamine or acysteamine salt or prodrug.

As used herein the term "pharmaceutically acceptable carrier" encompasses vehicles, diluents, solvents, fillers, dispersion media, excipients, encapsulating substances, coatings, and other substances that are compatible with pharmaceutical administration to a human or non-human animal. In some embodiments, a pharmaceutically-acceptable carrier is a non-toxic material (at least in the amounts used and in typical subjects) that does not significantly interfere with the biological activity of the active ingredients of a composition. The term "compatible" in the context of a pharmaceutical composition, means that the ingredients of the pharmaceutical compositions are capable of being comingled with an active agent, and with each other, in a manner such that there is no interaction that would substantially reduce the efficacy of the pharmaceutical composition or render it unsuitable for administration, e.g., under conditions of ordinary use.

Supplementary active agents may be incorporated into the compositions in various embodiments. In some embodiments a supplementary active agent is an anti-tumor agent (e.g., as described above). In some embodiments a supplementary active agent enhances the effectiveness of a GCS inhibitor or reduces toxicity or treats a side effect of the GCS inhibitor with which it is administered.

The choice of pharmaceutically acceptable carrier(s) may depend for example, at least in part on the nature of the active agent, e.g., properties such as solubility or stability; compatibility (meaning that substances can be present together in a composition without interacting in a manner that would substantially reduce the efficacy of the pharmaceutical composition under ordinary use situations); dosage format (e.g., tablet, liquid for injection, etc.); and/or route of administration of the composition.

In general, a pharmaceutical composition may be formulated to be suitable for its intended route of administration. Exemplary routes of administration include, e.g., intravenous, intraarterial, intraosseus, respiratory (e.g., by inhalation), intrathecal, intracisternal, intranasal, intraperitoneal, oral or other means of introduction into the gastrointestinal tract (e.g., stomach or small intestine), sublingual, buccal, subcutaneous, intramuscular, intradermal, intraocular, intrasynovial, intravesical, transdermal, cutaneous (onto the skin) (also termed "topical"), vaginal, or rectal administration.

A pharmaceutical composition may, for example, be in the form of a liquid, gel, lotion, tablet, pill, capsule, spray, aerosol, ointment, transdermal patch, suppository, implant, etc., in various embodiments. For oral administration, the agent can be formulated with pharmaceutically acceptable carriers as tablets, pills, dragees, capsules, liquids, gels, syrups, slurries, suspensions, etc. Pharmaceutically acceptable carriers suitable for injection or other parenteral administration methods can include, for example, aqueous solutions such as water (e.g., water for injection), 5% dextrose, Ringer's dextrose, dextrose and sodium chloride, lactated Ringer's, physiologically buffered saline (e.g., sodium chloride solution), alcoholic/aqueous solutions, emulsions or suspensions; or non-aqueous solvents or vehicles such as propylene glycol, polyethylene glycol, vegetable oils such as olive oil, and injectable organic esters that are suitable for administration to a human or non-human subject. In some embodiments a pharmaceutical composition, e.g., a pharmaceutical composition intended for parenteral use, e.g., injection, is sterile. In some embodiments, a pharmaceutically acceptable carrier or composition is sterile. Sterile solutions may be prepared, for example, by incorporating the active agent(s) in the required amount in an appropriate solvent, optionally with one or a combination of ingredients discussed above, followed by filter sterilization. Generally, dispersions may be prepared by incorporating the active compound into a sterile vehicle which contains a basic dispersion medium and the required other ingredients from those enumerated above. In the case of sterile powders for the preparation of sterile injectable solutions, methods of preparation may include vacuum drying or freeze-drying (lyophilization) which yields a powder of the active ingredient plus any additional desired ingredient(s) from a previously sterile-filtered solution thereof.

A pharmaceutical composition may comprise, in addition to an active agent, one or more physiologically acceptable agents that act, for example, as bulking agents, fillers, solubilizers, stabilizers, surfactants, osmotic agents, preservatives, anti-microbial agents, chelating agents, buffers, disintegrants, absorption enhancers, flowability enhancers, etc. Physiologically acceptable compounds compatible with pharmaceutical administration include, for example, carbohydrates, such as glucose, sucrose, lactose; dextrans; polyols such as mannitol; antioxidants, such as ascorbic acid or glutathione. Numerous pharmaceutically acceptable carriers and methods of preparing dosage forms are known in the art. See, e.g., "Remington's Pharmaceutical Sciences", E. W. Martin, 19th Ed., 1995, Mack Publishing Co.: Easton, Pa., and more recent editions or versions thereof, such as Remington: The Science and Practice of Pharmacy. 21st Edition. Philadelphia, Pa. Lippincott Williams & Wilkins, 2005, for additional discussion of pharmaceutically acceptable carriers and methods of preparing pharmaceutical compositions. It will be understood that many pharmaceutically acceptable carriers are suitable for use in any of a variety of different types of pharmaceutical compositions and/or are compatible with any of a variety of administration routes, and discussion herein should not be considered limiting. In some embodiments a method of making a pharmaceutical composition comprising a GCS inhibitor may include, e.g., combining a GCS inhibitor with one or more pharmaceutically acceptable carriers and preparing a dosage form suitable for administration to a subject. In some embodiments a preparation of an active agent, e.g., a GCS inhibitor, is at least 90% pure, e.g., at least 95%, 96%, 97%, 98%, 99%, or more pure when used in a pharmaceutical composition. In some embodiments apharmaceutical composition may be manufactured consistent with good manufacturing practices (GMP). In some embodiments at least some, most, or all pharmaceutically acceptable carriers and other ingredients in a pharmaceutical composition are, if applicable, pharmaceutical grade (USP).

A dose of an agent, e.g., a GCS inhibitor, may be expressed using any appropriate units, e.g., as a total amount (e.g., in milligrams (mg)), amount/body weight (e.g., mg/kg), amount/surface area (e.g., mg/m$^2$), etc. Doses of agents described herein may range, e.g., from about 0.1 μg to 10,000 mg, e.g., from about 1 μg to 5,000 mg, e.g., from about 10 μg to 1000 mg once or more per day, week, month, or other time interval, in various embodiments. Stated in terms of subject body weight, doses in certain embodiments may range from about 0.0001 mg to about 100 mg of agent per kg of body weight per day, e.g., from 0.001 mg to 50 mg of agent per kg of body weight, e.g., from 0.01 mg to 10 mg of agent per kg of body weight. However, lower or higher doses may be used. In certain embodiments doses are expressed in terms of surface area, e.g., between about 1 mg/m$^2$ to about 5,000 mg/m$^2$. One of ordinary skill in the art may choose from among the various active agents and may consider factors such as potency, bioavailability, mode of administration, the activity of the agent(s), the route of administration, the time of administration, the rate of excretion or metabolism of the agent being employed, the duration of treatment, severity of typical or expected adverse side-effects (if any), other agents and/or materials used in combination with the agent, the age, sex, weight, physical condition, general health and prior medical history of the patient being treated, and like factors well known in the medical arts, with a goal of selecting an effective prophylactic or therapeutic treatment regimen while avoiding substantial or unacceptable toxicity.

In various embodiments a GCS inhibitor may be used at the maximum tolerated dose or a sub-therapeutic dose or any dose there between, e.g., the lowest dose effective to achieve a therapeutic effect. Maximum tolerated dose (MTD) refers to the highest dose of a pharmacological or radiological treatment that can be administered without unacceptable toxicity, that is, the highest dose that has an acceptable risk/benefit ratio, according to sound medical judgment. In general, the ordinarily skilled practitioner can select a dose that has a reasonable risk/benefit ratio according to sound medical judgment. A MTD may, for example, be established in a population of subjects in a clinical trial. In certain embodiments an agent is administered in an amount that is lower than the MTD, e.g., the agent is administered in an amount that is about 10%, 20%, 30%, 40%, 50%, 60%, 70%, 80%, or 90% of the MTD.

In some embodiments, an agent or pharmaceutical composition is provided to a subject for an extended period of time, such as repeated administrations for one or more months, between a month and a year, one or more years, or longer. In some embodiments treatment involves administering an agent or pharmaceutical composition repeatedly over the life of the subject. In some embodiments treatment involves regular administrations, for example one or more times a day, one or more times a week, or one or more times a month. In some embodiments an effective daily dose may be administered as two, three, four, five, six, or more sub-doses administered separately at appropriate intervals throughout the day, optionally, in unit dosage forms. Exemplary doses may be selected using in vitro studies, tested in animal models, and/or clinical trials as standard in the art. One of ordinary skill in the art can determine the effective amount of a particular agent (e.g., a GCS inhibitor) without undue experimentation.

In some embodiments a GCS inhibitor or pharmaceutical composition comprising a GCS inhibitor may be used in combination therapies, that is, a GCS inhibitor or pharmaceutical composition comprising a GCS inhibitor may be administered concurrently with, prior to, or subsequent to, one or more other desired therapeutics or procedures. The particular combination of therapies (therapeutics or procedures) to employ in a combination regimen will generally take into account compatibility of the desired therapeutics and/or procedures and the desired therapeutic effect to be achieved. It will also be appreciated that the therapies employed may achieve a desired effect for the same disorder (for example, a GCS inhibitor may be administered concurrently with another anticancer agent), or they may achieve different effects (e.g., control of any adverse effects). For example, other therapies or anticancer agents that may be used in combination with a GCS inhibitor or pharmaceutical composition comprising a GCS inhibitor include, e.g., other anti-cancer agents, e.g., chemotherapeutic drugs, surgery, radiotherapy (e.g., γ-radiation, neutron beam radiotherapy, electron beam radiotherapy, proton therapy, brachytherapy, and systemic radioactive isotopes), endocrine therapy, biologic response modifiers (e.g., interferons, interleukins), hyperthermia, cryotherapy, agents to attenuate any adverse effects, or combinations thereof, useful for treating a subject in need of treatment for a tumor. Agents used in combination may be administered in the same composition or separately in various embodiments. When they are administered separately, two or more agents may be given simultaneously or sequentially (in anyorder). If administered separately, the time interval between administration of the agents can vary. In some embodiments, administration of first and second agents is performed such that (i) a dose of the second agent is administered before more than 90% of the most recently administered dose of the first agent has been metabolized to an inactive form or excreted from the body; or (ii) doses of the first and second agents are administered at least once within 8 weeks of each other (e.g., within 1, 2, 4, or 7 days, or within 2, 3, 4, 5, 6, 7, or 8 weeks of each other); (iii) the therapies are administered during overlapping time periods (e.g., by continuous or intermittent infusion); or (iv) any combination of the foregoing. In some embodiments agents may be administered individually at substantially the same time (e.g., within less than 1, 2, 5, or 10 minutes of one another). In some embodiments agents may be administered individually within less than 3 hours, e.g., less than 1 hour. In some embodiments agents may be administered by the same route of administration. In some embodiments agents may be administered by different routes of administration.

A "regimen" or "treatment protocol" refers to a selection of one or more agent(s), dose level(s), and optionally other aspects(s) that describe the manner in which therapy is administered to a subject, such as dosing interval, route of administration, rate and duration of a bolus administration or infusion, appropriate parameters for administering radiation, etc. Many cancer chemotherapy regimens include combinations of drugs that have different cytotoxic or cytostatic mechanisms and/or that typically result in different dose-limiting adverse effects. For example, an agent that acts on DNA (e.g., alkylating agent) and an anti-microtubule agent are a common combination found in many chemotherapy regimens.

For purposes herein a regimen that has been tested in a clinical trial, e.g., a regimen that has been shown to be acceptable in terms of safety and, in some embodiments, showing at least some evidence of efficacy, will be referred to as a "standard regimen" and an agent used in such a regimen may be referred to as a "standard chemotherapy agent". In some embodiments a standard regimen or standard chemotherapy agent is a regimen or chemotherapy agent that is used in clinical practice in oncology. In some embodiments pharmaceutical agents used in a standard regimen are all approved drugs. See, e.g., DeVita, supra for examples of standard regimens.

In some embodiments a GCS inhibitor is added to a standard regimen or substituted for one or more of the agents typically used in a standard regimen. Such combination therapies are provided herein. Non-limiting examples of cancer chemotherapeutic agents that may be used include, e.g., alkylating and alkylating-like agents such as nitrogen mustards (e.g., chlorambucil, chlormethine, cyclophosphamide, ifosfamide, and melphalan), nitrosoureas (e.g., carmustine, fotemustine, lomustine, streptozocin); platinum agents (e.g., alkylating-like agents such as carboplatin, cisplatin, oxaliplatin, BBR3464, satraplatin), busulfan, dacarbazine, procarbazine, temozolomide, thioTEPA, treosulfan, and uramustine; antimetabolites such as folic acids (e.g., aminopterin, methotrexate, pemetrexed, raltitrexed); purines such as cladribine, clofarabine, fludarabine, mercaptopurine, pentostatin, thioguanine; pyrimidines such as capecitabine, cytarabine, fluorouracil, floxuridine, gemcitabine; spindle poisons/mitotic inhibitors such as taxanes (e.g., docetaxel, paclitaxel), vincas (e.g., vinblastine, vincristine, vindesine, and vinorelbine), epothilones; cytotoxic/anti-tumor antibiotics such anthracyclines (e.g., daunorubicin, doxorubicin, epirubicin, idarubicin, mitoxantrone, pixantrone, and valrubicin), compounds naturally produced by various species of Streptomyces (e.g., actinomycin, bleomycin, mitomycin, plicamycin) and hydroxyurea; topoisomerase inhibitors such as camptotheca (e.g., camptothecin, topotecan, irinotecan) and podophyllums (e.g., etoposide, teniposide); monoclonal antibodies for cancer therapy such as anti-receptor tyrosine kinases (e.g., cetuximab, panitumumab, trastuzumab), anti-CD20 (e.g., rituximab and tositumomab), and others for example alemtuzumab, aevacizumab, gemtuzumab; photosensitizers such as aminolevulinic acid, methyl aminolevulinate, porfimer sodium, and verteporfin; tyrosine and/or serine/threonine kinase inhibitors, e.g., inhibitors of Abl, Kit, insulin receptor family member(s), VEGF receptor family member(s), EGF receptor family member(s), PDGF receptor family member(s), FGF receptor family member(s), mTOR, Raf kinase family, phosphatidyl inositol (PI) kinases such as PI3 kinase, PI kinase-like kinase family members, cyclin dependent kinase (CDK) family members, Aurora kinase family members (e.g., kinase inhibitors that are on the market or have shown efficacy in at least one phase III trial in tumors, such as cediranib, crizotinib, dasatinib, erlotinib, gefitinib, imatinib, lapatinib, nilotinib, sorafenib, sunitinib, vandetanib), growth factor receptor antagonists, and others such as retinoids (e.g., alitretinoin and tretinoin), altretamine, amsacrine, anagrelide, arsenic trioxide, asparaginase (e.g., pegasparagase), bexarotene, bortezomib, denileukin diftitox, estramustine, ixabepilone, masoprocol, mitotane, and testolactone, Hsp90 inhibitors, proteasome inhibitors (e.g,. bortezomib), angiogenesis inhibitors, e.g., anti-vascular endothelial growth factor agents such as bevacizumab (Avastin) or VEGF receptor antagonists, matrix metalloproteinase inhibitors, various pro-apoptotic agents (e.g., apoptosis inducers), Ras inhibitors, anti-inflammatory agents, cancer vaccines, or other immunomodulating therapies, etc. It will be understood that the preceding classification is non-limiting. A number of anti-tumor agents have multiple activities or mechanisms of action and could be classified in multiple categories or classes or have additional mechanisms of action or targets.

In some embodiments a GCS inhibitor may be administered in combination with an agent that acts on or in the mitochondria.

In some embodiments a GCS inhibitor may be administered to a subject in need of treatment for a tumor that has demonstrated resistance to one or more standard chemotherapy agents or regimens.

In some embodiments a GCS inhibitor may be administered in combination with an agent that increases SHMT2 expression or activity.

In some embodiments a GCS inhibitor is administered to a subject in need of treatment for a brain tumor, e.g., GBM, in combination with one or more compounds approved or accepted in the art as useful for treatment of brain tumors. In some embodiments a GCS inhibitor is administered to a subject in need of treatment for a brain tumor in combination with a compound selected from the group consisting of: temozolomide, cannabinoids, antiangiogenic agents (e.g., VEGFR inhibitors such as cediranib or bevacizumab), perillyl alcohol (POH) (a Ras inhibitor), and Hedgehog-Gli signaling inhibitors, e.g., Hedgehog inhibitors such as GDC-0449.

When agents are administered in combination a therapeutic dosage of each agent, a sub-therapeutic dosage of any two or more agents, or a sub-therapeutic dosage of each, may be used in the treatment of a subject having, or at risk of developing, cancer, in some embodiments. A "sub-therapeutic dose" as used herein refers to a dosage which is less than that dosage which would produce or is ordinarily considered sufficient to produce a therapeutic result in the subject if administered in the absence of at least one other agent.

In some embodiments, administering a GCS inhibitor in combination with a standard or experimental chemotherapy agent or regimen may result in enhanced efficacy in one or more tumor types relative to the standard or experimental chemotherapy agent or regimen.

In some embodiments a GCS inhibitor, or combination of agents, is formulated in unit dosage form, e.g., for ease of administration and uniformity of dosage. The term "unit dosage form" as used herein refers to a physically discrete unit of agent(s) appropriate for the subject to be treated. For example, a unit dosage form may be a pill, tablet, or other discrete dosage form for oral administration, or a prefilled syringe or an ampoule or other vessel containing an amount of a liquid composition appropriate for a single administration, etc.

In general, pharmaceutically acceptable carrier(s) employed in a pharmaceutical composition comprising a GCS inhibitor and, optionally, one or more other active agents, is/are typically used at a concentration sufficient to provide a practical size to dosage relationship. The pharmaceutically acceptable carrier(s), in total, may comprise, for example, from about 50% to about 99.99999% by weight of the pharmaceutical compositions, e.g., from about 80% to about 99.99%, e.g., from about 90% to about 99.95%, from about 95% to about 99.9%, or from about 98% to about 99%, in certain embodiments.

In some embodiments a GCS inhibitor may be administered locally to a tissue or organ in which cancer cells are or may be present or that is at increased risk of developing a tumor. In some embodiments, local administration is accomplished by, e.g., direct injection into or in close proximity to the tissue or organ or into a blood vessel that directly supplies or traverses the tissue or organ or by implanting a sustained release implant within or in close proximity to the tissue or organ or by using a pump or other drug delivery device to deliver a composition into or in close proximity to a tissue or organ. In some embodiments, regional perfusion, in which the portion of the systemic circulation containing a tumor is temporarily isolated from the rest of the circulation, may be used. In some embodiments, an agent is administered into a body cavity or space from which a tumor has been removed or that is in fluid communication with asite from which a tumor has been removed. A body cavity or space can be, for example, the peritoneal cavity, intrathecal space, or bladder. In some embodiments, an agent is administered directly into or in close proximity to a tumor. In some embodiments an agent is locally administered during surgery, e.g., to a tissue or organ or body cavity or space containing a tumor or from which a tumor has been removed. As used herein, "in close proximity" typically refers to within 25 cm or less, e.g., within 20 cm or less, e.g., within 10 cm or less, e.g., within 5 cm or less. In some embodiments administration may be self-administration or directing administration.

In some embodiments a GCS inhibitor is administered using a virus vector. For example, an RNAi vector suitable for administration to a subject may be used. In some embodiment the vector has tropism for tumor cells.

A sustained release implant may be implanted at any suitable site. In some embodiments, a sustained release implant may be used to treat a subject at risk of developing a recurrence of cancer. In some embodiments, a sustained release implant may deliver therapeutically useful levels of an active agent for at least 14 days, e.g., at least 30 days, e.g., at least 60 days, e.g., up to 3 months, 6 months, or more.

In some embodiments, inhaled compositions may be of use to achieve local delivery to the lung in, for example, lung cancer patients. Several types of metered dose inhalers are regularly used for administration by inhalation. These types of devices include metered dose inhalers (MDI), breath-actuated MDI, dry powder inhaler (DPI), spacer/holding chambers in combination with MDI, and nebulizers. In some embodiments, an inhaled composition may be used for systemic delivery, wherein an agent is absorbed across the respiratory epithelium, enters the circulatory system, and is transported in the blood so as to reach one or more sites in the body, e.g., one or more sites that harbors or may harbor a tumor or tumor cells.

In some embodiments, intranasal compositions (e.g., nasal sprays or powders) may be used, e.g., for treatment of intranasal tumors. In some embodiments, intranasal compositions may be used for local delivery to the central nervous system (e.g., the brain), for example to treat a subject in need of treatment for a brain tumor. In some embodiments, intranasal compositions may be used for systemic delivery, wherein anagent is absorbed across the nasal mucosa, enters the circulatory system and is transported in the blood so as to reach one or more sites in the body, e.g., one or more sites that harbors or may harbor a tumor or tumor cells.

In some embodiments osmotic blood brain barrier (BBB) disruption may be used to enhance delivery of a therapeutic agent to the brain for treatment of a brain tumor or a metastasis to the brain. Osmotic BBB disruption typically involves placement of an intra-arterial catheter and infusion of a hyperosmolar solution such as 25% mannitol into an artery that supplies the brain, followed by infusion of the therapeutic agent.

An internal (implantable) or external (extracorporeal) pump may be used for adminstration in some embodiments. Such pumps typically include a drug reservoir from which continuous or intermittent release occurs into the target tissue or in the vicinity thereof via a catheter. In certain embodiments an implantable pump and a catheter having a proximal end coupled to the pump and having a discharge portion for infusing therapeutic dosages of an agent into a selected infusion site in an organ or tissue or space within the body such as the spinal canal is used. The pump may be programmed to release predetermined amounts of the agent at predetemined time intervals. For delivery of an agent to the brain parenchyma, a catheter attached to the pump may be implanted so that the discharge portion lies in the brain parenchyma. U.S. Pat. No. 6,263,237 describes exemplary pump and catheter systems and methods for implanting them into the body of a subject and directing the administration of an agent to a desired location in the brain. In some embodiments, convection-enhanced delivery (CED) is used to deliver an agent to a selected location, e.g., in the brain. CED utilizes an applied external pressure gradient to induce fluid convection into target tissue such as the brain or a tumor. A controlled pressure source in stream with a fluid reservoir ensures operation at constant pressure. Fluid is typically administered via a small catheter using a pump, e.g., at pressures up to about 70 mm Hg to drive convective flow. Microfabricated silicon probes having an outlet along an axis perpendicular to the insertion direction can be used to improve delivery. See, e.g., Sawyer, AJ, New methods for direct delivery of chemotherapy for treating brain tumors, Yale J Biol Med. (2006) 79(3-4): 141-52, and references therein. U.S. Pat. Pub. No. 20040215173 describes exemplary apparatus that may be used to administer agents into tissues and/or tumors by convection enhanced delivery.

In some embodiments an agent is delivered to one or more of the CSF-containing chambers of the central nervous system, e.g., any one or more of the ventricles or the cistema magna. (There are two lateral ventricles and midline third and fourth ventricles within the brain.) To deliver an agent to a ventricle or the cistema magna using an infusion pump, the catheter may be implanted so that the discharge portion lies in the ventricle or the cistern magna, respectively. The agent typically at least in part diffuses out of the ventricle or cistema magna. Delivery to these locations can thus allow delivery of the agent to a relatively wide area of the brain rather than localizing it more closely to a specific site although of course such methods can be used for tumors of the ventricles or cistern magna (e.g., ependymal tumors). In certain embodiments delivery to a CSF-containing space is accomplished by surgically implanting a catheter through the skull so that the tip has access to the space. The other end of the catheter is then connected to a reservoir (e.g., an Ommaya reservoir), which is placed beneath the scalp (subcutaneously).

In some embodiments a GCS inhibitor is administered directly to the brain in an implant. For example, a GCS inhibitor may be incorporated into an implantable, biodegradable, polymeric implant that is, for example, placed into the surgical cavity created when a brain tumor is resected. The GLIADEL® Wafer, which is used to administer carmustine is an example of such an implant, in which the polyanhydride copolymer polifeprosan 20, consisting of poly[bis(p-carboxyphenoxy) propane: sebacic acid in a 20:80 molar ratio, is used as a biodegradable polymer. A substantially non-biodegradable polymer such as polyethylene-co-vinyl acetate (EVAc) can be used to produce an implant that may be removed once release of the therapeutic agent falls below a selected level (e.g., a therapeutically effective level).

In some embodiments, an active agent (e.g., a GCS inhibitor) is present as a salt. When used in medicine, a salt should be pharmaceutically acceptable, but non-pharmaceutically acceptable salts may conveniently be used to prepare pharmaceutically-acceptable salts thereof and are not excluded. Pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, and the like. Also, pharmaceutically-acceptable salts can be prepared as alkaline metal or alkaline earth salts, such as sodium, potassium or calcium salts. It will also be understood that an agent can be provided as a pharmaceutically acceptable pro-drug. In some embodiments, an active metabolite can be used. Furthermore it will be appreciated that agents may be modified, e.g., with targeting ligands, moieties that increase their uptake, moieties that increase their biological half-life (e.g., pegylation), e.g., as described above.

In some embodiments, a GCS inhibitor is administered in a preparation that provides sustained and/or delayed release in the gastrointestinal tract. For example, a coated oral dosage form may be used to provide sustained and/or delayed release, wherein the coating at least in part surrounds acore that contains an active agent and controls the location in the digestive system where the active agent is released. In some embodiments, an oral dosage form comprising an enteric coating is used, wherein the enteric coating remains substantially intact in the stomach but dissolves and releases the drug once the small intestine is reached. See, e.g., PCT/US2007/002325 (Enterically coated cystamine, cysteamine and derivatives thereof, published as WO/2007/089670), for non-limiting example of enteric coatings. In some embodiments a dosage form comprising an enteric coating may be used, e.g., to administer cysteamine, a cysteamine salt, a cysteamine derivative, or other GCS inhibitor. In some embodiments an enteric coating may protect the active agent from the gastric environment, promote conversion of a prodrug to an active agent, or promote absorption of the compound.

In some embodiments, an agent, e.g., a GCS inhibitor, is physically associated with a particle. In some embodiments, a particle comprises a microparticle or nanoparticle or a liposome. The term "microparticle" may be used interchangeably with microcapsule, microsphere, microcarrier, and like terms. The term "nanoparticle" may be used interchangeably with nanocapsule, nanosphere, nanocarrier, and like terms. In some embodiments, an agent is physically associated with a medical device such as a stent, shunt, or catheter. For example, an agent may be associated with a coating of such a device. In some embodiments, an agent is physically associated with a gel which, in some embodiments, may be a hydrogel. In some embodiments, an agent is physically associated with a film. In some embodiments, a physical association is a noncovalent association. For example, an agent may be incorporated into or encapsulated by a matrix. In some embodiments, a physical association comprises a covalent bond. For example, an agent may be covalently attached to a particle or a coating of a medical device. In some embodiments, an active agent may be released at least in part as a result of diffusion out of a matrix or breakdown of at least a portion of the matrix. In some embodiments, a matrix may be at least somewhat permeable to the agent. Breakdown may occur due to physical forces, chemical degradation (e.g., spontaneous hydrolysis, enzymatic cleavage), etc. The matrix may disintegrate or dissolve over time or may become less dense.

In some embodiments, a particle, gel, film, or coating comprises a biocompatible polymer. In some embodiments, a biocompatible polymer is biodegradable. A number of artificial (non-naturally occurring) or naturally occurring biocompatible polymers are known in the art of drug delivery and may be used in various embodiments. In some embodiments a polymer is an organic polymer. Examples of organic polymers include polylactides, polyglycolides, polylactide-co-glycolides, polycaprolactones, polyethylenes, polyethylene glycols, polycarbonates, polyanhydrides (e.g. poly(sebacic anhydride)), polyhydroxyacids (e.g., poly($\beta$-hydroxyalkanoate)), polyesters (e.g., polypropylenefumarate), polyorthoesters, poly($\beta$-amino ester)s, polyvinyl alcohols, polycarbonates, polyalkylenes, polyalkylene glycols, polyalkylene oxides, polyurethanes, polyamides, polyacetals, polyethers, polyacrylates, polymethacrylates, polycyanoacrylates, polyureas, carbohydrates (e.g., celluloses, starches, polysaccharides), polypeptides. In some embodiments a polysaccharide comprises a chitosan, alginate, dextran, or cyclodextrin. In some embodiments a polypeptide comprises a collagen or albumin. In some embodiments, a polymer is a derivative or variant of a first polymer. As used herein, "derivatives" of a first polymer include polymers having substitutions, additions of chemical groups, or other modifications known to those of ordinary skill in the art. In some embodiments a polymer derivative comprises a modification of a pendant group or side chain of a first polymer. In some embodiments a polymer derivative comprises the same backbone chain as a first polymer but differs with regard to at least some pendant groups or side chains. In some embodiments a derivative may be synthesized at least in part by modifying a first polymer. In some embodiments a derivative may be synthesized at least in part by polymerization of appropriate monomers.

In various embodiments, a polymer comprises a hydrophilic polymer, hydrophobic polymer, cationic polymer, or anionic polymer. In some embodiments a polymer may be a homopolymer or a copolymer comprising two or more different monomers. A copolymer may be a random polymer, block polymer, or may comprise a combination of random and block sequences in various embodiments. A polymer may be linear or branched in various embodiments. In some embodiments a polymer may be crosslinked. In some embodiments a polymer may be a graft polymer. A polymer may be a comb or brush polymer, star polymer, or dendrimer in various embodiments. In some embodiments, a polymer may comprise a blend of two or more polymers.

A wide variety of methods for obtaining polymers (e.g., by synthesis or obtaining from natural sources) and for forming matrices therefrom are known in the art and may be used in various embodiments. Methods for making microparticles and nanoparticles are known in the art. Exemplary methods include, e.g., spray drying, phase separation, single and double emulsion, solvent evaporation, solvent extraction, and simple and complex coacervation. Particulate polymeric compositions may, for example, be made using techniques such as milling, granulation, extrusion, spheronization, or precipitation. See, e.g., U.S. Patent Publication Nos. 20040092470; 20050181059 and references in any of the foregoing for examples of various techniques and materials that may be of use to produce particles comprising an active agent.

Methods for making implants, e.g., macroscopic implants, are known in the art. In some embodiments, a preformed implant may be made by introducing a liquid composition containing a monomer, polymer, or other suitable material into a mold of a selected shape and maintaining the composition under appropriate conditions for formation of a semi-solid or solid structure. In some embodiments, polymerization, cross-linking, or gelation occurs to form a semi-solid or solid structure. In some embodiments appropriate conditions include the presence of a suitable concentration of an ion, salt, cross-linking agent, or polymerization initiator, which may be added either prior to or following the introduction of the liquid into the mold. In some embodiments, appropriate conditions include applying heat or pressure. In some embodiments, an implant may be formed at least in part by compressing dry or solid particles, optionally while exposing them to heat. In some embodiments, an implant may be formed at least in part by evaporation or sublimation of a solvent from a composition. A mold may be, e.g., any article that contains a cavity, well, space, or depression of suitable shape and dimensions into which a liquid can be introduced. In some embodiments, a liquid composition used for forming an implant comprises an active agent. The active agent may, for example, become entrapped during formation of the implant. In some embodiments, an implant may be produced and subsequently impregnated or at least in part coated with an active agent.

One of ordinary skill in the art may select appropriate components and techniques for making a drug delivery system based on various factors such as, for example, properties of the active agent, desired release profile, intended route of administration, etc. In some embodiments, a drug delivery system that provides a selected rate or amount of release of an active agent may be empirically determined at least in part by formulating multiple compositions, for example, with varying sizes or proportions of active agent and other component(s), and performing suitable tests of dissolution or release.

A particle may be substantially uniform in composition or may be heterogenous in composition. In some embodiments, a particle comprises a core and one or more outer layers (which may be termed shell(s)), wherein the core and outer layer(s) may differ in composition. In some embodiments, the agent is substantially contained in a core. In some embodiments, the agent is substantially contained outside the core.

In various embodiments an active agent may be at least in part encapsulated in a particle (e.g., contained within a hollow, liquid, semi-solid, or solid core) or may be dispersed substantially throughout a matrix or may be present within or attached to a coating layer. A liquid core may comprise an aqueous carrier such as water, an organic solvent, or a lipid, in various embodiments. A film or coating may comprise a single layer or may comprise multiple layers. The layers of a multi-layer film or coating may differ in composition. In some embodiments an active agent is contained substantially in one or more layers at least prior to use for delivering the active agent, e.g., prior to administration to a subject.

A particle may be modified, e.g., by covalent or noncovalent attachment of, or incorporation of, one or more moieties, e.g., to its surface. Such moiet(ies) may, for example, reduce the particle's charge, non-specific binding, immunogenicity, toxicity, or otherwise enhance its biocompatibility, solubility, or stability, or may serve as a targeting moiety. In some embodiments, a particle is modified by attachment of a polymer thereto, such as polyethylene glycol (PEG) or a derivative thereof. In some embodiments a particle may have a targeting moiety attached thereto or incorporated therein. A targeting moiety may already be exposed at the surface of the particle at the time the particle is administered to a subject or may become exposed following administration. A targeting moiety may, e.g., enhance localization of the particle at a particular location in the body (e.g., a site at which a tumor exists or is suspected to exist or is prone to metastasize) or a site from which a tumor has been removed, enhance localization of the particle to particular cells (e.g., tumor cells), enhance cell uptake, etc. In various embodiments a targeting moiety may be covalently attached to a material from which the particle is at least in part comprised, may be admixed with a material during formation of the particle, may be applied to the particle in or as part of a coating layer, etc.

In some embodiments, a microparticle has a diameter or longest dimension of 500 microns (μm) or less, e.g., between 50 μm and 500 μm, between 20 μm and 50 μm, between 1 μm and 20 μm, e.g., between 1 μm and 10 μm. In some embodiments a nanoparticle has a diameter or longest dimension of 1 μm (1000 nm) or less, e.g., between 1 nm and 100 nm, between 100 nn and 200 nm, between 200 nm and 500 nm, or between 500 nm and 1000 nm. "Longest dimension" in this context refers to the longest straight dimension between two points on the surface of a particle. In some embodiments, a film or coating has a thickness of 500 microns (μm) or less, e.g., between 50 μm and 500 μm, between 20 μm and 50 μm, between 1 μm and 20 μm, e.g., between 1 μm and 10 μm.

In some embodiments a particle may be composed at least in part of one or more lipids. Liposomes, for example, which may comprise phospholipids or other lipids, are nontoxic, physiologically acceptable carriers that may be used in some embodiments. Liposomes can be prepared according to methods known to those skilled in the art. In some embodiments, for example, liposomes may be prepared as described in U.S. Pat. No. 4,522,811. Liposomes, including targeted liposomes, pegylated liposomes, and polymerized liposomes, are known in the art (see, e.g., Hansen C B, et al., Biochim Biophys Acta. 1239(2):133-44, 1995; Torchilin V P, et al., Biochim Biophys Acta, 1511(2):397-411, 2001; Ishida T, et al., FEBS Lett. 460(1): 129-33, 1999). In some embodiments, a lipid-containing particle may be prepared as described in any of the following PCT application publications, or references therein: WO/2011/127255; WO/2010/080724; WO/2010/021865; WO/2010/014895; WO2010147655.

In some embodiments, a component of a delivery system has been approved for use in humans by a government agency responsible for regulating the manufacture, marketing, sale, and/or use of therapeutic agents (e.g., pharmaceutical agents), such as the U.S. Food & Drug Administration (FDA), European Medicines Agency (EMA), or similar agency in another country or jurisdiction. In some embodiments, a component of a delivery system has been approved for use in veterinary medicine. In some embodiments, a component of a delivery system is generally recognized as safe (GRAS) by the U.S. FDA.

In some embodiments a pharmaceutical pack or kit containing a GCS inhibitor or composition comprising a GCS inhibitor is provided. In some embodiments the GCS inhibitor is in a powdered or other solid form. The GCS inhibitor or composition, which may be in powdered or solid form, may be mixed with a pharmaceutically acceptable carrier prior to administration. In some embodiments the pack or kit further contains a separately packaged pharmaceutically acceptable carrier or composition for mixing prior to administration. The amount of GCS inhibitor and carrier or composition may be selected to provide an appropriate concentration or a selected number of doses. In some embodiments a pharmaceutical pack or kit contains one or more GCS inhibitors and one or more additional agents for treatment of cancer. The agents may be packaged separately or together. The kit may include instructions for use of the medication. In certain embodiments, the kit includes multiple doses of each agent. The kit may include sufficient quantities of each agent to treat a subject for, e.g., a week, two weeks, three weeks, four weeks, or multiple months, e.g., 2-6 months. The kit may include a full cycle of chemotherapy. In certain embodiments, the kit includes multiple cycles of chemotherapy.

An agent or pharmaceutical composition may be provided in a container having a label affixed thereto, wherein the label has been approved by a government agency responsible for regulating the manufacture, marketing, sale, and/or use of pharmaceutical agents and/or a pharmaceutical composition may be packaged with a package insert approved by such an agency that contains information relevant to the pharmaceutical composition, such as a description of its contents, description of its use in a method of the invention, etc. In some embodiments information comprises instructions for use of the composition to treat a subject in need of treatment for cancer.

In some embodiments a label, package insert, or instructions may recommend or specify that a GCS inhibitor or pharmaceutical composition comprising a GCS inhibitor should be used in conjunction with an appropriate diagnostic test, which may be referred to as a "companion diagnostic", to determine, e.g., whether a patient is a suitable candidate for treatment with the GCS inhibitor or pharmaceutical composition comprising the GCS inhibitor. In some embodiments a companion diagnostic test provides an assessment of the expression or activity of SHMT2. In some embodiments a reagent or kit for performing the diagnostic test may be packaged or otherwise supplied with a GCS inhibitor or pharmaceutical composition comprising a GCS inhibitor. In some embodiments a GCS inhibitor or pharmaceutical composition comprising a GCS inhibitor may be approved by a government regulatory agency (such as the US FDA, the European Medicines Agency (EMA), or government agencies having similar authority over the approval of therapeutic agents in other jurisdictions) e.g., allowed to be marketed, promoted, distributed, sold or otherwise provided commercially, for treatment of humans or for veterinary purposes, with the recommendation or requirement that the subject is determined to be a suitable candidate for treatment with the GCS inhibitor based at least in part on assessing the level of SHMT2 expression or SHMT2 activity in a tumor of the subject to be treated or in a tumor sample obtained from the subject. For example, the approval may be for an "indication" that includes a requirement that a subject or tumor or tumor sample be classified as having high levels or increased levels of SHMT2 expression or SHMT2 activity. Such a requirement or recommendation may be included in, e.g., a package insert or label provided with the GCS inhibitor or pharmaceutical composition. In some embodiments a particular method for detection or measurerement of an SHMT2 gene product or of SHMT2 activity or a specific test reagent (e.g., an antibody that binds to SHMT2 polypeptide or a probe that hybridizes to SHMT2 mRNA) or kit may be specified. In some embodiments the method, test reagent, or kit may have been used in a clinical trial the results of which at least in part formed the basis for approval of the GCS inhibitor or pharmaceutical composition. In some embodiments the method, test reagent, or kit may have been validated as providing results that correlate with outcome of treatment with a GCS inhibitor or pharmaceutical composition comprising a GCS inhibitor.

In some embodiments, if a GCS inhibitor is an agent that has previously (i.e., prior to the present invention) been administered to a subject (e.g., a human) in need of treatment for cancer for a purpose other than treating cancer ("other purpose"), e.g., for treatment of a condition other than cancer, then (i) a subject in need of treatment for cancer may be one to whom the agent would normally be administered for such other purpose; or (ii) the GCS inhibitor may be administered to treat cancer in a composition or combination distinct from that known in the art to be useful for such other purpose or using a dose or route of administration or targeting approach distinct from that known in the art to be useful for such other purpose; and/or (iii) the GCS inhibitor may be administered based at least in part on results of a test that determines whether the tumor is or is likely to be sensitive to GCS inhibition, e.g., an SHMT2-based assay. An SHMT2-based assay may comprise any assay of the expression or activity of SHMT2.

In some embodiments any of the methods of treatment with a GCS inhibitor may further comprise treatment with an agent that is useful for treating NKH. Treatment of NKH may include (i) reduction of plasma concentration of glycine through treatment with sodium benzoate and/or (ii) blocking of glycinergic receptors, most commonly at the N-methyl D-aspartate (NMDA) receptor site. Benzoate is used by the liver to conjugate glycine for excretion, and its administration results in decreased plasma glycine levels.

In some embodiments, determining the level of SHMT2 gene expression or SHMT2 gene copy number in a sample obtained from the tumor comprises providing a tumor sample to a testing facility. In some aspects a method comprises: providing to a testing facility (a) a sample (e.g., a tumor sample) obtained from a subject; and (b) instructions to perform an SHMT2-based assay. In some embodiments the method further comprises receiving a result of the assay and, optionally, treating a subject or selecting a treatment for a subject based at least in part on the result. In some embodiments a method comprises: (a) providing to a testing facility a sample, e.g., a tumor sample, obtained from a subject; and (b) receiving results of an SHMT2-based assay. In some embodiments a method comprises: (a) providing to a testing facility a sample, e.g., a tumor sample, obtained from a subject; and (b) receiving results of an assay for sensitivity to a GCS inhibitor. In some embodiments "providing" to a testing facility encompasses directly providing, arranging for or directing or authorizing another individual or entity to provide, etc. In some embodiments "providing" to a testing facility encompasses entering an order for an assay into an electronic ordering system, e.g., of a health care facility. In some embodiments a method comprises providing, e.g., electronically, a result of an SHMT2-based assay or other assay for sensitivity to a GCS inhibitor. In some embodiments it is contemplated that the assay may be performed at a testing facility that is remote from (e.g., at least 1 kilometer away from) the site where the sample is obtained from a subject. In some embodiments an SHMT2-based assay or other assay for sensitivity to a GCS inhibitor is performed at one or more central testing facilities, which may be qualified or accredited (e.g., by a national or international organization which, in some embodiments, is a government organization or a professional organization) to perform the assay and, optionally, provide a result, e.g., a report comprising a result. A result may comprise one or more scores and/or a narrative description. In some embodiments a sample may be sent to the laboratory, and a report comprising a result of the assay, optionally together with an interpretation, is provided to a requesting individual or entity. In some embodiments a result is provided in an electronic format; optionally a paper copy is provided instead of or in addition to an electronic format.

In some embodiments a result is provided at least in part by entering the result into a computer, e.g., into a database, electronic medical record, etc., wherein it may be accessed by or under direction of a requestor. In some embodiments a result is provided at least in part over a network, e.g., the Internet. It is contemplated that samples and/or results may be transmitted through one or more different entities or individuals, which may carry out one or more steps of a method or assay or may transmit or receive results thereof. All such activities and intermediate steps thereof and methods of implementation are individually and in combination within the scope of the present disclosure.

In some aspects a variety of kits are provided. In some embodiments, a kit comprises at least one reagent useful for identifying a tumor cell or tumor that is sensitive to GCS inhibition and/or useful for assessing the likelihood that a tumor cell or tumor is sensitive to GCS inhibition. Without limiting the kit or its uses in any way, such a kit may be referred to herein for convenience as a "diagnostic kit". In some embodiments, the kit contains an agent that useful for classifying a tumor or tumor cell based on expression of SHMT2 or based on SHMT2 gene copy number. F or example, the agent is of use to detect an SHMT2 gene or an SHMT2 gene product, e.g., SHMT2 mRNA or polypeptide.

In some embodiments, the agent is a nucleic acid, e.g., a probe or primer, that specifically hybridizes to SHMT2 DNA or mRNA or its complement. In some embodiments, the agent is an antibody (primary antibody) or other agent that specifically binds to SHMT2 polypeptide. In some embodiments, a kit further comprises: (a) a detection reagent such as a secondary antibody that binds to a primary antibody, or a substrate, for use in an assay to detet an SHMT2 gene product; (b) one or more control agents (e.g., a probe or primer that does not bind to SHMT2 DNA or mRNA or an antibody that does not bind to SHMT2 polypeptide); (c) a reagent useful for preparing a sample (e.g., for preparing a cell lysate or a tissue section); (d) a reagent useful for performing an enzymatic assay (e.g., a substrate solution); (e) a reagent diluent. In some embodiments, a kit comprises liquid composition (or components thereof) useful for performing cell lysis, antigen retrieval, staining, or for performing or stopping an enzymatic reaction or washing a sample. The liquid composition may contain, for example, a buffer substance, a monvalent or divalent cation (e.g., as a salt), water, etc. In some embodiments, a kit is of use to perform IHC. In some embodiments the kit is ELISA assay kit.

In some embodiments a diagnostic kit comprises a label or package insert indicating that the kit has been cleared or approved by a government agency responsible for or having jurisdiction over regulation of diagnostic tests, devices, health care products, or the like, for use in a method described herein. In some embodiments, a government agency is the US Food & Drug Administration (FDA) or a national or regional regulatory agency in a region or country other than the US that has similar responsibilities or authority with regard to regulating diagnostic tests, devices, health care products, or the like.

In some embodiments a system is adapted or programmed to carry out an assay for measuring expression or activity of SHMT2. In some embodiments the system may include one or more instruments (e.g., a PCR machine), an automated cell or tissue staining apparatus, a device that produces, records, or stores images, and/or one or more computer processors. The system may be programmed with parameters that have been selected for detection and/or quantification of an SHMT2 gene product, e.g., in tumor samples. The system may be adapted to perform the assay on multiple samples in parallel and/or may have appropriate software to provide an interpretation of the result. The system may comprise appropriate input and output devices, e.g., a keyboard, display, printer, etc.

A kit may comprise instructions for use. In some embodiments, instructions comprise written or illustrative material, e.g., in a paper or electronic format (e.g., on a computer-readable medium). Instructions may comprise directions for performing an assay and/or for interpreting results, e.g., in regard to tumor classification or treatment selection or GCS inhibition. In some embodiments a kit may contain an image of stained cells or tissue sections illustrating examples that are useful for interpreting the results obtained using an antibody to predict sensitivity to GCS inhibition or identify a sensitive tumor. For example, the images may show cells or tissues that would be considered "positive" or "negative" for expression of the target of SHMT2 or that would be assigned a numerical score indicative of a level of expression of SHMT2. A kit may comprise an article that can serve as a reference standard or control. For example, a kit may comprise an antibody that does not bind to SHMT2 to serve as a negative control.

In some embodiments a kit comprises ingredients for an assay of use to identify an inhibitor of the GCS. In various embodiments the kit comprises any one or more GCS components or expression vectors suitable for producing one or more GCS components. In some embodiments a kit comprises a detection reagent, a control reagent, or at least one additional reagent suitable for performing an assay.

Articles in a kit may be individually packaged or contained in individual containers, which may be provided together in a larger container such as a cardboard or styrofoam box. In some embodiments one or more reagents or a kit may meet specified manufacturing and/or quality control criteria, e.g., consistency with good manufacturing practices.

EXAMPLES

Example 1 shRNA-Mediated Knockdown of GLDC is Toxic to GBM Stem Cells

Cancer cells frequently display changes in various metabolic activities which play a role in supporting their transformed state. For example, many types of cancer cells employ increased glycolysis through altered pyruvate kinase isoform expression, which may allow glucose metabolites to be preferentially incorporated towards biomass in a manner conducive to rapid growth (1, 2). Recent studies report that mutations in the metabolic enzyme isocitrate dehydrogenase (IDH1) may drive carcinogenesis in certain gliomas and acute myeloid lymphomas (3, 4). Mutations in the metabolic enzyme L-2-hydroxyglutarate dehydrogenase may predispose to GBM or medulloblastoma (5, 6).

While a wide range of metabolic reactions occur in a cancer cell, we hypothesized that amino acid catabolism pathways may be particularly promising targets for cancer therapy for a number of reasons. A set of congenital disorders, such as phenylketonuria or maple syrup urine disease, are caused by loss-of-function mutations in genes required to break down amino acids, which indicates that these enzymes/pathways are biologically important and suggests that they are likely non-redundant. Furthermore, loss of a number of these genes is conditionally tolerable, as patients may survive and thrive with the proper treatments if started sufficiently early in life, and individuals who are heterozygous for loss-of-function mutations are typically asymptomatic. We reasoned that if certain cancers are particularly dependent on these enzymes, the enzymes may be therapeutically targeted without producing intolerable side effects.

We identified a set of genes involved in amino acid catabolism whose loss of function is associated with congenital disorders. Using a gene-expression profile based informed approach, we identified a subset of these genes for which gene expression is positively associated with GBM, GBM tumor initiating cells (e.g., GBM cancer stem cells), and "stemness". We then conducted a directed survey of 20 such genes for their requirement for growth/survival in a GBM tumor-derived tumor initiating cell line, BT145, using shRNA-mediated knockdown.

Example 2 shRNA-Mediated Knockdown of GLDC is Toxic to GBM Stem Cells

We used lentivirus-delivered expression of shRNAs directed against GLDC to examine the effect of GLDC knockdown on the GBM stem cell (GBM-SC) line BT145. BT145 cells were either infected with a lentivirus expressing hairpins targeting GLDC (G1 to G5) or a control hairpin targeting GFP. As shown in FIG. 1A, Western blotting for GLDC demonstrates strong suppression of GLDC expression for hairpins G1, G4, and G5 but not for G2 or G3. When cell viability was measured using a ATP assay, we found that shRNAs G1, G4, and G5 significantly impaired cell viability relative to GFP control hairpin, whereas shRNAs G2 and G3 did not (FIG. 1B). Differences between G1, G4, and G5 to the GFP control were each statistically significant at 5 days and 7.5 days (p<0.05) (error bars not shown for clarity).

The morphology of BT145 neurospheres following GLDC knockdown indicated toxicity. As shown in FIG. 1C, shRNA G2, G3, and GFP infected neurospheres form large, round, and regular spheres, indicating viability. On the other hand, G1, G4, or G5 infected spheres are small, irregular, and are in the process of disintegrating, indicating cell death and impaired growth. Furthermore, secondary spheres could not be formed from G1, G4, or G5 infected neurospheres (not shown). Similar results as shown in FIGS. 1A, 1B, and 1C were obtained for an additional GBM-SC line—line 0308 (not shown).

In summary, lentivirus-delivered expression of three shRNAs directed against GLDC—G1, G4, and G5-were each toxic to the GBM-SC line BT145, and each corresponded with a strong suppression of GLDC expression. On the other hand, shRNAs G2 and G3 only minimally lowered GLDC expression and were not toxic to BT145 cells.

shRNA that target the following sequences in GLDC mRNA were used:

G1:
CGAGCCTACTTAAACCAGAAA (SEQ ID NO: 1)

G2:
CCTGCCAACATCCGTTTGAAA (SEQ ID NO: 2)

G3:
CCACGGAAACTGCGATATTAA (SEQ ID NO: 3)

G4:
GCCACTGGGAAAGAAGTGTAT (SEQ ID NO: 4)

G5:
GAAGTTTATGAGTCTCCATTT (SEQ ID NO: 5)

Example 3

Figure 2:
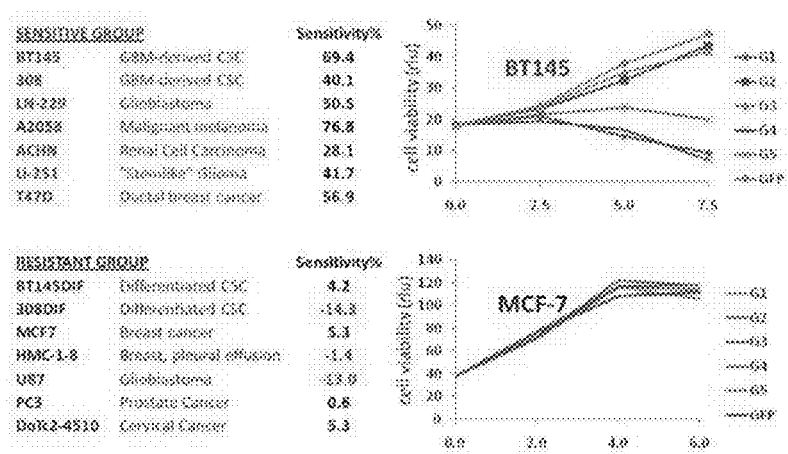
FIG. 2. Different cell lines are either sensitive or insensitive to shRNA-mediated knockdown of GLDC. As shown on the left table in red font, cell lines of varying origins are sensitive to GLDC knockdown. "Sensitivity %" indicates the average % drop in viability following G1 or G5 shRNA expression, where 100% would indicate complete loss of viability. On the right, a plot for BT145 viability (from FIG. 1) is shown as an example of a "sensitive" group cell. On the other hand, shown in blue font, other cells are highly insensitive to GLDC knockdown, ranging from 5.3% sensitivity to −14.3% sensitivity. (negative value indicate that cells had 14.3% higher viability when infected with G1 or G5 shRNAs, relative to GFP shRNA). On the right, a plot for viability of MCF7 cells infected with the various shRNAs are shown as an example of an insensitive cell line. BT145DIF and 308DIF indicates BT145 and 0308 GBMSC lines which were differentiated by serum treatment prior to shRNA infection.

Different Tumor Cell Lines are Either Sensitive or Resistant to shRNA-Mediated Knockdown of GLDC We expanded our analyses to examine multiple cell lines including both non-differentiated GBMSCs and GBMSCs which were differentiated via addition of serum to the media, and various cell lines derived from GBM and other cancer types. We found that each cell type either responded very strongly to GLDC knockdown, or not at all (FIG. 2), thus dividing all cell lines tested into a GLDC-knockdown-sensitive or insensitive group. This pattern did not follow cancer type; for example, both GLDC knockdown sensitive and insensitive examples of GBM derived and breast cancer derived lines were found.

Example 4

Pharmacological Inhibition of the GCS Impairs Viability of GLDC-Knockdown-Sensitive Cells We assessed the effect of treatment with cysteamine, an inhibitor of the GCS (9) on a number of the tumor cell lines that had been examined in the experiments described in Example 3. Cells were treated with cysteamine (1 mM) for 4 days, and cell viability was then assessed using an ATP assay. We observed that cysteamine also impaired viability of only GLDC-knockdown-sensitive cells, but not cells in the insensitive group (FIG. 3A).

Example 5

Figure 3:
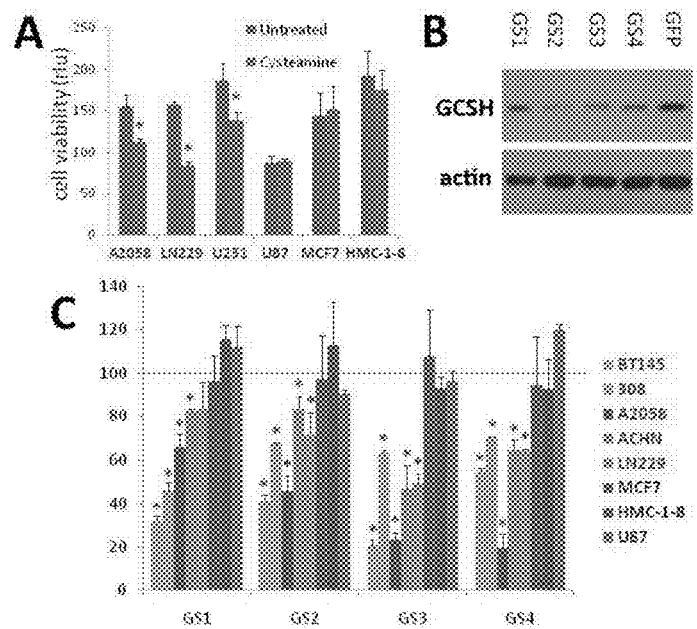
FIGS. 3A-3C. GLDC shRNA sensitive lines, but not insensitive lines, are also sensitive to pharmacological inhibition of the GCS, and to shRNA knockdown of another GCS component (GCSH). (A) Various cell lines were treated with 1 mM cysteamine for 4 days. Cell viability, shown as relative light units, was measured and data from multiple experiments is shown ±S.D. (B) Western blotting for GCSH demonstrates strong suppression of GCSH expression by GS1, GS2, GS3, and GS4 lentiviral shRNAs directed against GCSH, in LN229 cells. (C) Various cells lines were infected with GS1, GS2, GS3, or GS4 shRNAs for 6 days. Cell viability was measured and data from multiple experiments is shown ±S.D. The blue line indicates cell viability for each cell line when infected with control (GFP) shRNA, which was set as 100%. Thus, data for each cell line is shown as a % relative to viability when infected with shGFP. For (A) and (C), asterisk indicates a statistically significant decrease in cell viability following cysteamine treatment relative to untreated (p<0.05). Red font indicates GLDC shRNA-sensitive lines, and blue font indicates insensitive lines.

Inhibition of Glycine Cleavage System Protein H (GCSH) Impairs the Viability of Cell Lines in the GLDC-Knockdown-Sensitive Group We then examined the effect of inhibition of another component of the GCS, glycine cleavage system protein H (GCSH) using the same viability assay as used in Example 4 and found that shRNA-mediated knockdown of GCSH also impaired the viability of cell lines in the GLDC-knockdown-sensitive group, but not cells in the insensitive group (FIG. 3C). The tightly correlating effects of inhibiting another GCS component, and of pharmacologically inhibiting the GCS (Example 4), confirm that the effects of infection with GLDC siRNAs were not off-target effects and indicate that the GLDC-knockdown-sensitive or insensitive nature of the different cancer cell lines were biologically significant.

shRNA that target the following sequences in GCSH shRNA were used:

GS1:
CGTTGGGAGATGTTGTTTATT (SEQ ID NO: 6)

GS2:
GTGCGTAAATTCACAGAGAAA (SEQ ID NO: 7)

GS3:
GTGAACTCTATTCTCCTTTAT (SEQ ID NO: 8)

GS4:
GATGAACTTATGAGTGAAGAA (SEQ ID NO: 9)

Example 6

Figure 4:
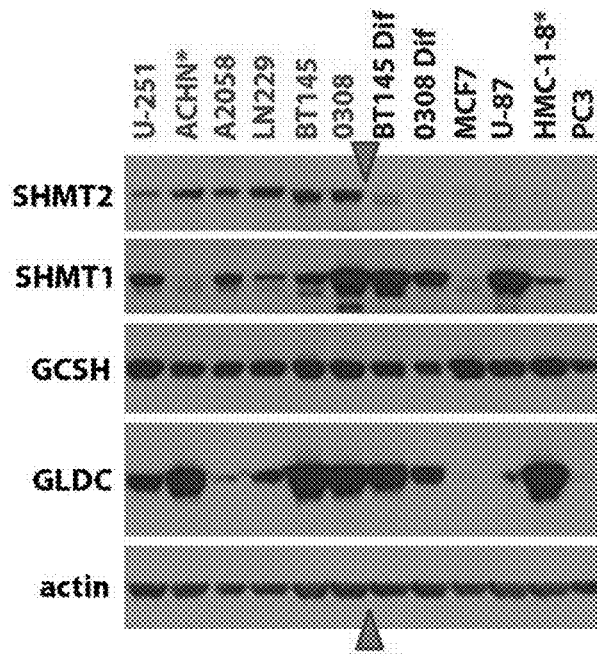
FIG. 4. Mitochondrial serine hydroxylmethyltransferase expression is tightly correlated with sensitivity to GLDC knockdown/GCS inhibition. Numerous cell lines were grown in identical media (neurobasal media supplemented with EGF and FGF) for two days prior to harvesting cells and performing Western blot for various genes involved in the glycine cleavage complex, or proximal metabolic enzymes. Red font indicates cell lines which we had previously determined, as shown in FIG. 2, to be sensitive to GLDC knockdown; blue font indicates insensitive cell lines. 'BT145 Dif' and '0308 Dif' indicates BT145 and 0308 GBM-SC lines which were induced to differentiate by growing in media containing 10% inactivated fetal bovine serum.

Mitochondrial Serine Hydroxylmethyltransferase Expression is Tightly Correlated with Sensitivity to GLDC To uncover what determines sensitivity to GLDC knockdown, we examined the expression levels of GLDC and enzymes directly relevant to glycine metabolism in these cell types. Unexpectedly, we observed that expression levels of GLDC did not correlate with whether cells are sensitive to GLDC knockdown (FIG. 4). No correlation was observed for GCSH or cytoplasmic serine hydroxymethyltransferase (SHMT1), which is involved in the interconversion of glycine and serine. On the other hand, we observed that mitochondrial serine hydroxymethyltransferase (SHMT2), which is involved in the conversion of serine to glycine in the mitochondria (8), was tightly correlated with sensitivity to GLDC knockdown. Cells that were sensitive to GLDC knockdown had a markedly higher expression of SHMT2 compared to insensitive cells.

As shown in FIG. 4, protein expression levels of GLDC, GCSH, or SHMT1 did not correlate with sensitivity to GLDC knockdown/inhibition. On the other hand, protein expression levels of SHMT2 were tightly correlated with sensitivity to GLDC knockdown/inhibition; sensitive cells expressed high levels of SHMT2, while insensitive cells had low levels.

Example 7

Knockdown of SHMT2 Greatly Reduces Sensitivity to GLDC Knockdown

Figure 5:
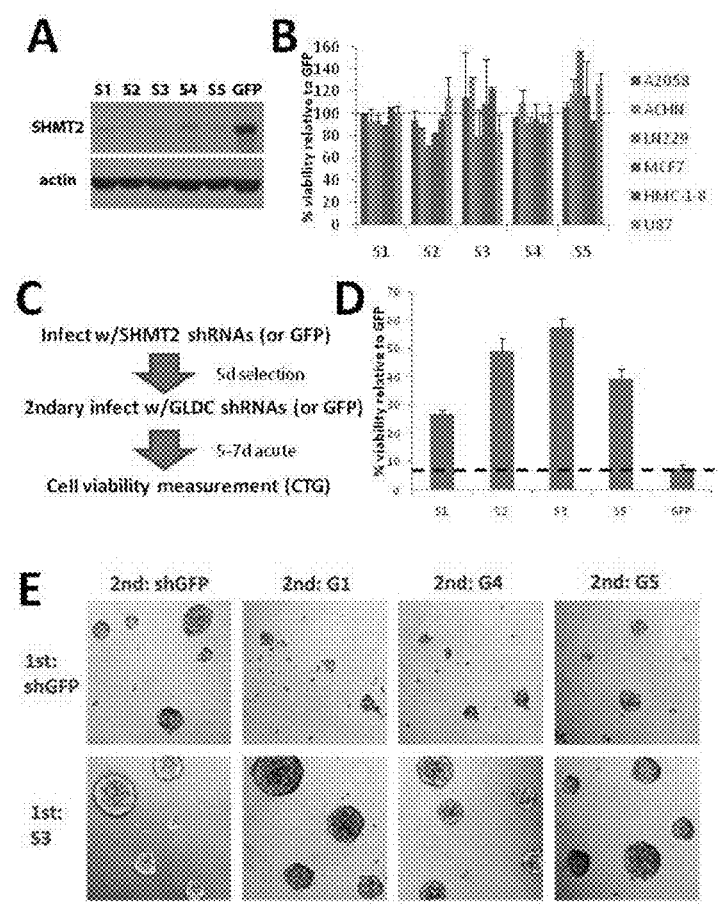
FIGS. 5A-5E. Knockdown of SHMT2 rescues against the toxic effects of GLDC knockdown. (A) ShRNAs S1~S5, directed against SHMT2, effectively knock down SHMT2. Shown are Western Blot analyses from BT145 cells infected with S1~S5 or control (GFP) shRNAs for 5 days. Similar results were observed across various cell lines (not shown). (B) Various cell lines were infected with S1~S5 or control (GFP) shRNAs for 6 days then measured for cell viability. The blue line indicates cell viability for each cell line when infected with control (GFP) shRNA, which was set as 100%. Thus, data for each cell line is shown as a % relative to viability when infected with shGFP. Data are shown as average from multiple experiments ±S.D. As shown, SHMT2 knockdown did not significantly affect cell viability in all cell lines tested. (C) Scheme for examining whether loss of SHMT2 affects cell sensitivity to GLDC knockdown. Cell lines were first infected with shRNAs directed against SHMT2 then selected in puromycin for 5 days to obtain cells with stable integration and stable expression of the shRNAs. Next, these cells were subjected to a second round of infection with shRNAs directed against GLDC, and cell viability was measured at 5-7 days. (D) Cell viability of cell s stably infected with SHMT2 or GFP shRNAs (labeled on X axis), then secondarily infected with G1 shRNA. Dotted line indicates the level of cell viability of cells initially expressing GFP shRNAs then infected with G1 for 7 days. Viability is expressed as a % of the viability when each stable line was secondarily infected with GFP shRNAs, which was set at 100%. (E) Representative light micrographs of neurospheres initially expressing either GFP or S3 shRNAs then secondarily infected with G1, G4, or G5 shRNAs. As shown, G1, G4, or G5 infection of shGFP-expressing cells results in small, disintegrating neurospheres indicative of cell death, while cells expressing S3 are protected.

To examine whether the high expression of SHMT2 in GLDC-knockdown-sensitive cells is functionally relevant or only correlative, we examined the effect of knocking down SHMT2 using shRNAs. First, we examined whether knocking down SHMT2 affected cell viability in either the sensitive or insensitive group of cells (FIG. 5). We observed that SHMT2 knockdown did not significantly affect cell viability in either the sensitive or insensitive cells (FIG. 5B). To examine whether SHMT2 expression directly affects sensitivity to GLDC knockdown, we first generated cell lines (GBM-derived tumor initiating cells and GBM-derived cell lines) stably expressing either control shRNA or shRNAs against SHMT2, prior to lentiviral knockdown of GLDC. To examine whether loss of SHMT2 affects cell sensitivity to GLDC knockdown, cell lines were first infected with shRNAs directed against SHMT2 then selected in puromycin for 5 days to obtain cells with stable integration and stable expression of the shRNAs. Next, these cells were subjected to a second round of infection with shRNAs directed against GLDC, and cell viability was measured at 5-7 days. We observed that in cells stably expressing control shRNA (GFP), knockdown of GLDC resulted in significant toxicity, as predicted. On the other hand cells which had stable shRNA-mediated knockdown of SHMT2 were dramatically rescued against GLDC knockdown-mediated toxicity. For example, FIG. 5D shows cell viability of BT145 cells stably infected with SHMT2 or GFP shRNAs (labeled on X axis), then secondarily infected with G1 shRNA. Dotted line indicates the level of cell viability of cells initially expressing GFP shRNAs then infected with G1 for 7 days. Viability is expressed as a % of the viability when each stable line was secondarily infected with GFP shRNAs, which was set at 100%. Similar rescue was obtained for SHMT2 shRNA-expressing cells secondarily infected with G4 or G5 hairpin (data not shown). Similar results were obtained for BT112 GBM-SC line and LN229 and U251 GBM-derived cell lines (data not shown). FIG. 5E shows representative light micrographs of neurospheres initially expressing either GFP or S3 shRNAs then secondarily infected with G1, G4, or G5 shRNAs. As shown, GI, G4, or G5 infection of shGFP-expressing cells results in small, disintegrating neurospheres indicative of cell death, while cells expressing S3 are protected. Similar results were observed for initial infection of S1, S2, or S5.

Along with the data in FIG. 4, these results indicate that the expression level of SHMT2 is a critical determinant of cancer cell sensitivity to knockdown or inhibition of GLDC/GCS in a wide variety of tumor cells.

shRNA that target the following sequences in SHMT2 mRNA were used:

```
S1:
                                    (SEQ ID NO: 10)
TAGGGCAAGAGCCAGGTATAG

S2:
                                    (SEQ ID NO: 11)
CGGAGAGTTGTGGACTTTATA

S3:
                                    (SEQ ID NO: 12)
CCGGAGAGTTGTGGACTTTAT

S4:
                                    (SEQ ID NO: 13)
GCTCCAGGATTTCAAATCCTT
```

Example 8

SHMT2 mRNA Expression is Significantly Elevated in Many Different Cancer Types

We examined gene expression profiles of different cancers to determine whether there are cancers which have elevated levels of SHMT2, which would indicate that they are suitable targets for therapy based on impairing the GCS. We conducted a comprehensive gene expression profile analyses using the cancer array database Oncomine (10) and searched for cancers in which SHMT2 transcripts are increased at least twofold, with high statistical significance (P<1E$^{-4}$, gene rank within top 10% of all overexpressed genes). We found that SHMT2 mRNA levels are significantly elevated in a large number of cancers, relative to normal tissue controls, and in most cases SHMT2 was within the top 1% of overexpressed genes in that particular cancer (Table 1). These results indicate that targeting the glycine cleavage system is likely to be a valid therapeutic strategy in a wide variety of cancer subtypes which display elevated SHMT2.

TABLE 1

SHMT2 transcripts are significantly elevated in a number of cancers, as analyzed with Oncomine (www.oncomine.com).

| Cancer type | Specific Subtype | PMID | Fold | P-value | Rank % |
|---|---|---|---|---|---|
| Brain | Anaplastic Oligodendroglioma vs. Normal | 16357140 | 4.470 | 3.07E–14 | 1% |
|  | Glioblastoma vs. Normal | 16616334 | 3.239 | 4.48E–12 | 5% |
|  | Oligodendroglioma vs. Normal | 16616334 | 2.798 | 3.13E–10 | 3% |
|  | Anaplastic Astrocytoma vs. Normal | 16616334 | 2.417 | 1.02E–08 | 2% |
|  | Diffuse Astrocytoma vs. Normal | 16616334 | 2.132 | 4.44E–06 | 1% |
|  | Glioblastoma vs. Normal | 16204036 | 2.124 | 6.42E–09 | 2% |
| Bladder | Infiltrating Urothelial Carcinoma vs. Normal | 15930339 | 4.666 | 1.79E–11 | 1% |
|  | Superficial Bladder Cancer vs. Normal | 16432078 | 3.841 | 2.17E–22 | 1% |

TABLE 1-continued

SHMT2 transcripts are significantly elevated in a number of cancers, as analyzed with Oncomine (www.oncomine.com).

| Cancer type | Specific Subtype | PMID | Fold | P-value | Rank % |
|---|---|---|---|---|---|
| | Superficial Bladder Cancer vs. Normal | 15930339 | 3.323 | 8.58E−10 | 1% |
| | Superficial Bladder Cancer vs. Normal | 15173019 | 2.727 | 1.75E−11 | 1% |
| | Infiltrating Urothelial Carcinoma vs. Normal | 15173019 | 2.649 | 6.94E−10 | 1% |
| | Infiltrating Urothelial Carcinoma vs. Normal | 16432078 | 2.575 | 3.93E−17 | 1% |
| Cervical | Cervical Cancer vs. Normal | 17510386 | 2.996 | 1.64E−06 | 10% |
| Colorectal | Rectal Adenoma vs. Normal | 18171984 | 4.275 | 3.54E−09 | 1% |
| | Colon Adenoma vs. Normal | 18171984 | 2.439 | 8.65E−17 | 1% |
| | Cecum Adenocarcinoma vs. Normal | 17615082 | 2.185 | 1.07E−07 | 2% |
| | Colon Mucinous Adenocarcinoma vs. Normal | 17615082 | 2.119 | 3.27E−06 | 4% |
| | Colon Adenocarcinoma vs. Normal | 17615082 | 2.117 | 1.21E−08 | 4% |
| Gastric | Gastric Intestinal Adenocarcinoma vs. Normal | 19081245 | 2.076 | 4.09E−09 | 5% |
| Head and Neck | Floor of the Mouth Carcinoma vs. Normal | 17510386 | 5.121 | 2.90E−05 | 4% |
| Kidney | Renal Wilms Tumor vs. Normal | 19445733 | 4.165 | 3.72E−05 | 1% |
| | Clear Cell Renal Cell Carcinoma vs. Normal | 17699851 | 3.991 | 3.53E−08 | 2% |
| | Non-hereditary CCRCC vs. Normal | 19470766 | 3.482 | 1.29E−10 | 2% |
| | Clear Cell Renal Cell Carcinoma vs. Normal | 19445733 | 3.234 | 6.21E−06 | 3% |
| | Hereditary CCRCC vs. Normal | 19470766 | 3.022 | 9.34E−10 | 4% |
| Leukemia | T-Cell Acute Lymphoblastic Leukemia vs. Normal | 17410184 | 2.215 | 4.56E−07 | 5% |
| | Acute Myeloid Leukemia vs. Normal | 17410184 | 2.203 | 4.60E−09 | 3% |
| Ovarian | Ovarian Serous Cystadenocarcinoma vs. Normal | N/A | 2.238 | 1.32E−11 | 1% |
| Sarcoma | Myxoid/Round Cell Liposarcoma vs. Normal | 20601955 | 2.476 | 6.02E−12 | 2% |
| Other | Pleural Malignant Mesothelioma vs. Normal | 15920167 | 5.904 | 4.23E−10 | 1% |
| | Mixed Germ Cell Tumor vs. Normal | 16424014 | 5.093 | 2.20E−22 | 1% |
| | Embryonal Carcinoma vs. Normal | 16424014 | 4.389 | 9.47E−11 | 1% |
| | Seminoma vs. Normal | 16424014 | 4.215 | 2.26E−10 | 1% |
| | Yolk Sac Tumor vs. Normal | 16424014 | 3.822 | 4.10E−08 | 1% |
| | Teratoma vs. Normal | 16424014 | 3.104 | 1.99E−09 | 2% |

'PMID' indicates the PubMed reference ID number for the study in which the microarray data is published. 'Fold' indicates fold change over corresponding normal tissue. 'Rank %' indicates the percentile in which SHMT2 placed among cancer-upregulated genes in that particular comparison.

Example 9

SHMT2 Protein Expression is Elevated in GBM

We next examined whether SHMT2 protein levels are upregulated in one of the cancer subtypes exhibiting elevated SHMT2 mRNA levels, namely GBM. Using immunohistochemistry we observed that at a gross level, SHMT2 expression was dramatically increased in GBM tumors compared to normal brain (FIG. 6A). While SHMT2 expression varied among GBM tumors, even the tumors with lowest SHMT2 levels still had dramatically higher signal compared to control brain. At a cellular level, in the normal brain, SHMT2 expression was limited to astrocytes and was present as a punctate cytoplasmic signal consistent with a mitochondrial expression pattern (FIG. 6B). Some tumor features, such as vasculature, are completely devoid of SHMT2 expression (leftmost GBM panel), supporting the specific nature of the IHC signal. Furthermore, secondary only control did not show any signal (not shown). In the tumor tissues, SHMT2 appeared to be highly expressed in most, if not all, tumor cells, at a level per cell that was dramatically higher than seen in the astrocytes. These results verify that in GBM, SHMT2 expression levels are highly elevated relative to normal cells, and thus targeting the GCS may well allow selective targeting of GBM tumor cells. The anti-SHMT2 antibody used in these experiments was from Sigma (SIGMA anti SHMT2 antibody (Ab2)) and was used at 1:250.

REFERENCES

1. Warburg, O. On respiratory impairment in cancer cells. *Science* 124, 269-70 (1956).
2. Christofk, H. R. et al. The M2 splice isoform of pyruvate kinase is important for cancer metabolism and tumour growth. *Nature* 452, 230-3 (2008).
3. Dang, L. et al. Cancer-associated IDH1 mutations produce 2-hydroxyglutarate. *Nature* 462, 739-44 (2009).
4. Parsons, D. W. et al. An integrated genomic analysis of human glioblastoma multiforme. *Science* 321, 1807-12 (2008).
5. Haliloglu, G. et al. L-2-hydroxyglutaric aciduria and brain tumors in children with mutations in the L2HGDH gene: neuroimaging findings. *Neuropediatrics* 39, 119-22 (2008).
6. Van Schaftingen, E., Rzem, R. & Veiga-da-Cunha, M. L: -2-Hydroxyglutaric aciduria, a disorder of metabolite repair. *J Inherit Metab Dis* 32, 135-42 (2009).
7. Kikuchi, G., Motokawa, Y., Yoshida, T. & Hiraga, K. Glycine cleavage system: reaction mechanism, physiological significance, and hyperglycinemia. *Proc Jpn Acad Ser B Phys Biol Sci* 84, 246-63 (2008).
8. Narkewicz, M. R., Sauls, S. D., Tjoa, S. S., Teng, C. & Fennessey, P. V. Evidence for intracellular partitioning of serine and glycine metabolism in Chinese hamster ovary cells. *Biochem J* 313 (Pt 3), 991-6 (1996).
9. Yudkoff, M., Nissim, I., Schneider, A. & Segal, S. Cysteamine inhibition of [15N]-glycine turnover in cystinosis and of glycine cleavage system in vitro. *Metabolism* 30, 1096-103 (1981).
10. Rhodes, D. R. et al. ONCOMINE: a cancer microarray database and integrated data-mining platform. *Neoplasia* 6, 1-6 (2004).
11. Di Pietro, E., Wang, X. L. & MacKenzie, R. E. The expression of mitochondrial methylenetetrahydrofolate dehydrogenase-cyclohydrolase supports a role in rapid cell growth. *Biochim Biophys Acta* 1674, 78-84 (2004).

12. Fu, T. F., Rife, J. P. & Schirch, V. The role of serine hydroxymethyltransferase isozymes in one-carbon metabolism in MCF-7 cells as determined by (13)C NMR. *Arch Biochem Biophys* 393, 42-50 (2001).

Those skilled in the art will recognize, or be able to ascertain using no more than routine experimentation, many equivalents to the specific embodiments described herein. The scope of the present invention is not intended to be limited to embodiments described above.

Section headings used herein are not to be construed as limiting in any way. It is expressly contemplated that subject matter presented under any section heading may be applicable to any aspect or embodiment described herein.

Embodiments or aspects herein may be directed to any agent, composition, article, kit, and/or method described herein. It is contemplated that any one or more embodiments or aspects can be freely combined with any one or more other embodiments or aspects whenever appropriate. For example, any combination of two or more agents, compositions, articles, kits, and/or methods that are not mutually inconsistent, is provided.

Articles such as "a", "an", "the" and the like, may mean one or more than one unless indicated to the contrary or otherwise evident from the context.

The phrase "and/or" as used herein in the specification and in the claims, should be understood to mean "either or both" of the elements so conjoined. Multiple elements listed with "and/or" should be construed in the same fashion, i.e., "one or more" of the elements so conjoined. Other elements may optionally be present other than the elements specifically identified by the "and/or" clause. As used herein in the specification and in the claims, "or" should be understood to have the same meaning as "and/or" as defined above. For example, when used in a list of elements, "or" or "and/or" shall be interpreted as being inclusive, i.e., the inclusion of at least one, but optionally more than one, of list of elements, and, optionally, additional unlisted elements. Only terms clearly indicative to the contrary, such as "only one of" or "exactly one of" will refer to the inclusion of exactly one element of a number or list of elements. Thus claims that include "or" between one or more members of a group are considered satisfied if one, more than one, or all of the group members are present, employed in, or otherwise relevant to a given product or process unless indicated to the contrary. Embodiments are provided in which exactly one member of the group is present, employed in, or otherwise relevant to a given product or process. Embodiments are provided in which more than one, or all of the group members are present, employed in, or otherwise relevant to a given product or process.

Embodiments in which any one or more limitations, elements, clauses, descriptive terms, etc., of any claim (or relevant description from elsewhere in the specification) is introduced into another claim are provided. For example, a claim that is dependent on another claim may be modified to include one or more elements or limitations found in any other claim that is dependent on the same base claim. It is expressly contemplated that any amendment to a genus or generic claim may be applied to any species of the genus or any species claim that incorporates or depends on the generic claim.

Where a claim recites a composition, methods of using the composition as disclosed herein are provided, and methods of making the composition according to any of the methods of making disclosed herein are provided. Where a claim recites a method, a composition for performing the method is provided. Where elements are presented as lists or groups, each subgroup is also disclosed. It should also be understood that, in general, where embodiments or aspects is/are referred to herein as comprising particular element(s), feature(s), agent(s), substance(s), step(s), etc., (or combinations thereof), certain embodiments or aspects may consist of, or consist essentially of, such element(s), feature(s), agent(s), substance(s), step(s), etc. (or combinations thereof). It should also be understood that, unless clearly indicated to the contrary, in any methods claimed herein that include more than one step or act, the order of the steps or acts of the method is not necessarily limited to the order in which the steps or acts of the method are recited. Any method of treatment may comprise a step of providing a subject in need of such treatment. Any method of treatment may comprise a step of providing a subject having a disease for which such treatment is warranted. Any method of treatment may comprise a step of diagnosing a subject as being in need of such treatment. Any method of treatment may comprise a step of diagnosing a subject as having a disease for which such treatment is warranted.

Where ranges are given herein, embodiments in which the endpoints are included, embodiments in which both endpoints are excluded, and embodiments in which one endpoint is included and the other is excluded, are provided. It should be assumed that both endpoints are included unless indicated otherwise. Unless otherwise indicated or otherwise evident from the context and understanding of one of ordinary skill in the art, values that are expressed as ranges can assume any specific value or subrange within the stated ranges in various embodiments, to the tenth of the unit of the lower limit of the range, unless the context clearly dictates otherwise. "About" in reference to a numerical value generally refers to a range of values that fall within ±10%, in some embodiments ±5%, in some embodiments ±1%, in some embodiments ±0.5% of the value unless otherwise stated or otherwise evident from the context. In any embodiment in which a numerical value is prefaced by "about", an embodiment in which the exact value is recited is provided. Where an embodiment in which a numerical value is not prefaced by "about" is provided, an embodiment in which the value is prefaced by "about" is also provided. Where a range is preceded by "about", embodiments are provided in which "about" applies to the lower limit and to the upper limit of the range or to either the lower or the upper limit, unless the context clearly dictates otherwise. Where a phrase such as "at least", "up to", "no more than", or similar phrases, precedes a series of numbers, it is to be understood that the phrase applies to each number in the list in various embodiments (it being understood that, depending on the context, 100% of a value, e.g., a value expressed as a percentage, may be an upper limit), unless the context clearly dictates otherwise. For example, "at least 1, 2, or 3" should be understood to mean "at least 1, at least 2, or at least 3" in various embodiments. It will also be understood that any and all reasonable lower limits and upper limits are expressly contemplated. It is also understood that any embodiment, aspect, feature, or characteristic, or any combination thereof, may be explicitly excluded from any one or more of the claims. For example, any agent, composition, amount, dose, administration route, tumor type, cell type, target, cellular marker, etc., may be explicitly excluded from any one or more claims.

We claim:

1. A method of treating a tumor in a subject, comprising:
   (a) determining whether the tumor overexpresses serine hydroxymethyltransferase-2 (SHMT2) as compared to a control level of expression of SHMT2; and
   (b) administering a therapeutically effective amount of a glycine cleavage system (GCS) inhibitor to the subject with the tumor which overexpresses SHMT2.

2. The method of claim 1, wherein determining whether the tumor overexpresses SHMT2 comprises requesting a test to measure the level of expression of SHMT2 in a sample of the tumor, wherein the SHMT2 is an SHMT2 gene product, and wherein the control level of expression of SHMT2 is a control level of the SHMT2 gene product.

3. The method of claim 2, wherein the control level of SHMT2 gene product is the level of the SHMT2 gene product in a control sample.

4. The method of claim 3, wherein the level of the SHMT2 gene product in the sample of the tumor is at least twice the level of the SHMT2 gene product in the control sample.

5. The method of claim 2, wherein the SHMT2 gene product is an mRNA encoding SHMT2 protein.

6. The method of claim 1, wherein determining whether the tumor overexpresses SHMT2 comprises measuring the level of expression of SHMT2 in a sample of the tumor, wherein the SHMT2 is an SHMT2 gene product and wherein the control level of expression of SHMT2 is a control level of the SHMT2 gene product.

7. The method of claim 6, wherein the control level of the SHMT2 gene product is the level of the SHMT2 gene product in a control sample.

8. The method of claim 1, wherein the GCS inhibitor includes cysteamine or a cysteamine salt, prodrug or analog.

9. The method of claim 1, wherein the GCS inhibitor includes an aminomethyltransferase (AMT) inhibitor.

10. The method of claim 1, wherein the GCS inhibitor includes a glycine decarboxylase (GLDC) inhibitor.

11. The method of claim 1, wherein the GCS inhibitor includes a glycine cleavage system protein H (GCSH) or dihydrolipoamide dehydrogenase (DLD) inhibitor.

12. The method of claim 1, further comprising administering a second anti-tumor agent.

13. The method of claim 6, wherein the SHMT2 gene product is an mRNA encoding SHMT2 protein.

14. The method of claim 1, wherein the tumor has a level of overexpression of SHMT2 which is at least twice the control level of expression of SHMT2.

* * * * *

SEQUENCE LISTING

<160> NUMBER OF SEQ ID NOS: 13

<210> SEQ ID NO 1
<211> LENGTH: 21
<212> TYPE: DNA
<213> ORGANISM: Unknown
<220> FEATURE:
<223> OTHER INFORMATION: GLDC target sequence

<400> SEQUENCE: 1
cgagcctact taaaccagaa a                                              21

<210> SEQ ID NO 2
<211> LENGTH: 21
<212> TYPE: DNA
<213> ORGANISM: Unknown
<220> FEATURE:
<223> OTHER INFORMATION: GLDC target sequence

<400> SEQUENCE: 2
cgagcctact taaaccagaa a                                              21

<210> SEQ ID NO 3
<211> LENGTH: 21
<212> TYPE: DNA
<213> ORGANISM: Unknown
<220> FEATURE:
<223> OTHER INFORMATION: GLDC target sequence

<400> SEQUENCE: 3
ccacggaaac tgcgatatta a                                              21

<210> SEQ ID NO 4
<211> LENGTH: 21
<212> TYPE: DNA
<213> ORGANISM: Unknown
<220> FEATURE:
<223> OTHER INFORMATION: GLDC target sequence

<400> SEQUENCE: 4
gccactggga agaagtgta t                                               21

<210> SEQ ID NO 5
<211> LENGTH: 21
<212> TYPE: DNA
<213> ORGANISM: Unknown
<220> FEATURE:
<223> OTHER INFORMATION: GLDC target sequence

<400> SEQUENCE: 5
gaagtttatg agtctccatt t                                              21

<210> SEQ ID NO 6
<211> LENGTH: 21
<212> TYPE: DNA
<213> ORGANISM: Unknown
<220> FEATURE:
<223> OTHER INFORMATION: GCSH target sequence

<400> SEQUENCE: 6
cgttgggaga tgttgtttat t                                              21

<210> SEQ ID NO 7
<211> LENGTH: 21
<212> TYPE: DNA
<213> ORGANISM: Unknown

```
<220> FEATURE:
<223> OTHER INFORMATION: GCSH target sequence

<400> SEQUENCE: 7
gtgcgtaaat tcacagagaa a                                              21

<210> SEQ ID NO 8
<211> LENGTH: 21
<212> TYPE: DNA
<213> ORGANISM: Unknown
<220> FEATURE:
<223> OTHER INFORMATION: GCSH target sequence

<400> SEQUENCE: 8
gtgaactcta ttctccttta t                                              21

<210> SEQ ID NO 9
<211> LENGTH: 21
<212> TYPE: DNA
<213> ORGANISM: Unknown
<220> FEATURE:
<223> OTHER INFORMATION: GCSH target sequence

<400> SEQUENCE: 9
gatgaactta tgagtgaaga a                                              21

<210> SEQ ID NO 10
<211> LENGTH: 21
<212> TYPE: DNA
<213> ORGANISM: Unknown
<220> FEATURE:
<223> OTHER INFORMATION: SHMT2 target sequence

<400> SEQUENCE: 10
tagggcaaga gccaggtata g                                              21

<210> SEQ ID NO 11
<211> LENGTH: 21
<212> TYPE: DNA
<213> ORGANISM: Unknown
<220> FEATURE:
<223> OTHER INFORMATION: SHMT2 target sequence

<400> SEQUENCE: 11
cggagagttg tggactttat a                                              21

<210> SEQ ID NO 12
<211> LENGTH: 21
<212> TYPE: DNA
<213> ORGANISM: Unknown
<220> FEATURE:
<223> OTHER INFORMATION: SHMT2 target sequence

<400> SEQUENCE: 12
ccggagagtt gtggactta t                                               21

<210> SEQ ID NO 13
<211> LENGTH: 21
<212> TYPE: DNA
<213> ORGANISM: Unknown
<220> FEATURE:
<223> OTHER INFORMATION: SHMT2 target sequence

<400> SEQUENCE: 13
gctccaggat ttcaaatcct t                                              21
```